(12) United States Patent
Fritz et al.

(10) Patent No.: US 6,528,506 B2
(45) Date of Patent: Mar. 4, 2003

(54) INHIBITION OF APOPTOSIS USING INTERLEUKIN-1β-CONVERTING ENZYME (ICE)/CED-3 FAMILY INHIBITORS

(75) Inventors: Lawrence C. Fritz, Rancho Santa Fe, CA (US); Kevin J. Tomaselli, San Diego, CA (US); Donald S. Karanewski, Escondido, CA (US); Steven D. Linton, San Diego, CA (US); Xu Bai, Carlsbad, CA (US)

(73) Assignee: IDUN Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/083,862

(22) Filed: Feb. 25, 2002

(65) Prior Publication Data

US 2002/0147171 A1 Oct. 10, 2002

Related U.S. Application Data

(63) Continuation of application No. 09/737,169, filed on Dec. 11, 2000, now abandoned, which is a continuation of application No. 08/979,909, filed on Sep. 12, 1997, now Pat. No. 6,200,969.
(60) Provisional application No. 60/026,011, filed on Sep. 12, 1996.

(51) Int. Cl.$^7$ ............................................... A61K 31/55
(52) U.S. Cl. ..................................... 514/214; 514/419
(58) Field of Search .................................. 514/214, 419

(56) References Cited

U.S. PATENT DOCUMENTS 5,504,080 A * 4/1996 Karanewsky .......... 514/212.05
5,644,055 A * 7/1997 De Lombaert .............. 540/522
5,756,465 A    5/1998 Sleath et al. ................... 514/17
6,136,787 A   10/2000 Black et al. .................. 514/18
6,204,261 B1   3/2001 Batchelor et al. ........... 514/221

FOREIGN PATENT DOCUMENTS

| EP | 0 547 699 A1 | 6/1993 |
| WO | WO 91/15577 | 10/1991 |
| WO | WO 93/05071 | 3/1993 |

OTHER PUBLICATIONS

Gagliardini et al., "Prevention of Vertebrate Neuronal Death by the crmA Gene," *Science* 263: 826–828, Feb., 1994.*
Miura et al., "Induction of Apoptosis in Fibroblasts by IL–1β–Converting Enzyme, a Mammalian Homolog of the C. elegans Cell Death Gene ced-3," *Cell* 75: 653–660, Nov. 1993.*
Nicholson et al., "Identification and inhibition of the ICE/CED–3 protease necessary for mammalian apoptosis," *Nature* 376: 37–43, Jul., 1995.*
Fletcher et al., "A Synthetic Inhibitor of Interleukin–1β Converting Enzyme Prevents Endotoxin–Induced Interleukin–1β Production In vitro and In vitro," *Journal of Interferon and Cytokine Research* 15(3):243–248, Mar. 1995.

* cited by examiner

*Primary Examiner*—James H Reamer
(74) *Attorney, Agent, or Firm*—Seed Intellectual Property Law Group PLLC

(57) ABSTRACT

The present invention provides methods for expanding and increasing survival of hematopoietic cell populations, for prolonging viablility of an organ for transplantation, and enhancing bioproduction, using interleukin-1β-converting enzyme (ICE)/CED-3 family inhibitors. Exemplary compounds useful in the methods of the invention are provided herein.

7 Claims, 7 Drawing Sheets

TABLE 1
50% INHIBITORY CONCENTRATIONS $IC_{50}$
FOR FORMULA A

| Example | $R^1$ | A | mICE $IC_{50}(\mu M)$ | CPP32 $IC_{50}(\mu M)$ |
|---|---|---|---|---|
| 4 | $CH_3$ | Ala | 0.177 | >10 |
| 7 | $CH_3$ | Pro | 11.7 | >50 |
| 10 | $CH_3$ | Val | 0.531 | 2.48 |
| 13 | $CH_3$ | Leu | 5.52 | 5.62 |
| 16 | $CH_3$ | Phe | 3.34 | 49.8 |
| 21 | $CH_3$ | Gly | 34.7 | >50 |
| 24 | $CH_2Ph$ | Ala | 0.393 | >50 |
| 27 | $(CH_2)_2CH=CH_2$ | Val | 0.313 | 1.45 |
| 30 | $CH_2CO_2H$ | Ala | 1.63 | >50 |
| 33 | $(CH_2)_2CO_2H$ | Ala | 0.198 | >50 |
| reference | — | — | 0.064 | 47.0 |

TABLE 2
DISSOCIATION CONSTANT Ki AND INACTIVATION RATE
$k_3/K_i$ FOR FORMULA B

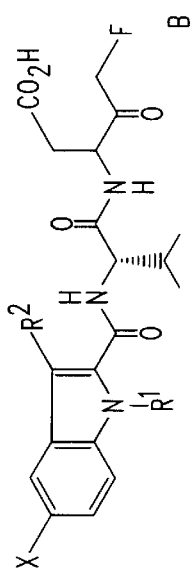

| Example | $R^1$ | $R^2$ | X | mICE $K_i$ (μM) | mICE $k_3/K_i$ ($M^{-1}s^{-1}$) | CPP32 $K_i$ (μM) | CPP32 $k_3/K_i$ ($M^{-1}s^{-1}$) | Mch2 $K_i$ (μM) | Mch2 $k_3/K_i$ ($M^{-1}s^{-1}$) | Mch5 $K_i$ (μM) | Mch5 $k_3/K_i$ ($M^{-1}s^{-1}$) |
|---|---|---|---|---|---|---|---|---|---|---|---|
| 43 | $CH_3$ | $CH_3$ | H | 1.40 | 2,860 | 0.960 | 13,400 | 0.017 | 58,800 | 0.062 | 21,500 |
| 46 | $CH_3$ | Cl | H | 1.68 | 6,150 | 0.830 | 25,900 | ND | ND | 0.099 | 37,000 |
| 49 | $CH_3$ | Cl | F | 1.10 | 7,120 | 0.493 | 72,700 | 0.014 | 71,400 | 0.054 | 52,500 |
| 52 | $(CH_2)_3Ph$ | H | H | 0.133 | 45,100 | 0.742 | 33,700 | 0.024 | 41,700 | 0.077 | 32,500 |
| 55 | Ph | H | H | 0.843 | 8,900 | 0.110 | 74,200 | 0.036 | 55,600 | 0.043 | 35,300 |
| 58 | $CH_2CO_2H$ | H | H | 0.327 | 16,800 | 0.125 | 58,700 | 0.051 | 19,600 | 0.038 | 127,000 |
| 61 | $CH_3$ | H | H | 0.240 | 41,700 | 0.520 | 21,200 | 0.033 | 30,300 | 0.026 | 38,500 |
| 62 | $CH_3$ | $CH_3$ | F | 0.397 | 7,560 | 0.113 | 44,200 | 0.040 | 25,000 | 0.102 | 29,400 |
| 63 | $(CH_2)_2CH=CH_2$ | H | F | 0.327 | 18,300 | 0.125 | 56,000 | 0.104 | 19,200 | 0.038 | 131,600 |
| 64 | $CH_3$ | $CH_2CH(CH_3)_2$ | H | 0.234 | 21,400 | 0.180 | 38,900 | 0.052 | 38,500 | 0.063 | 47,600 |
| 65 | $CH_3$ | $(CH_2)_2Ph$ | H | 4.56 | 1,540 | 2.28 | 7,910 | 0.023 | 43,500 | 0.063 | 31,700 |
| 66 | $CH_3$ | H | H | 0.632 | 14,200 | 0.505 | 21,800 | 0.038 | 26,300 | 0.051 | 39,200 |
| 67 | $CH_3$ | H | $OCH_2Ph$ | 0.739 | 14,900 | 0.346 | 31,800 | 0.040 | 25,000 | 0.062 | 16,100 |
| reference | — | — | — | 0.015 | 278,000 | 0.820 | 14,600 | 0.594 | 3,370 | 0.018 | 83,300 |

*Fig. 2*

TABLE 3
DISSOCIATION CONSTANT Ki AND INACTIVATION RATE
k₃/Ki FOR FORMULA C

| Example | X | mICE Ki (μM) | mICE $k_3/Ki$ $(M^{-1}s^{-1})$ | CPP32 Ki (μM) | CPP32 $k_3/Ki$ $(M^{-1}s^{-1})$ | Mch2 Ki (μM) | Mch2 $k_3/Ki$ $(M^{-1}s^{-1})$ | Mch5 Ki (μM) | Mch5 $k_3/Ki$ $(M^{-1}s^{-1})$ |
|---|---|---|---|---|---|---|---|---|---|
| 43 | F | 1.40 | 2,860 | 0.960 | 13,400 | 0.017 | 58,800 | 0.062 | 21,500 |
| 70 | OCO (2, 6-di-Cl-C₆H₃) | 1.16 | 3,460 | 0.052 | 57,700 | 0.030 | 33,300 | 0.364 | 2,750 |
| 71 | OPO (C₆H₅)₂ | 0.124 | 24,200 | 0.046 | 65,200 | 0.060 | 50,000 | 0.022 | 45,500 |
| 72 | O (1-Ph-3-CF₃-pyrazol-5-yl) | 0.873 | 1,150 | 0.300 | 16,700 | 0.050 | 20,000 | 1.39 | 720 |
| 73 | O 3-CONH₂-2-naphthyl) | 8.00 | 250 | 1.58 | 0 | 0.632 | 1,580 | 0.213 | 0 |
| 74 | O (2-CONH₂-1-phenyl) | 0.297 | 3,370 | 0.419 | 4,770 | 0.340 | 2,940 | 0.547 | 0 |
| 75 | OPO (CH₃)₂ | 4.33 | 1,850 | 1.05 | 7,660 | ND | ND | 0.663 | 1,510 |
| reference | -- | 0.015 | 278,00 | 0.820 | 14,600 | 0.594 | 3,370 | 0.018 | 83,300 |

TABLE 4
50% INHIBITORY CONCENTRATIONS IC$_{50}$
FOR FORMULA D

| Example No. | A | n | mICE IC$_{50}$ (μM) | CPP32 IC$_{50}$ (μM) | MCH-2 IC$_{50}$ (μM) | MCH-3 IC$_{50}$ (μM) | MCH-5 IC$_{50}$ (μM) |
|---|---|---|---|---|---|---|---|
| 78 | Cbz | 1 | 0.019 | 1.03 | 40.1 | 6.96 | >10 |
| 82 | Ac-Asp | 1 | 0.694 | 0.0014 | 6.47 | 0.145 | 2.09 |
| 85 | succinyl | 1 | 0.571 | 0.245 | 1.81 | 2.83 | 7.98 |
| 88 | Cbz-Asp | 1 | 0.096 | 0.00052 | ND | 0.084 | 1.19 |
| 91 | dihydrocinnamoyl | 1 | 0.045 | 0.780 | >10 | 32.6 | 18.7 |
| 94 | Ac | 1 | 3.07 | 3.87 | >10 | >50 | >50 |
| 100 | Benzoyl | 1 | 0.159 | 8.77 | >50 | >50 | 4.63 |
| 97 | 1-Naphthoyl | 1 | 0.010 | 2.91 | >50 | 12.3 | 1.09 |
| 103 | Cbz | 2 | 0.026 | 0.437 | 32.0 | 1.11 | 2.06 |
| reference | — | — | 0.064 | 47.0 | >10 | >10 | 2.96 |

Example 106

TABLE 5

DISSOCIATION CONSTANT Ki AND INACTIVATION RATE $k_3/K_i$ FOR EXAMPLE 106

| Enzyme | Example 106 | | Reference | |
|---|---|---|---|---|
| | $K_i$ (µM) | $k_3/K_i$ (M$^{-1}$s$^{-1}$) | $K_i$ (µM) | $k_3/K_i$ (M$^{-1}$s$^{-1}$) |
| mICE | 0.0005 | 12,000,000 | 0.015 | 214,000 |
| CPP32 | 0.012 | 960,000 | 0.820 | 12,200 |
| MCH-2 | 0.033 | 25,000 | 0.594 | 2,950 |
| MCH-5 | 0.022 | 98,000 | 0.018 | 83,300 |

INHIBITION OF APOPTOSIS USING INTERLEUKIN-1β-CONVERTING ENZYME (ICE)/CED-3 FAMILY INHIBITORS

This application is a continuation of U.S. application Ser. No. 09/737,169, filed Dec. 11, 2000; now abandoned which application is a is a continuation of U.S. application Ser. No. 08/979,909, filed Sep. 12, 1997, which issued as U.S. Pat. No. 6,200,969 on Mar. 13, 2001; which application claims the benefit of priority from U.S. Provisional App. No. 60/026,011 filed Sep. 12, 1996, now abandoned.

FIELD OF THE INVENTION

The present invention relates generally to programmed cell death and specifically to methods for expansion of hematopoietic cells, for prolonging viablility of an organ for transplantation, and maintaining viability of cell lines used in bioproduction using interleukin-1β-converting enzyme (ICE)/CED-3 family inhibitors.

BACKGROUND OF THE INVENTION

The present invention relates generally to programmed cell death and specifically to methods for expansion of hematopoietic cells, for prolonging viablility of an organ for transplantation, and maintaining viability of cell lines used in bioproduction using interleukin-1β-converting enzyme (ICE)/CED-3 family inhibitors.

Necrosis and apoptosis are two basic processes by which cells may die. In necrosis cell death usually is a result of cell injury. The cells generally swell and lyse, and the cell contents ultimately spill into the extracellular space. By contrast, apoptosis is a mode of cell death in which single cells are deleted in the midst of living tissues. Apoptosis accounts for most of the programmed cell death in tissue remodeling and for the cell loss that accompanies atrophy of adult tissues following withdrawal of endocrine and growth stimuli. In addition, apoptosis is believed to be responsible for the physiologic death of cells in the course of normal tissue turnover (i.e. tissue homeostasis) (Kerr, J. F. et al, 1972. Br. J. Cancer 26:239–257; Wyllie A. H., et al. 1980. Int. Rev. Cytol. 68:251–306).

The effector mechanisms of apoptosis are not completely understood, but ultimately, certain nuclear changes occur that appear to be caused by the activation of endogenous nucleases that cleave chromatin between nucleosomes and reduce the content of intact DNA in apoptotic cells. A number of regulators of apoptosis have been identified. Some of these are already familiar as protooncogenes and oncosuppressor genes, including c-myc, bcl-2, p53, and ras. The protooncogene products and oncosuppressor proteins are believed to control cellular susceptibility to apoptosis (Isaacs, J. T. 1994. Curr. Opin. Oncol. 6:82–89). C-myc can determine whether cells continuously proliferate or enter apoptosis, depending on the availability of critical growth factors (Bisonnette, R. P., et al. 1994. In *Apoptosis II: The Molecular Basis of Apoptosis in Disease*. Cold Spring Harbor Laboratory Press). In cultured cells, proliferation is usually observed in the presence of c-myc and growth factors, whereas apoptosis is seen when c-myc is present but growth factors are absent. Certain other oncogenes (e.g., bcl-2) rescue cells from susceptibility to apoptosis. Specifically, members of the bcl-2 gene family can act to inhibit programmed cell death (e.g., bcl-2, bcl-xL, ced-9) or promote cell death (e.g., bax, bak, bcl-xS). Additionally, members of the ICE/CED-3 family can promote cell death (e.g., ICE, CPP32, Ich-1, CED3).

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today*. 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.* 84:4572–4576 (1987); Lonnemann, G. et al., *Eur. J. Immunol.*, 19:1531–1536 (1989).

Mammalian IL-1β is synthesized as a precursor polypeptide of about 31.5 kDa (Limjuco, et al., *Proc. Natl. Acad. Sci. USA*, 83:3972, 1986). Precursor IL-1β is unable to bind to IL-1 receptors and is biologically inactive (Mosley, et al., *J. Biol. Chem.*, 262:2941, 1987). Biological activity appears dependent upon proteolytic processing which results in the conversion of the precursor 31.5 kDa form to the mature 17.5 kDa form.

Proteolytic maturation of human precursor IL-1β to mature, 17 kDa IL-1β results from cleavage between $Asp^{116}$ and $Ala^{117}$. An endoproteinase, termed Interleukin-1β Converting Enzyme (ICE), has been identified in human monocytes that is capable of cleaving the IL-1β precursor at $Asp^{116}$-$Ala^{117}$, as well as at the site $Asp^{27}$-$Gly^{28}$, and generating mature IL-1β with the appropriate amino terminus at $Ala^{117}$. The Asp at position 116 has been found to be essential for cleavage, since substitution of Ala (Kostura, et al., *Proc. Natl. Acad. Sci.*, 86:5227, 1989) or other amino acids (Howard, et al., *J. Immunol.*, 147:2964, 1991) for Asp inhibits this cleavage event.

The substrate specificity of human ICE has been defined with the use of peptides that span the cleavage site of the enzyme. Two features of peptide substrates are essential for catalytic recognition by the enzyme. First, there is a strong preference for aspartic acid adjacent to the cleavage site, in that any substitution of this residue in the IL-1β precursor and peptide substrates leads to a substantial reduction in the rate of catalysis (Kostura, et al., *Proc. Natl. Acad. Sci.*, 86:5227, 1989; Sleath, et al., *J. Biol. Chem.*, 265:14526, 1990; Howard, et al., *J. Immunol.*, 147:2964, 1991). There is an equally stringent requirement for four amino acids to the left of the cleavage site, whereas methylamine is sufficient to the right. The minimal substrate for the enzyme, AC-Tyr-Val-Ala-Asp-NH—CH$_3$, is a particularly good peptide substrate with a relative Vmax/Km similar to that of the IL-1β precursor itself (Thornberry, et al., *Nature* 356:768, 1992).

ICE is a cysteinyl proteinase by the following criteria: (1) the diazomethylketone AC-Tyr-Val-Ala-Asp-COCHN$_2$ is a potent, competitive, irreversible inhibitor of the enzyme, (2) inactivation of the enzyme by iodoacetate is competitive with substrate, and (3) the catalytically active Cys reacts selectively with [$^{14}$C] iodoacetate more than 10 times faster than do other cysteines or dithiothreitol (Thornberry, et al., *Nature*, 356:768, 1992).

ICE is related structurally and functionally to the CED-3 protease that functions as a cell death effector in the roundworm *C. elegans* (Yuan, et al., *Cell*, 75:641, 1993). ICE and CED-3 form part of a larger family of proteases (the ICE/CED-3 family) that includes CPP32, ICH-1, Mch-2, ICE$_{rel}$II, ICE$_{rel}$III, Mch-3, Mch4 and Mch-5. All of these enzymes are cysteine proteases that share significant homology at their active sites. They also share the specificity for substrate cleavage at asp-x bonds. Additionally, each of the ICE/CED-3 family members is synthesized as a pro-enzyme that is then proteolytically activated to form an active enzyme.

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases.

In various cell culture systems, it has been shown that inhibition of ICE/CED-3 family members can effectively inhibit apoptosis. For example, the compound acetyl-DEVD-aldehyde inhibited anti-Fas induced apoptosis in a T-lymphocyte cell line (Schlegel, et al., *J. Biol. Chem.*, 271:1841, 1996; Enari, et al., *Nature*, 380:723, 1996). Similarly, acetyl-YVAD-aldehyde and acetyl-YVAD-chloromethylketone blocked the death of motoneurons in vitro and in vivo (Milligan, et al., *Neuron*, 15:385, 1995). In addition, the ICE/CED-3 family inhibitor Boc-D-(benzyl) chloromethylketone as well as crmA prevented the cell death of mammary epithelial cells that occurs in the absence of extracellular matrix (Boudreau, et al., *Science*, 267:891, 1995).

It is known that control of apoptosis may have utility in treating disease. Specifically, inhibitors of the ICE/CED-3 family may have therapeutic effects. For example, it has been suggested that inhibition of ICE may be useful in the treatment of inflammatory disorders (Dolle, et al., *J. Med. Chem.*, 37:563, 1994; Thornberry, et al., *Biochemistry*, 33:3934, 1994). It is also known that inhibitors of ICE/CED-3 family members may have utility in treating degenerative diseases such as neurodegenerative diseases (e.g., Alzheimer's disease, Parkinson's disease, amyotrophic lateral sclerosis, Huntington's disease), ischemic disease of heart or central nervous system (i.e., myocardial infarction and stroke), and traumatic brain injury, as well as in alopecia, AIDS and toxin induced liver disease (Nicholson, *Nature Biotechnology* 14:297, 1996).

Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies*, C. R Clark and W. H. Moos, Eds. (Ellis Horwood, Chichester, England, 1990), pp. 92–126. These undesirable properties have hampered their development into effective drugs. The methods of this invention include either the use of conformationally constrained dipeptide mimetics or a N-substituted indolyl peptide replacement. These mimetics exhibit improved properties relative to their peptidic counterparts, for example, such as improved absorption and metabolic stability resulting in enhanced bioavailability.

SUMMARY

The present invention is directed to preventing the programmed death of cells by inhibiting the activity of proteases of the interleukin- 1β-converting enzyme (ICE)/CED-3 family. The current invention provides new methods for using ICE/CED-3 inhibitors. The present invention provides a method of using ICE/CED-3 inhibitors to expand hematopoietic cell subpopulations, enhance survival of cells, including granulocytes, in vitro, for use in cell transfusions, enhance survival of various organs, and enhance bioproduction from cells in vitro.

In a first embodiment, the invention provides a method for expanding hematopoietic cell populations or enhancing their survival, including contacting the cells with an effective amount of a reagent which suppresses the activity of at least one member of the ICE/CED-3 family thereby inhibiting the programmed cell death of immature precursors and/or mature cells and expanding and/or enhancing the survival of the cell population. Cell populations included in the method of the invention include granulocytes, monocytes, erythrocytes, lymphocytes and platelets.

In another embodiment, the invention provides a method for prolonging organ viability prior to and/or following transplantation, comprising contacting the cells of an organ with an inhibiting effective amount of a reagent which suppresses one or more ICE/CED-3 family members' activity, thereby prolonging the viability of the organ as compared to an untreated organ. An organ for transplantation can be treated with such a reagent either in vivo, ex vivo, or both. The organ may be either an intact organ, or isolated cells derived from an organ (e.g., isolated pancreatic islet cells, isolated dopaminergic neurons, blood or hematopoietic cells).

In yet another embodiment, the invention provides a method for increasing bioproduction in vitro comprising contacting bioproducing host cells with a reagent which suppresses the activity of at least one member of the ICE/CED-3 family, thereby increasing survival of such cells in vitro.

Exemplary compounds useful as ICE/CED-3 inhibitors are also included herein. Such compounds and methods of synthesis are described in their entirety in co-pending U.S. patent applications Ser. Nos. 08/710,621, filed Sep. 20, 1996 and 08/767,175, filed Dec. 16, 1996 and their respective continuations-in-part.

BRIEF DESCRIPTION OF THE DRAWINGS

FIG. 2 illustrates the activity of the compounds in Formula B regarding recombinant ICE, hCPP32, MCH2 and MCH5 enzymes.

DETAILED DESCRIPTION OF THE INVENTION

Figure 1:
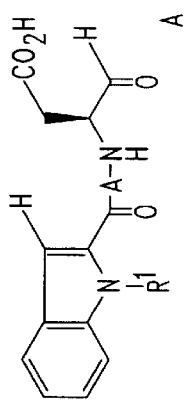
FIG. 1 sets forth the activity of the compounds in Formula A in inhibiting the activity of ICE and hCPP32 enzymes.

The present invention provides methods for the inhibition of programmed cell death, or apoptosis, by inhibition of members of the ICE/CED-3 family. This would include not only inhibitors of ICE/CED-3 enzymatic activity, but also any method which specifically prevents the expression of ICE/CED-3 family encoding genes. Thus, antisense RNA or DNA comprised of nucleotide sequences complementary to ICE/CED-3 family member genes and capable of inhibiting the transcription or translation of the relevant proteins, expression of dominant negative forms of the ICE/CED-3 proteases (e.g. mutants engineered to replace the active site cysteine with another amino acid, like serine or alanine), or antibodies which bind to ICE/CED-3 family polypeptides, are within the scope of the invention, as are small molecule inhibitors, including peptides.

Before describing the methods of the invention, compounds useful in the methods of the invention are described below:

Formula 1

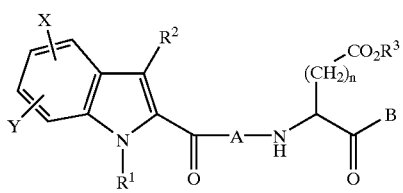

wherein:

n is 1 or 2;

$R^1$ is alkyl, cycloalkyl, (cycloalkyl)alkyl, phenyl, (substituted)phenyl, phenylalkyl, (substituted) phenylalkyl, heteroaryl, (heteroaryl)alkyl or $(CH_2)_m CO_2R^4$, wherein
m=1–4, and $R^4$ is as defined below;

$R^2$ is a hydrogen atom, chloro, alkyl, cycloalkyl, (cycloalkyl)alkyl, phenyl, (substituted)phenyl, phenylalkyl, (substituted)phenylalkyl, heteroaryl, (heteroaryl)alkyl or $(CH_2)_p CO^2R^{56}$, wherein p=0–4, and $R^1$ is as defined below;

$R^3$ is a hydrogen atom, alkyl, cycloalkyl, (cycloalkyl) alkyl, phenylalkyl, or (substituted)phenylalkyl;

$R^4$ is a hydrogen atom, alkyl, cycloalkyl, (cycloalkyl) alkyl, phenylalkyl, or (substituted)phenylalkyl;

$R^5$ is a hydrogen atom, alkyl, cycloalkyl, (cycloalkyl) alkyl, phenylalkyl, or (substituted)phenylalkyl;

A is a natural or unnatural amino acid;

B is a hydrogen atom, a deuterium atom, alkyl, cycloalkyl, (cycloalkyl)alkyl, phenyl, (substituted) phenyl, phenylalkyl, (substituted)phenylalkyl, heteroaryl, (heteroaryl)alkyl, halomethyl, $CH_2ZR^6$, $CH_2OCO(aryl)$, or $CH_2OCO(heteroaryl)$, or $CH_2OPO (R^7)R^8$, where Z is an oxygen or a sulfur atom;

$R^6$ is phenyl, substituted phenyl, phenylalkyl, (substituted phenyl)alkyl, heteroaryl or (heteroaryl) alkyl; and $R^7$ and $R^8$ are independently selected from a group consisting of alkyl, cycloalkyl, phenyl, substituted phenyl, phenylalkyl, (substituted phenyl) alkyl and (cycloalkyl) alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl; or a pharmaceutically acceptable salt thereof.

As used in the above formula 1 and in formula 3 below, the term "alkyl" means a straight or branched $C_1$ to $C_8$ carbon chain such as methyl, ethyl, tert-butyl, iso-propyl, n-octyl, and the like.

The term "cycloalkyl" means a mono-, bi-, or tricyclic ring that is either fully saturated or partially unsaturated. Examples of such a ring include cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted with one of the above cycloalkyl rings. Examples of such a group include (cyclohexyl) methyl, 3-(cyclopropyl)-n-propyl, 5-(cyclopentyl)hexyl, 6-(adamantyl)hexyl, and the like.

The term "substituted phenyl" specifies a phenyl group substituted with one or more, and preferably one or two, moieties chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N-($C_1$ to $C_6$ alkyl)carboxamide, protected N-($C_1$ to $C_6$ alkyl) carboxamide, N,N-di($C_1$ to $C_6$ alkyl)carboxamide, N-(($C_1$ to $C_6$ alkyl)sulfonyl)amino, N-(phenylsulfonyl)amino or by a substituted or unsubstituted phenyl group, such that in the latter case a biphenyl or naphthyl group results.

Examples of the term "substituted phenyl" includes a mono- or di(halo)phenyl group such as 2-, 3- or 4-chlorophenyl, 2,6-dichlorophenyl, 2,5-dichlorophenyl, 3,4-dichlorophenyl, 2-, 3- or 4-bromophenyl, 3,4-dibromophenyl, 3-chloro-4-fluorophenyl, 2-, 3- or 4-fluorophenyl and the like; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-, 3- or 4-cyanophenyl; a mono- or di(alkyl)phenyl group such as 2-, 3-, or 4-methylphenyl, 2,4-dimethylphenyl, 2-, 3- or 4-(iso-propyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(iso-propoxy)phenyl, 2-, 3- or 4-(t-butoxy)phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl, and the like.

The term "(substituted phenyl)alkyl" means one of the above substituted phenyl groups attached to one of the above-described alkyl groups. Examples of such groups include 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl, and the like.

The terms "halo" and "halogen" refer to the fluoro, chloro, bromo or iodo groups. There can be one or more halogen, which are the same or different. Preferred halogens are chloro and fluoro.

The term "aryl" refers to aromatic five and six membered carbocyclic rings. Six membered rings are preferred.

The term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. These five-membered or six-membered rings are fully unsaturated.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl) alkyl, substituted (cycloalkyl)alkyl, phenyl, substituted phenyl, phenylalkyl, and (substituted phenyl)alkyl groups. Substituents for the heteroaryl group are as heretofore defined, or as set forth below. As used in conjunction with the above substituents for heteroaryl rings, "trihalomethyl" can be trifluoromethyl, trichloromethyl, tribromomethyl or triiodomethyl, "lower alkoxy" means a $C_1$ to $C_4$ alkoxy group, similarly, "lower alkylthio" means a $C_1$ to $C_4$ alkylthio group. The term "substituted alkyl" means the above-defined alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl) alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different. The term "heteroaryl(alkyl)" denotes an alkyl group as defined above, substituted at any position by a heteroaryl group, as above defined.

Furthermore, the above optionally substituted five-membered or six-membered heterocyclic rings can optionally be fused to a aromatic 5-membered or 6-membered aryl or heteroaryl ring system. For example, the rings can be optionally fused to an aromatic 5-membered or 6-membered ring system such as a pyridine or a triazole system, and preferably to a benzene ring.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); and ammonium ion; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula 1 may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl)isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyloxycarbonyl, cyclohexanyloxycarbonyl, 1-methyl-cyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("Fmoc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyl-oxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro)phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New York, N.Y., 1984 and 1993, and J. M. Stewart and J. D. Young, "Solid Phase Peptide Synthesis," 2nd Ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acid" refers to both the naturally occurring amino acids and other non-proteinogenic α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural alpha-amino acids include hydroxylysine, citrulline, kynurenine, (4-aminophenyl)alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxy-kynurenine, 3-aminotyrosine, trifluoromethylalanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydro-proline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β-2- and 3-thienylalanine; β-2- and 3-furanylalanine; β-2-, 3- and 4-pyridylalanine; β-(benzothienyl-2- and 3-yl)alanine; β-(1- and 2-naphthyl)alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine. Any of these α-amino acids may be substituted with a methyl group at the alpha position, a halogen at any position of the aromatic residue on the α-amino side chain, or an appropriate protective group at the O, N, or S atoms of the side chain residues. Appropriate protective groups are discussed above.

Depending on the choice of solvent and other conditions known to the practitioner skilled in the art, compounds of this invention may also take the ketal or acetal form, which forms are included in the instant invention.

In addition, it should be understood that the equilibrium forms of the compounds of this invention may include tautomeric forms. All such forms of these compounds are expressly included in the present invention.

The compounds useful in the methods of the invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the group donated as "A" in Formula I or the modified aspartic or glutamic residues attached to the group denoted as "A".

In the above Formula 1 or in Formula 3 below, a group of optimal compounds occurs when n is one, more so when B is a hydrogen atom, and especially so when $R^3$ is a hydrogen atom or a t-butyl group. Of note within this group of compounds as those when A is naturally-occurring amino acid. This latter group of compounds will be referred to herein as the "4-oxobutanoic compounds".

Within this group of 4-oxobutanoic compounds is a group of optimal compounds wherein $R^1$ is a methyl group, that is, the N-methylindole compounds. One embodiment of this group of N-methylindole compounds occurs when A is an alanine, valine, leucine, phenylalanine, glycine or a proline residue. Compounds of note within each one of these groups of natural amino acid, N-methylindole compounds occur when the N-methylindole is otherwise unsubstituted, that is, wherein X, Y and $R^2$ are each a hydrogen atom, and optimally so when $R^3$ is a hydrogen atom.

Another optimal group of 4-oxobutanoic compounds consists of the N-benzylindole compounds. For example, one group of the N-benzylindole compounds occurs when A is an alanine residue. Of note within this group of alanine compounds are those in which X, Y and $R^2$ are each a hydrogen atom, and especially so where $R^3$ is a hydrogen atom.

An alternate optimal group of 4-oxobutanoic compounds occurs when the N-substituent of the indole group is a 1-butenyl group. An embodiment of this group of N-(1-butenyl)indole compounds occurs when A is a valine residue, and especially so when X, Y and $R^2$ are each a hydrogen atom. An optimal group of this latter group of compounds occurs when $R^3$ is a hydrogen atom.

Yet another group of optimal 4-oxobutanoic compounds occurs when the N-substituent of the indole ring is a 2'-acetic acid residue. An exemplary group of the N-(2'-acetic acid compounds) occurs when A is an alanine residue. An embodiment of this particular group of alanine compounds occurs when X, Y and $R^2$ are each a hydrogen atom, and especially so when $R^3$ is a hydrogen atom.

A group of the 4-oxobutanoic compounds when the indole group is substituted on the nitrogen with 3'-propionic acid residue is another example of this invention. An optimal group of such N-(propionic acid)indole compounds occurs when A is an alanine residue. Of note within this group of alanine compounds are those when X, Y and $R^2$ are each a hydrogen atom, and especially so when $R^3$ is a hydrogen atom.

Another optimal group of compounds of Formula 1 occurs wherein n is one and more so when B is a monofluoromethyl group. An embodiment of these monofluoromethyl compounds occurs when $R^3$ is a hydrogen atom or a t-butyl group, and an even more so when A is a natural amino acid. An example of these compounds wherein A is a natural amino acid occurs when A is a valine residue. This latter group of valine compounds will be referred to herein as the "4-oxo-5-(fluoropentanoic acid) compounds".

One optimal group of 4-oxo-5-(fluoropentanoic acid) compounds occurs when $R^1$ is a methyl group, in other words, the N-methylindole compounds. An exemplary group of such N-methylindole compounds occurs when $R^2$ is a methyl group and X and Y are each a hydrogen atom, and especially so when $R^3$ is a hydrogen atom. Another exemplary group of such N-methylindole compounds occurs when $R^2$ is a chloro atom and X and Y are each a hydrogen atom, and especially so when $R^3$ is a hydrogen atom. A third exemplary group of N-methylindole compounds occurs when $R^2$ is a chloro group, X is a 5-fluoro group, and Y is a hydrogen atom, and especially so when $R^3$ is a hydrogen atom.

Another optimal group of 4-oxo-5-(fluoro-pentanoic acid) compounds is composed of N-(3'-phenylprop-1-yl)indole compounds. A group of note within this latter class of compounds occurs when $R^2$, X and Y are each a hydrogen atom, and especially so wherein $R^3$ is a hydrogen atom.

A third optimal group of 4-oxo-5-(fluoro-pentanoic acid) compounds has an N-(carboxymethyl or protected carboxymethyl)indole moiety. An embodiment of this group occurs wherein $R^2$, X and Y are each a hydrogen atom, and especially so wherein $R^3$ is a hydrogen atom and the nitrogen atom of the indole ring is substituted with a carboxymethyl group.

Another optimal class of compounds of Formula 1 occurs when n is one and B is a (2,6-dichlorobenzyloxy)-methyl group and especially so when $R^3$ is a hydrogen atom or a t-butyl group, and when A is a natural amino acid. An example of such a compounds occurs when $R^1$ is a methyl group and especially so when $R^2$ is a methyl group.

The compounds of Formula 1 may be synthesized using conventional techniques as discussed below. Advantageously, these compounds are conveniently synthesized from readily available starting materials.

One synthetic route for synthesizing compounds is set forth in the following Scheme 1:

SCHEME I

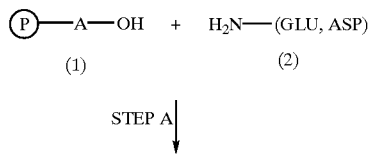

-continued

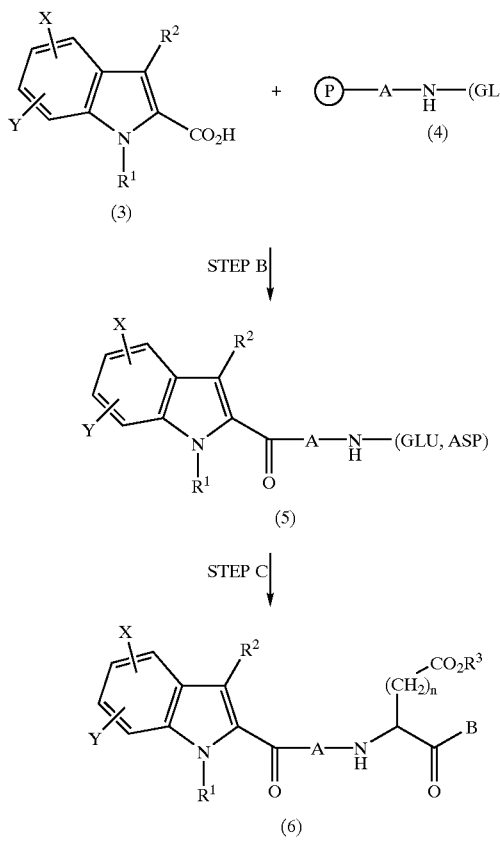

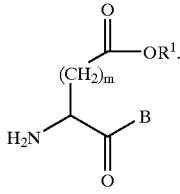

FORMULA 2d

In the above Scheme I, ⓟ stands for an amino protecting group and (A) stands for a natural or unnatural amino acid, as discussed above.

The modified aspartic or glutamic acids of Formula 2a–d can be prepared by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference.

The coupling reactions carried out under Step A are performed in the presence of a standard peptide coupling agent such as the combination of the combination of dicyclohexylcarbodiimide(DCC) and 1-hydroxy-benzotriazole(HOBt), as well as the BOP (benzotriazolyloxy-trio-(dimethylamino)phosphonium hexafluorophosphate) reagent, pyBOP (benzotriazolyloxy-tris(N-pyrolidinyl)phosphoniumhexafluorophosphate), HBTU (O-benzotriazolyly-tetramethylisouronium-hexafluorophosphate), and EEDQ (1-ethyloxycarbonyl-2-ethyloxy-1,2-dihydroquinoline) reagents, the combination of 1-ethyl(3,3'-dimethyl-1'-aminopropyl)carbodiimide (EDAC) and HOBt, and the like, as discussed in J. Jones, "Amino Acid and Peptide Synthesis," Steven G. Davis ed., Oxford University Press, Oxford, pp. 25–41 (1992); M. Bodanzky, "Principles of Peptide Synthesis," Hafner et al. ed., Springer-Verlag, Berlin Heidelberg, pp. 9–52 and pp. 202–251 (1984); M. Bodanzky, "Peptide Chemistry, A Practical Textbook," Springer-Verlag, Berlin Heidelberg, pp. 55–73 and pp. 129–180; and Stewart and Young, "Solid Phase Peptide Synthesis," Pierce Chemical Company, (1984), all of which are herein incorporated by reference. The amino protecting group is then removed and the resulting amine is coupled to the 2-(carboxy)indole of (3) (Step B). Again, this coupling reaction uses the standard peptide coupling reactions mentioned above. The indole ring of (3) can be substituted before the reaction in Step B or afterwards. The synthesis and substitution reactions of such an indole ring is well known, as is described, for example, in Brown, R. T. and Joule, J. A. in "Heterocyclic chemistry (ed. P. G. Sammes) (Vol. 4 of Comprehensive Organic Chemistry, ed. D. Barton and W. D. Ollis), (1979), Pergamon Press, Oxford; Houlihan, W. J., (ed.) in "Indoles (The Chemistry of Heterocyclic Compounds [ed. A. Weissburger and E. C. Taylor], Vol. 25, Parts 1–3), Wiley Interscience, New York (1972); and Saxton, J. E. (ed.) in "Indoles (The Chemistry of Heterocyclic Compounds)," [ed. A. Weissburger and E. C. Taylor], Vol. 25, Part 4), Wiley Interscience, New York, (1979); all of which are incorporated herewith by reference.

In the above Scheme I, Formula (2), that is H2N(Glu, Asp), is a modified aspartic or glutamic acid residue of Formulas 2a through 2d:

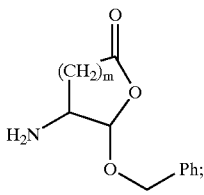

FORMULA 2a

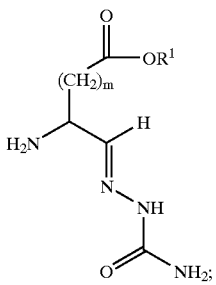

FORMULA 2b

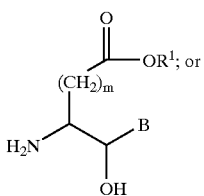

FORMULA 2c

In the case where the coupling reaction was carried out with the amino alcohol of Formula 2c, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylamine); and Dess-Martin oxidation (Dess-Martin periodinane, t-butanol, and methylene chloride.) The protecting groups contained in substructures of the Formula 2a–d and A are removed by methods well known in the art. These reactions and removal of some or all of the protecting groups are involved in Step C in the above Scheme.

The compounds of Formula 3, below, are also useful in the methods of the invention:

FORMULA 3

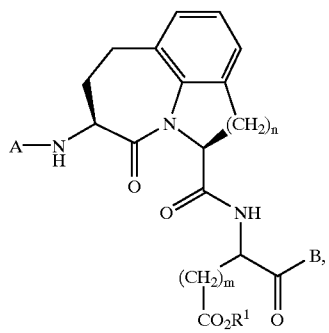

wherein:

n is 1 or 2;

m is 1 or 2;

A is $R^2CO—$, $R^3—O—CO—$, or $R^4SO_2—$;

a group of the formula:

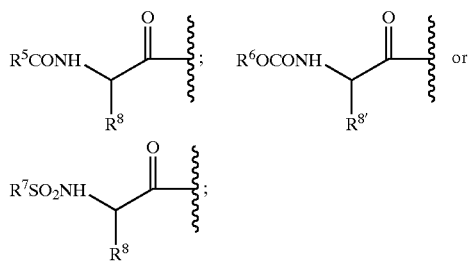

further wherein:

$R^1$ is a hydrogen atom, alkyl or phenylalkyl;

$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^3$ is alkyl, cycloalkyl, (cycloalkyl)alkyl, phenylalkyl, or (substituted phenyl)alkyl;

$R^4$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^5$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^6$ is alkyl, cycloalkyl, (cycloalkyl)alkyl, phenylalkyl, or (substituted phenyl)alkyl;

$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^8$ is an amino acid side chain chosen from the group consisting of natural and unnatural amino acids;

B is a hydrogen atom, a deuterium atom, alkyl, cycloalkyl, (cycloalkyl)alkyl, phenyl, phenylalkyl, (substituted)phenyl, (substituted)phenylalkyl, heteroaryl, (heteroaryl)alkyl, or halomethyl;

a group of the formula

wherein $R^9$ is phenyl, phenylalkyl, substituted phenyl, (substituted phenyl)alkyl, heteroaryl, or (heteroaryl)alkyl; and X is an oxygen or a sulfur atom;

a group of the formula:

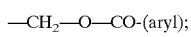

a group of the formula:

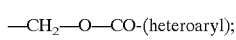

a group of the formula:

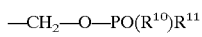

wherein $R^{10}$ and $R^{11}$ are independently selected from a group consisting of alkyl, cycloalkyl, phenyl, substituted phenyl, phenylalkyl and (substituted phenyl) alkyl; and the pharmaceutically-acceptable salts thereof.

The compounds of Formula 3 may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The compounds of Formulas 1 and 3 of this invention may be synthesized using conventional techniques. Advantageously, these compounds are conveniently synthesized from readily available starting materials.

Thus, compounds of Formula 3 can be synthesized in general by combining a tricyclic nucleus set forth below in Formula 4:

FORMULA 4

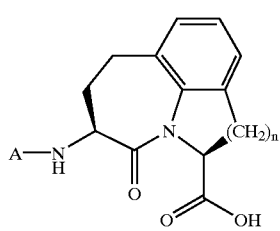

with the modified aspartic and glutamic acid residues of Formula 5a–d:

FORMULA 5a

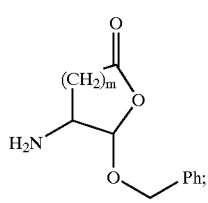

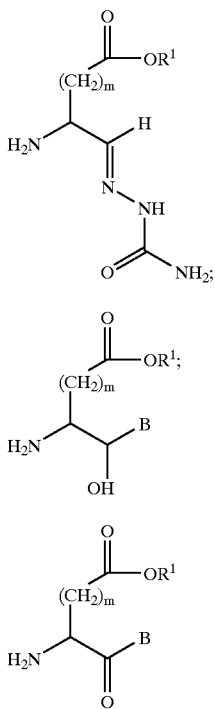

FORMULA 5b

FORMULA 5c

FORMULA 5d in the presence of a standard peptide coupling agents such as dicyclohexylcarbodiimide(DCC)-1-hydroxybenzotriazole (HOBt), BOP reagent, pyBOP, TBTU, EEDQ, 1-ethyl(3,3'-dimethyl-1'-aminopropyl)carbodiimde(EDAC)HOBt, and the like, as discussed in J. Jones, "Amino Acid and Peptide Synthesis," Steven G. Davis ed., Oxford University Press, Oxford, pp. 25–41 (1992), herein incorporated by reference. In the above formula, A is an amino protecting group. The amino protecting group is then removed and the resulting amine is combined with the substituted acyl group of Formula 6:

$R^C$—CO—X  FORMULA 6 or the sulfonyl group of Formula 7:

$R^4SO_2$—X.  FORMULA 7

In the above formulas, $R^1$ is as defined above, and $R^C$ is $R^2$, $R^3$—O, $R^4$, or any of the side chains containing $R^8$ as defined for group A in Formula 3. Of course, such moieties would have any hydroxy, carboxy or amino groups in the protected form so as not to interfere with the coupling reaction (Formula 5a–d), the acylation reaction (Formula 4) or the sulfonation reaction (Formula 7). X in the above Formulas represents a facile leaving group for the acylation or sulfonation reactions.

In the case where the coupling reaction was carried out with the amino alcohol of Formula 5c, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylmine; and Dess-Martin oxidation (Dess-Martin periodinane, t-butanol, and methylene chloride.) The protecting groups contained in substructures of the Fomula 5a–d and A are removed by methods well known in the art.

The tricyclic nucleus of Formula 3 is synthesized by methods known in the art. For example, see D. S. Karanewsky, U.S. Pat. No. 5,504,080 issued Apr. 2, 1996; J. A. Robl et al., *Tetrahedron Letters*, 36:1593–1596 (1995); and S. De Lombaert et al., *Tetrahedron Letters*, 35:7513–7516 (1994), all of which are incorporated herein by reference.

The modified aspartic or glutamic acid for Formula 5a–d can be elaborated by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference.

The acyl group of Formula 6 and the corresponding $R^4SO_2$ groups are also synthesized by methods well known in the art. See, for example, U.S. Pat. No. 5,504,080, issued Apr. 2, 1996, herein incorporated by reference. While this group can be elaborated once bonded to the tricyclic nucleus, it is preferable that it be intact before being attached to the nucleus.

Once the side chains of Formula 5 and Formula 6 or Formula 7 are bonded to the tricyclic nucleus of Formula 3, one skilled in the art would usually remove any amino, hydroxy, or carboxy-protecting groups to enhance the activity of the synthesized molecule.

Methods for Inhibiting Apoptosis

The present invention provides methods for the inhibition of programmed cell death, or apoptosis, by inhibition of members of the ICE/CED-3 family. The invention provides new uses for not only inhibitors of ICE/CED-3 enzymatic activity, but also any method which specifically prevents the expression of ICE/CED-3 family encoding genes. Thus, antisense RNA or DNA comprised of nucleotide sequences complementary to ICE/CED-3 family member genes and capable of inhibiting the transcription or translation of the relevant proteins, expression of dominant negative forms of the ICE/CED-3 proteases (e.g. mutants engineered to replace the active site cysteine with another amino acid, like serine or alanine), or antibodies which bind to ICE/CED-3 family polypeptides, are within the scope of the invention, as are small molecule inhibitors, including peptides and especially the compounds presented herein.

In a first aspect, the invention provides a method for expanding hematopoietic and blood cell populations or prolonging survival of such populations, including contacting the cells with an effective amount of a reagent which suppresses the activity of one or more ICE/CED-3 family members, inhibiting the programmed cell death of immature precursors and/or mature cells, thereby expanding the cell population and/or enhancing the survival of the cell population. The term "expansion" or "expanding" as used herein means increasing the number of cells of a pre-existing cell population. The term "survival" refers to maintaining viability of cells, typically ex vivo, however the term is meant to include in vivo as well. Survival may be from a few hours to several days or longer.

The method includes contacting the desired cells with an inhibiting effective amount of a reagent which suppresses ICE/CED-3 activity. The term "contacting" as used herein means exposing the cells to the ICE/CED-3 family inhibitor(s) such that the inhibitor(s) can effectively inhibit ICE/CED-3 activity thereby inhibiting apoptosis in the cells and allowing the cells to proliferate and accumulate. The term "inhibiting effective amount" means that amount of ICE/CED-3 inhibitor that effectively blocks ICE/CED-3 enzymatic activity in intact target cells. It will be apparent that one or more ICE/CED-3 family inhibitors can be used simultaneously in the method of the invention. In a preferred embodiment, contacting may be in vivo dosing of ICE/CED-3 inhibitor(s) to a subject in need of expansion of a cell population, such as a subject recently having undergone chemotherapy. Examples of such reagents are commonly known in the art, including Cbz-ValAlaAsp-CH$_2$F, Cbz-ValAlaAsp-CH$_2$OCO (2,6-diCl—C$_6$H$_4$), Cbz-ValAlaAsp-CH$_2$F, methyl ester, Ac-AspValAlaAsp-CH$_2$F. Exemplary compounds include Formula 1 and Formula 3 as described supra.

Detection of ICE/CED-3 activity is by standard methods, such as an enzymatic assay to measure the fluorescence generated by enzymatic cleavage of aminomethylcoumarin (AMC) conjugated to a relevant peptide (e.g., Ac-DEVD-amc). Such assays are standard in the art (Armstrong et al., J. Biol. Chem. 271:16850, 1996); Fernandes-Alnemri, et al., Cancer Res., 55:6045, 1995). In addition, the inhibition of ICE activity can be measured by a bioassay for IL-1β. ICE/CED-3 activity is preferably suppressed by the ICE/CED-3 family inhibitor(s) by at least about 75%, and preferably by about 90%.

The "cells" or "cell population" include precursor cells (e.g., pluripotent stem cells) and/or differentiated, mature cells. Examples of cells expanded and/or whose survival is enhanced by the method of the invention include but are not limited to granulocytes (e.g., neutrophils), monocytes, erythrocytes, lymphocytes and platelets.

Success of hematopoiesis can also be detected by measuring hematocrit, white blood cell count, incorporation of tritiated thymidine into bone marrow DNA, spleen weight, number of burst-forming units-erythroid or number of colony-forming units (erythroid, granulocyte/macrophage and megakaryocyte forming lineages) from spleen or bone marrow for example.

Hematopoietic disorders can occur as a result of primary disease or as a consequence of therapy for another disease. For example, a serious side effect of radiation or chemotherapy is myelosuppression. Pancytopenia can be observed following bone marrow transplantation and profound leukopenia is often observed in AIDS. Patients with chronic renal failure undergoing dialysis often have anemia. AIDS patients treated with AZT, cancer patients treated with platinum, and anemic patients with rheumatoid arthritis often require transfusions because of anemia and leukopenia. Various hematopoietic growth factors, such as erythropoietin, granulocyte or granulocyte-macrophage colony stimulating factors, or cytokines such as interleukin-1 are known to stimulate hematopoiesis and have been used to treat these conditions. However, treatment times are generally on the order of weeks, and especially for the case of neutropenias, patients are at risk for opportunistic infections. These therapies are usually quite expensive, as they are recombinantly produced proteins. Thus, it would be advantageous to be able to administer a small molecule, e.g., ICE/CED-3 inhibitor, either alone or in combination with a growth factor to speed hematopoietic recovery. Various cytokines including hematopoietic growth factors, are known to both increase proliferation and inhibit apoptosis in target cells (Koury and. Bondurant, Science, 248:378, 1990; Muta and Krantz, J. Cell Physiol., 156:264, 1993). However, those agents act upstream of the apoptotic cellular machinery, affecting that machinery only indirectly. The present invention provides methods to enhance cell expansion by directly inhibiting the apoptotic machinery. The combination therapy comprising administering a hematopoietic growth factor together with the methods of the present invention is a preferable embodiment.

The method of the invention is useful for restoring normal hematopoiesis in individuals in need of reconstitution of their bone marrow. The pluripotent stem cell has the unique capacity for self-renewal and the potential for growth and differentiation along granulocytic, monocytic, erythroid, megakaryocytic, and lymphoid lineages.

As one skilled in the art will also appreciate, stem cells can be directed to differentiation as a lymphoid, myeloid, or erythroid-lineage population by incubation with the appropriate hematopoietic growth factor or combination of growth factors. Therefore, the method of the invention further includes contacting the cells with a suitable hematopoietic growth factor, in addition to the ICE/CED-3 inhibitor. As used herein, the term "a suitable hematopoietic growth factor" means one or more hematopoietic growth factors known in the art to direct a progenitor stem cell to the desired lymphoid, granulocytic, monocytic, megakaryocytic, myeloid, or erythroid-lineage cell population. Various growth factors function both by promoting proliferation of cells and by inhibiting apoptosis; both of these functions promote the accumulation of cells. Certain hematopoietic growth factors, including G-CSF, GM-CSF, and erythropoietin are examples of such growth factors that can inhibit programmed cell death of their respective target cells, as well as stimulate proliferation of those cells. These factors have proven clinically useful in promoting the repopulation of granulocytes (e.g., neutrophils), monocytes and erythrocytes in patients. G-CSF and GM-CSF are often used in patients following chemotherapy or radiation, and erythropoietin is commonly used in patients undergoing kidney dialysis. Other representative growth factors known in the art that can be used for these purposes are IL-1, IL-6, stem cell factor, and IL-3. Other growth factors for stimulating proliferation of hematopoietic lineages will be known to those of skill in the art (see, for example, Harrison's Principles of Internal Medicine, Isselbacher, et al., eds., pp 1714–1717, McGraw Hill, 1994, incorporated herein by reference).

Apoptosis inhibitors, such as ICE/CED-3 inhibitors, can extend survival of blood cell precursors in the bone marrow as well as extend survival of the mature blood cells themselves. Regarding extension of survival of mature blood cells, this may be particularly valuable for repopulation of granulocytes following chemotherapy and/or radiation (with or without bone marrow transplant). Mature granulocytes (specifically neutrophils) last for only 24 hours in the bloodstream after which they die by apoptosis. ICE/CED-3 inhibitors that block apoptosis and increase neutrophil survival would increase the rate at which a patient normalized his white blood cell count. Inhibition of apoptosis in precursor cells which ultimately give rise to the mature cell populations would be synergistic with effects on mature cells.

The invention provides methods to preserve the viability of neutrophils/granulocytes ex vivo for subsequent transfusion into recipients in need of additional granulocytes. The life-span of granulocytes removed from donors is limited and thus it is difficult to obtain supplies of functional granulocytes for transfusion.

The reagents of the present invention are "ICE/CED-3 inhibitors" in that they inhibit the catalytic activity of members of the ICE/CED-3 family in a reversible or an irreversible manner. The term "irreversible" as used herein means the formation of a covalent bond between the ICE/CED-3 family member and the inhibitor. It is possible to convert a reversible inhibitor to an irreversible inhibitor by incorporating an irreversible "warhead" into what would otherwise be a reversible inhibitor.

The reversibility of ICE/CED-3 inhibition is generally a function of the electronegative group in the molecule. When the electronegative group is a diazoalkyl ketone, the inhibition of ICE activity is irreversible and the compound is an irreversible inhibitor. When the electronegative group is an aldehyde, the inhibition of ICE is reversible and the inhibitor is a reversible inhibitor.

A compound of the invention preferably has an aldehyde, a diazoalkyl ketone, a haloalkyl ketone, or acyloxymethyl ketone. As used herein in reference to an electronegative group, "alkyl" refers to linear or branched chain radicals having 1–3 carbon atoms, which may be optionally substituted. Representative alkyl groups include methyl, ethyl, propyl and the like. Optionally, the electronegative group is an aldehyde, fluoromethyl ($CH_2F$) ketone, or acyloxylmethyl ketone.

The compounds of the present invention are made by techniques generally corresponding to methods known and readily apparent to those of skill in the art. See, e.g., Kettner, et al., *Arch, Biochem, Biophys*., 162:56, 1974; U.S. Pat. Nos. 4,582,821; 4,644,055; Kettner, et al. *Arch, Biochem, Biophys*, 165:739, 1974; Dakin and West, *J. Biol. Chem.*, 78:91, 1928; Rasnick, D., *Anal. Biochem.*, 149:461, 1985; Revesz, L., *Tetrahedron Lett.*, 35:9693, 1994. Exemplary indolyl dipeptide and tricyclic compounds are provided herein.

Compounds having a non-fluoro, haloalkyl ketone electronegative leaving group are preferably synthesized in accordance with the Kettner procedure. An N-blocked amino acid or peptide is reacted with N-methylmorpholine and an alkyl, non-fluoro haloformate to generate a peptide-acid anhydride. The anhydride is then reacted with a diazoalkane in an inert, aprotonic solvent to form a peptide-diazomethane ketone. The diazomethane ketone is then reacted with an anhydrous solution of HCl, HBr or HI to produce the desired N-blocked, C-terminal haloalkyl ketone peptide or amino acid.

Compounds having a fluoromethyl electronegative leaving group are preferably synthesized by the Revesz procedure. An N-blocked peptide or amino acid is reacted with t-butyl (3-amino-4-hydroxy-5-fluoro) pentanoate in the presence of a standard peptide coupling agent such as dicyclohexylcarbodiimide-hydroxy-benztriazole. The resulting product is oxidized to the corresponding ketone by either Severn or Dess-Martin oxidation. Finally, deprotection of the t-butylester with trifluoroacetic acid gives the corresponding carboxylic acid.

Compounds having a fluoroalkyl ketone electronegative leaving group can be extended in the N-terminus direction by removing the N-terminal blocking group and coupling the deprotected compound with other protected amino acids. Bodanszky, *The Practice of Peptide Synthesis*, Springer-Verlag, Berlin, 1984. Alternatively, deprotected compounds are acetylated to yield compounds having an N-terminal acetyl protecting group. Stewart, et al., *Solid Phase Peptide Synthesis*, Pierce Chemical Co., Rockford, Ill., 1984.

In another embodiment, the invention provides a method for prolonging organ viability comprising contacting the cells of an organ for transplantation with an inhibiting effective amount of a reagent which suppresses interleukin-1β-converting enzyme (ICE)/CED-3 activity, thereby prolonging the viability of the organ as compared to an untreated organ. The term "organ" is meant to include intact multi-cellular organs such as kidney, liver, or heart; cell suspensions derived from multi-cellular organs (e.g., pancreatic islet cells in dopaminergic neurons); as well as suspensions of blood cells or hematopoietic precursor cells. Preferably, an organ is treated ex vivo in order to preserve the organ for transplantation. The term "prolonging" means that an organ for transplantation is preserved by treatment using the method of the invention as compared to a similar organ that has not been treated with an ICE/CED-3 inhibitor. While not wanting to be bound by a particular theory, it is believed that contacting the cells of an organ for transplantation with an ICE/CED-3 inhibitor, inhibits programmed cell death, thereby preserving the organ and prolonging viability.

The method of the invention includes treatment of the recipient prior and subsequent to transplantation with genetically altered or ICE/CED-3 inhibitor-bathed donor organs to inhibit apoptosis of donor organ cells, and optionally, an immunosuppressive agent.

The present invention includes the ex vivo expansion or survival of hematopoietic cells which is useful for a variety of clinical uses including gene therapy, augmentation of bone marrow transplantation, and the replacement of bone marrow transplantation. Therefore, the use of an inhibitor of the apoptosis machinery, such as an ICE/CED-3 family inhibitor, to promote the ex vivo expansion and/or survival of populations of granulocytes, erythrocytes, lymphocytes and or platelet constitutes a useful method. For example, one can add the ICE/CED-3 inhibitor(s) to a tissue culture of cells isolated from a subject, or by transfecting the cells with an expression vector containing an operable ICE/CED-3 inhibitor-encoding polynucleotide, e.g., antisense, to such cells.

The method of the invention has therapeutic utility. For instance, a suspension of pluripotent hematopoietic stem cells (HSC) obtained by standard methods in the art, can be treated by the method of the invention and can be used for performing hematopoietic reconstitution of a recipient. As an ex vivo treatment for example, enriched pluripotent stem cells derived from the recipient (autologous reconstitution) or derived from an individual other than the recipient (non-autologous reconstitution) can be expanded and used in the treatment or prevention of various diseases or disorders such as anemias, malignancies, autoimmune disorders, and various immune dysfunctions and deficiencies, as well as recipients whose hematopoietic cellular repertoire has been depleted, such as recipients treated with various chemotherapeutic or radiologic agents, or recipients with AIDS. Other therapeutic uses of the compositions of the invention are well known to those of skill in the art. Treatment of the transplanted cells can be both ex vivo, and following transplantation, in vivo.

An example of the way in which the invention may be applied to non-autologous donor organs for human recipients is as follows: beginning one week prior to the transplantation, the recipient may be dosed with cyclophosphamide to reduce the potential for evoked immunological responses. An immunosuppressive dose of cyclosporine or FK506 may be started shortly (1–3 days) before transplantation to enhance graft acceptance. Immediately prior to transplantation, the donor may be dosed with an ICE/CED-3 inhibitor, prior to organ removal. Upon removal prior to transplantation, the donor organ is flushed with a solution containing at least one ICE/CED-3 inhibitor, e.g., a peptide fluoroalkyl ketone. Following transplantation by standard surgical techniques, the patient is typically maintained on routine immunosuppression using cyclosporine or FK506, cyclophosphamide,. and steroids and optionally, the ICE/CED-3 inhibitor(s). Based on clinical signs and symptoms related to immune responsiveness, various of the immunosuppressants are reduced in dosage.

An immunosuppressive agent used during transplantation is an agent such as Cyclosporine A (CsA), however other agents which cause immune suppression, such as rapamycin, desoxyspergualine, and FK506 or functional equivalents of these compounds, may also be utilized. CsA is preferably administered by injection at an immunosuppressive dose. The duration of CsA treatment may range from about 2 to about 20 days.

For enhancing organ survival prior to transplantation, the ICE/CED-3 family inhibitor may be administered by addition to the fluid used to perfuse the excised organ. If the ICE/CED-3 inhibitor is also to be administered to the donor prior to excision of the organ, the ICE/CED-3 inhibitor(s) are administered by any suitable means, including parenteral, subcutaneous, intrapulmonary, and intranasal administration. Parenteral infusions include intramuscular, intravenous, intraarterial, or intraperitoneal administration.

It is understood that any organ from any species can be transplanted. The method of the invention is useful for preserving organs to be used for same species transplants such as human recipients and other human donors (allografts and autologous grafts) or to human recipients from other species such as sheep, pigs, or non-human primates (xenografts), for example. Such tissues for transplant include, but are not limited to, heart, liver, kidney, lung, pancreas, pancreatic islets, brain tissue, cornea, bone, intestine, skin, and hematopoietic cells. The human is the preferred recipient.

In order to determine the amount of ICE/CED-3 inhibitor to administer to the donor, e.g., pig, and the amount of ICE/CED-3 inhibitor with which to treat the organ to be transplanted, a compound is administered so that its concentration in the vasculature is at least as high as that necessary for inhibition of apoptosis in a cell culture model. A variety of cell culture models are known in the art (e.g., Armstrong et al., supra; Schlegel, et al., supra; Boudreau, et al., supra). The donor organ, and optionally the donor, is then dosed with an ICE inhibitor in order to reduce apoptosis to as much as less than about 10% of the normal apoptosis observed in the organ from the donor. Therefore, as used herein, the term "apoptosis-inhibiting" amount refers to that amount of ICE inhibitor that inhibits ICE activity and/or apoptosis by about 75%, and preferably by about 90%.

Method for Enhancing Bioproduction

In yet another embodiment, the invention provides a method for increasing survival of cells cultured in vitro for utilities other than transplantation. For example, inhibition of programmed cell death is of use in enhancing bioproduction processes. For example, in production of recombinant proteins, yields may be limited by apoptotic cell death of cultured host cells. Therefore, treatment of host cells with ICE/CED-3 inhibitors, or using host cells which express antisense RNA or DNA sequences complementary to ICE/CED-3 and capable of inhibiting the transcription or translation of ICE/CED-3 family members or that express genes encoding ICE/CED-3 family inhibitors, would enhance bioproduction by allowing cells to survive longer and produce and/or secrete a desired product longer, thus resulting in a greater yield of product. The ability to prevent programmed cell death may allow cells to live independent of normally required growth factors, reducing the cost of media supplements.

In order to demonstrate utility in bioproduction, a cell line that naturally produces a useful product (e.g., a cytokine) or a cell line genetically engineered to express a useful product (e.g., COS or CHO cells stably expressing recombinant human erythropoieten, growth hormone or G-CSF) is contacted with the ICE/CED-3 inhibitor during fermentation. Effectiveness of the ICE/CED-3 inhibitor on bioproduction can be measured in several ways: 1) determining the percentage of apoptotic cells in the culture at different time points; 2) determining the useful lifespan of the culture with regard to production of the desired product; 3) measuring the yield of product per gram of cells or per volume of culture; 4) measuring final purity of the product.

Methods for increasing the efficiency or overall productivity of bioproduction are useful because they reduce costs of producing a natural or recombinant product. Mammalian cell fermentation is limited by decreasing cell viability with time. Cell death during fermentation has been shown to be apoptotic, thus inhibitors of apoptosis will increase cell viability during bioproduction. Growth media used for bioproduction are often serum-free supplemented with growth factors to enhance cell viability. Supplementation with ICE/CED-3 ihhibitors of the present invention is designed to replace or agument such additives.

Pharmaceutical Compositions

Pharmaceutical compositions of this invention comprise any of the compounds of the present invention, and pharmaceutically acceptable salts thereof, with any pharmaceutically acceptable carrier, adjuvant or vehicle (hereinafter collectively referred to as "pharmaceutically-acceptable carriers"). Pharmaceutically acceptable carriers, adjuvants and vehicles that may be used in the pharmaceutical compositions of this invention include, but are not limited to, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat, and the like.

The pharmaceutical compositions of this invention may be administered orally, parenterally, by inhalation spray, topically, rectally, nasally, buccally, vaginally or by an implanted reservoir. Oral and parenteral administration are preferred. The term "parenteral" as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds of this invention may be used in combination with either conventional anti-inflammatory agents or with matrix metalloprotease inhibitors, lipoxygenase inhibitors and antagonists of cytokines other than IL-1β.

When the compounds of this invention are administered in combination therapies with other agents, they may be administered sequentially or concurrently to the patient. Alternatively, pharmaceutical compositions according to this invention may be comprised of a combination of a compound of Formula 1 or 3 or other ICE inhibitors as described herein, and another therapeutic or prophylactic agent mentioned above.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). As a consequence of their ability to inhibit apoptosis, the present pharmaceutical compositions are also useful for the repopulation of hematopoietic cells of a patient following chemotherapy. Methods of administering an effective amount of the above-described pharmaceutical compositions to mammals, also referred to herein as patients, in need of such treatment (that is, those suffering from inflammatory diseases, autoimmune diseases, neurodegenerative diseases and for the repopulation of hematopoietic cells in cancer patients who have undergone chemotherapy) are another aspect of the instant invention. Finally, as a further consequence of their ability to inhibit apoptosis, the instant pharmaceutical compositions may be used in a method to prolong the viability of organs to be used in transplantations.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune garrritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative described in this invention may also be used to promote wound healing. Target diseases associated with harmful, apoptosis, in other words, those associated with ischemic injury, includes myocardial infarction, stroke, and ischemic kidney disease.

The term "effective amount" refers to dosage levels of the order of from about 0.05 milligrams to about 140 milligrams per kilogram of body weight per day for use in the treatment of the above-indicated conditions (typically about 2.5 milligrams to about 7 grams per patient per day). For example, inflammation may be effectively treated by the administration of from about 0.01 to 50 milligrams of the compound per kilogram of body weight per day (about 0.5 milligrams to about 3.5 grams per patient per day).

The amount of the compounds of Formula 1, 3, or other ICE/ced-3 inhibitors that may be combined with the carrier materials to produce a single dosage form will vary depending upon the host treated and the particular mode of administration. For example, a formulation intended for the oral administration of humans may contain from 0.5 milligrams to 5 grams of a compound of Formula 1 combined with an appropriate and convenient amount of a pharmaceutically-acceptable carrier which may vary from about 5 to about 95 percent of the total composition. Dosage unit forms will generally contain between from about 1 milligram to about 500 milligrams of an active compound of Formula 1, 3, or other ICE/ced-3 inhibitors.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing prevention or therapy.

Although this invention focuses on the use of the compounds disclosed herein for inhibiting ICE/CED-3 proteases and for preventing apoptosis, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cystine protease inhibitors will be evident to those of ordinary skill in the art.

The following examples are intended to illustrate, but not limit the invention. While they are typical of those that might be used, other procedures known to those skilled in the art may alternatively be used.

In the following Examples, proton NMR spectra were obtained at 300 MHZ; chemical shifts are quoted downfield from internal tetramethylsilane.

EXAMPLE 1

Assays for Inhibition of ICE/ced-3 Protease Family Activity

A. Determination of $IC_{50}$ Values

Fluorescence enzyme assays detecting the activity of the compounds of Formula 1 utilizing the recombinant ICE and cpp32 enzymes were performed essentially according to Thornberry et al. (*Nature*, 356:768:774 (1992)) and Nicholson et al. (*Nature*, 376:37–43 (1995)) respectively, (herein incorporated by reference) in 96 well microtiter plates. The substrate for these assays was Acetyl-Tyr-Val-Ala-Asp-amino-4-methylcoumarin (AMC) for the ICE assay and Acetyl-Asp-Glu-Val-Asp-amino-4-methylcoumarin for the cpp32 and Mch5 assay. Enzyme reactions were run in ICE buffer (25 mM HEPES, 1 mM EDTA, 0.1% CHAPS, 10% sucrose, pH 7.5) containing 2 mM DTT at room temperature in duplicate. The assays were performed by mixing the following components:

- 50 µl of either ICE, Mch2, Mch5 or cpp32 (18.8, 38, 8.1 and 0.153 nM concentrations, respectively) or Mch3 (1 unit) enzyme in ICE buffer containing either 8.0 (ICE, Mch2, Mch3, cpp32) or 20 (Mch5) mM DTT;
- 50 µl of either the compound of Formula 1 or ICE buffer (control); and
- 100 µl of 20 µM substrate.

Figure 4:
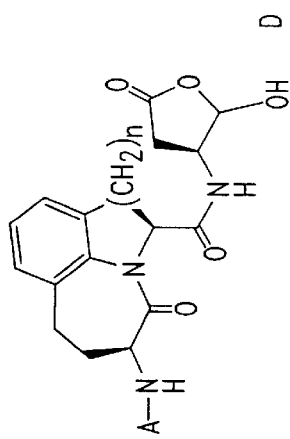
FIG. 4 sets forth the activity of compounds in Formula D in inhibiting the activity of ICE, CPP32, MCH2, MCH3 and MCH5 enzymes.

The enzyme and the compound of Formula 1 to be assayed were preincubated in the microtitre plate wells for 30 minutes at room temperature prior to the addition of substrate to initiate the reaction. Fluorescent AMC product formation was monitored for one hour at room temperature by measuring the fluorescence emission at 460 nm using an excitation wavelength of 360 nm. The fluorescence change in duplicate (control) wells were averaged and the mean values were plotted as a function of inhibitor concentration to determine the inhibitor concentration producing 50% inhibition ($IC_{50}$). The results are set forth in Tables 1 and 4 (FIGS. 1 and 4).

The reference compound for this assay was Cbz-ValAlaAsp-H and the values are denoted in Tables 1 and 4 as "Reference".

B. Determination of the Dissociation Constant $K_i$ and Irreversible Rate Constant $k_3$ for Irreversible Inhibitors For the irreversible inhibition of a ICE/ced-3 Family Protease enzyme with a competitive irreversible inhibitor; using the model represented by the following formulas:

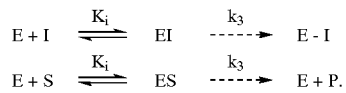

The product formation at time t may be expressed as:

$$[P]_t = [E]^T \left(\frac{[S]K_i}{[I]K_s}\right)\left(\frac{k_s}{k_3}\right)\left[1 - e^{-k_3 t / \left(1 + \frac{K_i}{[I]}\left(1 + \frac{[S]}{K_s}\right)\right)}\right] \qquad \text{Equation 1}$$

where E, I, EI, and E-I denote the active enzyme, inhibitor, non-covalent enzyme-inhibitor complex and covalent enzyme-inhibitor adduct, respectively. The $K_i$ value is the overall dissociation constant of reversible binding steps, and $k_3$ is the irreversible rate constant. The [S] and $K_s$ values are the substrate concentration and the dissociation constant of the substrate bound to the enzyme, respectively.

Figure 3:
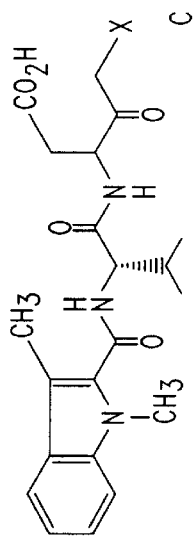
FIG. 3 illustrates the activity of the compounds in Formula C regarding recombinant ICE, CPP32, MCH2 and MCH5 enzymes.
Figure 5:
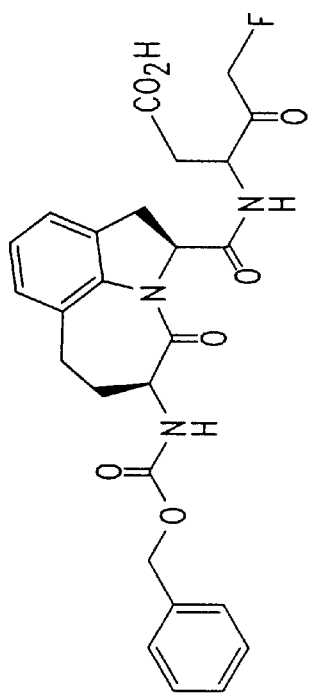
FIG. 5 sets forth the activity of Example 106 in inhibiting the activity of ICE, CPP32, MCH2 and MCH5.

The above equations were used to determine the $K_i$ and $k_3$ values of a given inhibitor bound to a ICE/ced-3 family protease. Thus, a continuous assay was run for sixty minutes at various concentrations of the inhibitor and the substrate. The assay was formulated essentially the same as described above for generating the data in Table 1, except that the reaction was initiated by adding the enzyme to the substrate-inhibitor mixture. The Ki and $k_3$ values were obtained by simulating the product AMC formation as a function of time according to Equation I. The results of this second assay are set forth below in Tables 2, 3 and 5 (FIGS. 2, 3 and 5).

The reference compound for this assay was Cbz-ValAlaAsp-CH$_2$F and the values are denoted in Tables 2, 3 and 5 as "Reference".

EXAMPLE 2

(3S)-3-[(1-Methylindole-2-Carbonyl)Alaninyl] Amino-4-Oxobutanoic Acid, t-Butyl Ester Semicarbazone 1-Methylindole-2-carboxylic acid (107 mg, 0.6 mmol) and (3S)-3-(alaninyl)-amino-4-oxobutanoic acid, t-butyl ester semicarbazone (188 mg, 96%, 0.6 mmol) were dissolved in DMF (2 mL) then both 1-hydroxybenzotriazole-hydrate (96 mg, 0.63 mmol) and 1-(3-dimethylaminopropyl)-3-ethyl carbodiimide hydrochloride (EDAC) (161 mg, 0.84 mmol) was added to the resultant mixture under a nitrogen atmosphere at 0° C. Stirring was continued for 1 hour at 0° C. and an additional 20 hours at room temperature. The reaction mixture was diluted with ethyl acetate, washed successively with saturated aqueous sodium bicarbonate solution and brine, dried over sodium sulfate and concentrated to give a yellow solid. Trituration of the solid with ether afforded the title product as a slightly yellow powder (213 mg, 77%). TLC: (methanol/methylene chloride: 1/9, silica gel): $R_f$=0.47; $^1$H NMR (CDCl$_3$+ CD$_3$OD): δ 7.96 (d, J=8.0, 1H), 7.57–7.67 (m, 2H), 7.31–7.42 (m, 2H), 7.13–7.19 (m, 2H), 7.06 (s, 1H), 4.91 (m, 1H), 4.65 (q, J=7.1, 1H), 4.01 (s, 3H), 2.59–2.78 (m, J=5.6, 15.7, 2H), 1.49 (d, J=7.1, 3H), 1.39 (s, 9H).

EXAMPLE 3

(3S)-3-[(1-Methylindole-2-Carbonyl)Alaninyl] Amino-4-Oxobutanoic Acid, Semicarbazone (3S)-3-[(1-Methylindole-2-carbonyl)alaninyl]amino-4-oxobutanoic acid, t-butyl ester semicarbazone (127 mg, 0.28 mmol) was suspended in anisole (0.2 mL) and methylene chloride (2 mL) and the suspension was treated with trifluroacetic acid (TFA) (1 mL). The resulting solution was stirred for 2 hours under a nitrogen atmosphere at room temperature. The reaction mixture was then concentrated and chased with methylene chloride to give a purple foam. Trituration of the foam with ether gave the title product as a purple powder (108 mg, 97%). TLC: (methylene chloride:methanol:acetic acid, 20:1:1, silica gel): $R_f$=0.27; $^1$H NMR (CD$_3$OD): δ 7.62 (d, J=8.0, 1H), 7.44 (d, J=8.2, 1H), 7.24–7.32 (m, 2H), 7.07–7.13 (m, 2H), 4.91 (m, 1H), 4.56 (q, J=7.1, 1H), 3.98 (s, 3H), 2.78 (d, J=6.5, 2H), 1.49 (d, J=7.3, 3H).

EXAMPLE 4

(3S)-3-[(1-Methylindole-2-Carbonyl)Alaninyl] Amino-4-Oxobutanoic Acid (3S)-3-[(1-Methylindole-2-carbonyl)alaninyl]amino-4-oxobutanoic acid, semicarbazone (87 mg, 0.22 mmol) was dissolved in methanol (3 mL), formaldehyde (1 mL, 37% wt. aq) and acetic acid (1 mL) and the resultant mixture was stirred for 4 hours under a nitrogen atmosphere at room temperature. The reaction mixture was diluted with water and extracted twice with ethyl acetate. The ethyl acetate solution was washed with brine, dried over sodium sulfate and concentrated to give a glassy material which was triturated with ether to afford the title product as a gray powder (24 mg, 32%). TLC: (methylene chloride:methanol:acetic acid, 20:1:1, silica gel): $R_f$=0.44; $^1$H NMR (CD$_3$OD): δ 7.62 (d, J=8.0, 1H), 7.44 (dd, J=0.8, 8.4, 1H), 7.26–7.32 (m, 1H), 7.08–7.13 (m, 2H), 4.63–4.53 (m, 2H), 4.31 (m, 1H), 3.99 (s, 3H), 2.48–2.73 (m, 2H), 1.46 (7.1, 3H).

EXAMPLE 5

(3S)-3-[(1-Methylindole-2-Carbonyl)Prolinyl] Amino-4-Oxobutanoic Acid, t-Butyl Ester Semicarbazone 1-Methylindole-2-carboxylic acid (102 mg, 0.58 mmol) and (3S)-3-(prolinyl)amino-4-oxobutanoic acid, t-butyl ester semicarbazone (189 mg, 0.58 mmol) were dissolved in methylene chloride (2 mL) and DMF (1 mL) and then both 4-dimethylamino pyridine (DMAP) (71 mg, 0.58 mmol) and EDAC (155 mg, 0.81 mmol) were added to the mixture under a nitrogen atmosphere at 0° C. Stirring was continued for 1 hour at 0° C. and an additional 2 hours at room temperature. The reaction mixture was partitioned between ethyl acetate and 5% KHSO$_4$ solution. The ethyl acetate solution was washed with saturated sodium bicarbonate solution and brine, dried over sodium sulfate and concentrated to give 153 mg of brown foam. The foam was purified by flash chromatograph on silica gel using 2% methanol-methylene chloride as the eluant to give the title product as a light brown foam (50 mg). TLC: (methanol/methylene chloride: 5/95, silica gel): $R_f$=0.27; $^1$H NMR (CDCl$_3$+CD$_3$OD): δ 8.87 (bs, 1H), 7.63 (d, J=7.7, 1H), 7.38–7.50 (m, 2H), 7.17–7.13 (m, 1H), 6.85 (bs, 1H), 4.90–4.81, (m, 2H), 3.92–3.74 (m, 5H), 2.78–1.93 (m, 6H), 1.37 (s, 9H).

EXAMPLE 6

(3S)-3-[(1-Methylindole-2-Carbonyl)Prolinyl] Amino-4-Oxobutanoic Acid, Semicarbazone (3S)-3-[(1-Methylindole-2carbonyl)prolinyl]amino-4-oxobutanoic acid, t-butyl ester semicarbazone (50 mg, 0.1 mmol) was dissolved in anisole (0.2 mL) and methylene chloride (2 mL) and the resultant solution was treated with TFA (1 mL). This reaction mixture was then stirred for 1 hour under a nitrogen atmosphere at room temperature. The reaction mixture was concentrated in vacuo and chased with methylene chloride to give a purple film. The film was triturated with ether to afford the title product as a purple powder (47 mg). TLC: (methylene chloride:methanol:acetic acid, 20:1:1, silica gel): $R_f$=0.18; $^1$H NMR (CD$_3$OD): δ 7.63–6.93 (m, 6H), 6.67 (bs, 1H), 4.89–4.50 (m, 2H), 3.86–3.74 (m, 5H), 2.82–2.74 (m, 2H), 2.40–2.30 (m, 1H), 2.15–1.90 (m, 3H).

EXAMPLE 7

(3S)-3-[(1-Methylindole-2-Carbonyl)Prolinyl] Amino-4-Oxobutanoic Acid (3S)-3-[(1-Methylindole-2-carbonyl)prolinyl]amino-4-oxobutanoic acid, semicarbazone (87 mg, 0.22 mmol) was dissolved in methanol (3 mL), formaldehyde (1 mL, 37% wt. aq) and acetic acid (1 mL) and the resulting mixture was stirred for 4 hours under a nitrogen atmosphere at room temperature. The reaction mixture was concentrated in vacuo, diluted with water, and extracted twice with ethyl acetate. The ethyl acetate solution was washed with brine, dried over sodium sulfate and concentrated to give brown oil (22 mg) which was triturated with ether to afford the title product as a light brown powder (8 mg). TLC: (methylene chloride:methanol:acetic acid, 20:1:1, silica gel): $R_f$=0.28; MS (EI) for $C_{19}H_{21}N_3O_5+H^+$=372; $C_{19}H_{21}N_3O_5-H^+$=370).

EXAMPLE 8

(3S)-3-[(1-Methylindole-2-Carbonyl)Valinyl]Amino-4-Oxobutanoic Acid, t-Butyl Ester Semicarbazone 1-Methylindole-2-carboxylic acid (88 mg, 0.5 mmol) and (3S)-3-(Valinyl)amino-4-oxobutanoic acid, t-butyl ester semicarbazone (163 mg, 0.5 mmol) were dissolved in DMF (1 mL) and methylene chloride (2 mL) then both DMAP (61 mg, 0.50 mmol) and EDAC (134 mg, 0.7 mmol) were added to the solution under a nitrogen atmosphere at 0° C. Stirring was continued for 1 hour at 0° C. and an additional 4 hours at room temperature. The reaction mixture was partitioned between ethyl acetate and 5% KHSO$_4$ solution. The ethyl acetate solution was washed successively with 5% KHSO$_4$ solution, saturated sodium bicarbonate solution and brine solutions, dried over sodium sulfate, and concentrated to give a yellow foam. Trituration of the foam with ether afforded the title product as a slightly yellow powder (203 mg, 86%). TLC: (methanol/methylene chloride: 5/95, silica gel): $R_f$=0.17.

EXAMPLE 9

(3S)-3-[(1-Methylindole-2-Carbonyl)Valinyl]Amino-4-Oxobutanoic Acid Semicarbazone (3S)-3-[(1-Methylindole-2-carbonyl)valinyl]amino-4-oxobutanoic acid, t-butyl ester semnicarbazone (170 mg, 0.36 mmol) was dissolved in anisole (0.2 mL) and methylene chloride (2 mL) and the resulting solution was treated with TFA (1 mL). The resulting solution was stirred for 3.5 hours under a nitrogen atmosphere at room temperature. The reaction mixture was concentrated in vacuo and chased with methylene chloride to give a purple foam. Trituration of the foam with ether afforded the title product as a solid purple powder (133 mg, 89%).

EXAMPLE 10

(3S)-3-[(1-Methylindole-2-Carbonyl)Valinyl]Amino-4-Oxobutanoic Acid (3S)-3-[(1-Methylindole-2-carbonyl)valinyl]amino-4-oxobutanoic acid, semicarbazone (136 mg, 0.33 mmol) was dissolved in methanol (3 mL), formaldehyde (1 mL, 37% wt. aq) and acetic acid (1 mL) and the resulting mixture was stirred for 5 hours under a nitrogen atmosphere at room temperature. The reaction mixture was concentrated in vacuo diluted with water, and extracted twice with ethyl acetate. The combined ethyl acetate solutions were washed with brine, dried over sodium sulfate and concentrated in vacuo to give a purple foam which was triturated with ether to afford the title product as a purple powder (40 mg, 33%). TLC: (methylene chloride:methanol:acetic acid, 20:1:1, silica gel): $R_f$=0.36; MS (EI) for $C_{19}H_{23}N_3O_5$+$H^+$=374; $C_{19}H_{23}N_3O_5$−$H^+$=372).

EXAMPLE 11

(3S)-3-[(1-Methylindole-2-Carbonyl)Leucinyl]
Amino-4-Oxobutanoic Acid, t-Butyl Ester
Semicarbazone 1-Methylindole-2-carboxylic acid (70 mg, 0.4 mmol) and 3(S)-(Leucinyl)amino-4-oxobutanoic acid, t-butyl ester semicarbazone (131 mg, 0.4 mmol) were dissolved in methylene chloride (2 mL) and both DMAP (49 mg, 0.40 mmol) and EDAC (107 mg, 0.56 mmol) were added to the solution under a nitrogen atmosphere at 0° C. Stirring was continued for 1 hour at 0° C. and an additional 3 hours at room temperature. The reaction mixture was partitioned between ethyl acetate and 5% $KHSO_4$ solution. The ethyl acetate solution was washed successively with 5% $KHSO_4$ solution, saturated with sodium bicarbonate solution (2×) and brine, dried over sodium sulfate, and concentrated in vacuo to give a crude solid. Trituration of the solid with ether afforded the title product as a white powder (156 mg, 80%). TLC: (methanol/methylene chloride: 5/95, silica gel): $R_f$=0.42; $^1$H NMR ($CDCl_3$+$CD_3OD$): δ 8.18 (s, 1H), 7.66–7.11 (m, 6H), 6.97 (s, 1H), 6.32 (d, J=7.7, 1H), 4.95–4.88 (m, 1H), 4.70–4.62 (m, 1H), 4.03 (s, 3H), 2.82–2.56 (m, 2H), 1.87–1.58 (m, 3H), 1.38 (9H), 1.00 (t, J=6.3, 6H).

EXAMPLE 12

(3S)-3-[(1-Methylindole-2-Carbonyl)Leucinyl]
Amino-4-Oxobutanoic Acid, Semicarbazone (3S)-3-[(1-Methylindole-2-carbonyl)leucinyl]amino-4-oxobutanoic acid, t-butyl ester semicarbazone (132 mg, 0.27 mmol) was dissolved in anisole (0.2 mL) and methylene chloride (2 mL) and the resulting solution was treated with TFA (1 mL). The resulting solution was stirred for 3 hours under a nitrogen atmosphere at room temperature. The reaction mixture was concentrated in vacuo and chased with methylene chloride to give a pink foam. Trituration of the foam with ether afforded the title product as a pink powder (108 mg, 92%). TLC: (methylene chloride:methanol:acetic acid, 20:1:1, silica gel): $R_f$=0.22; $^1$H NMR ($CD_3OD$): δ 7.62 (dt, J=8.0, 1.1, 1H), 7.45 (dd, J=8.5, 0.8, 1H), 7.32–7.23 (m, 2H), 7.13–7.08 (m, 2H), 4.94–4.89 (m, 1H), 4.64–4.59 (m, 1H), 3.98 (s, 3H), 2.78 (d, J=6.2, 2H), 1.82–1.70 (m, 3H), 1.02 (d, J=6.0, 3H), 0.99 (d, J=6.3, 3H).

EXAMPLE 13

(3S)-3-[(1-Methylindole-2-Carbonyl)Leucinyl]
Amino-4-Oxobutanoic Acid (3S)-3-[(1-Methylindole-2-carbonyl)leucinyl]amino-4-oxobutanoic acid, semicarbazone (90 mg, 0.21 mmol) was dissolved in methanol (3 mL), formaldehyde (1 mL, 37% wt. aq) and acetic acid (1 mL) and the resulting solution was stirred for 7 hours under a nitrogen atmosphere at room temperature. The reaction mixture was concentrated in vacuo, diluted with water, and extracted twice with ethyl acetate. The ethyl acetate solution was washed with brine, dried over sodium sulfate, and concentrated in vacuo to give a purple foam which was triturated with ether to afford the title product as a purple powder (35 mg, 43%). TLC: (methylene chloride:methanol:acetic acid, 20:1:1, silica gel): $R_f$=0.45; MS(EI) for $C_{20}H_{25}N_3O_5$; $M+H^+$=388; $M-H^+$=386.

EXAMPLE 14

(3S)-3-[(1-Methylindole-2-Carbonyl)Phenylalaninyl]
Amino-4-Oxobutanoic Acid, t-Butyl Ester
Semicarbazone 1-Methylindole-2-carboxylic acid (72 mg, 0.41 mmol) and 3(S)-(phenylalaninyl]amino-4-oxobutanoic acid, t-butyl ester semicarbazone (154 mg, 0.41 mmol) were dissolved in methylene chloride (2 mL) and both DMAP (53 mg, 0.43 mmol) and EDAC (109 mg, 0.57 mmol) were added to the solution under a nitrogen atmosphere at 0° C. Stirring was continued for 1 hour at 0° C. and an additional 4 hours at room temperature. The reaction mixture was partitioned between ethyl acetate and 5% $KHSO_4$ solution, successively, dried over sodium sulfate, and concentrate to give a white solid. Trituration of the solid with ether afforded the title product as a white powder (179 mg, 82%). TLC: (methanol/methylene chloride: 5/95, silica gel): $R_f$=0.44.

EXAMPLE 15

(3S)-3-[(1-Methylindole-2-Carbonyl)Phenylalaninyl]
Amino-4-Oxobutanoic Acid, Semicarbazone (3S)-3-[(1-Methylindole-2-carbonyl)phenylalaninyl]amino-4-oxobutanoic acid, t-butyl ester semicarbazone (154 mg, 0.30 mmol) was dissolved in anisole (0.2 mL) and methylene chloride (2 mL) and the resulting solution was treated with TFA (1 mL). The resulting solution was stirred for 4 hours under a nitrogen atmosphere at room temperature. The reaction mixture was concentrated in vacuo and azeotroped with methylene chloride to give a purple solid. Trituration of the solid with ether afforded the title product as a purple powder (141 mg, 100%). TLC: (methylene chloride:methanol:acetic acid, 20:1:1, silica gel): $R_f$=0.25.

EXAMPLE 16

(3S)-3-[(1-Methylindole-2-Carbonyl)Phenylalaninyl]
Amino-4-Oxobutanoic Acid (3S)-3-[(1-Methylindole-2-carbonyl)phenylalaninyl]amino-4-oxobutanoic acid, semicarbazone (116 mg, 0.25 mmol) were dissolved in methanol (3 mL), formaldehyde (1 mL, 37% wt. aq) and acetic acid (1 mL) and the resulting solution was stirred for 9 hours under a nitrogen atmosphere at room temperature. The reaction mixture was concentrated in vacuo, diluted with water, and extracted twice with ethyl acetate. The ethyl acetate solution was washed with brine, dried over sodium sulfate and concentrated to give a crude product which was triturated with ether to afford the title product as a brown powder (26 mg, 25%). TLC: (methylene chloride:methanol:acetic acid, 20:1:1, silica gel): $R_f$=0.33; MS(EI) for $C_{23}H_{21}N_3O_5$; M+H$^+$=422; M−H$^+$=420.

EXAMPLE 17

(1-Methylindole-2-Carbonyl)Glycine, Methyl Ester

DMAP (1.222 g, 0.01 mol) and EDAC (2.680 g, 0.014 mol) were added as solids to a solution of 1-methylindole-2-carboxylic acid (1.752 g, 0.01 mol) and glycine methyl ester hydrochloride (1.256 g, 0.01 mol) in methylene chloride (30 mL) and DMF (5 mL) under a nitrogen atmosphere at 0° C. Stirring was continued for 1 hour at 0° C. and then for 3 hours at room temperature. The reaction mixture was partitioned with ethyl acetate and 5% KHSO$_4$ solution and the aqueous layer was extracted with ethyl acetate. The combined ethyl acetate solution was washed with 5% KHSO$_4$ solution, saturated sodium bicarbonate solution (2×) solution and brine, dried over sodium sulfate, and concentrated to give a purple powder as crude product. Trituration of the powder with ether afforded the title product (1.734 mg, 70%). TLC: (methanol/methylene chloride 1:9): $R_f$=0.61; $^1$H NMR (CDCl$_3$): δ 7.65 (dt, J=8.0, 1.1, 1H), 7.41–7.31 (m, 2H), 7.16 (dd, J=6.6, 1.4, 1H) 6.96 (d, J=0.5, 1H), 6.67 (bs, 1H), 4.25 (d, J=5.2, 2H), 4.05 (s, 3H), 3.82 (s, 3H).

EXAMPLE 18

(1-Methylindole-2-Carbonyl)Glycine (1-Methylindole-2-carbonyl)glycine methyl ester (1.687 g, 6.85 mmol) was dissolved in 1,4-dioxane (10 mL) and was treated with 1 N lithium hydroxide (7.0 mL, aq) with stirring. The reaction mixture turned clear immediately and was acidified with 1N HCl and concentrated to remove 1,4-dioxane to result in a purple precipitate. The precipitate was filtered, washed with water, and dried in vacuo to give the title product as a purple powder (1.482 g, 93%). TLC: (methylene chloride:methanol:acetic acid, 20:1:1, silica gel): $R_f$=0.28; $^1$H NMR (CD$_3$OD): δ 7.61 (dt, J=8.2, 1H). 7.44 (dd, J=8.5, 0.8, 1H), 7.32–7.26 (m, 1H), 7.13–7.09 (m, 1H), 7.04 (s, 1H), 4.08 (s, 2H), 3.99 (s, 3H).

EXAMPLE 19

(3S)-3-[(1-Methylindole-2-Carbonyl)Glycine] Amino-4-Oxobutanoic Acid, t-Butyl Ester Semicarbazone (1-Methylindole-2-carbonyl)glycine (186 mg, 0.8 mmol) was dissolved in methylene chloride (5 mL) and DMF (1 mL) and the resulting solution was treated with 1-hydroxybenzotriazole hydrate (129 mg, 0.84 mmol) and EDAC (215 mg, 1.12 mmol) under a nitrogen atmosphere and the reaction mixture stirred for 10 minutes at 0° C. 3(S)-Amino-4-oxobutanoic acid, t-butyl ester semicarbazone p-toluenesulfate (312 mg, 0.8 mmol) followed by N-methylmorpholine (0.09 mL, 0.8 mmol), were added to the reaction mixture and the mixture was stirred for 1 hour at 0° C. and an additional 4 hours at room temperature. The reaction mixture was partitioned between ethyl acetate and 5% KHSO$_4$, and the product precipitated out during the work-up. The white precipitate from the aqueous portion was obtained by filtration and washing with water and ether. Another portion of white precipitate was obtained by concentration of the organic layer and trituration of the residue with ether. The combined precipitate was the title product (297 mg, 66%). TLC: (methanol/methylene chloride: 1/9, silica gel): $R_f$=0.42; $^1$H NMR (CDCl$_3$) δ 7.65 (d, J=8.0, 1H), 7.41–7.34 (m, 2H), 7.19–7.13 (m, 2H), 7.05 (d, J=0.5, 1H), 4.95–4.93 (m, 1H), 4.08 (s, 2H), 4.03 (s, 3H), 2.79–2.59 (m, 2H), 1.41 (s, 9H).

EXAMPLE 20

(3S)-3-[(1-Methylindole-2-Carbonyl)Glycinyl] Amino-4-Oxobutanoic Acid, Semicarbazone (3S)-3-[(1-Methylindole-2-carbonyl)glycinyl]amino-4-oxobutanoic acid, t-butyl ester semicarbazone (118 mg, 0.26 mmol) was dissolved in anisole (0.2 mL) and methylene chloride (2 mL) and the resulting solution was treated with TFA (1 mL). The resulting solution was stirred for 3 hours under a nitrogen atmosphere at room temperature. The reaction mixture was concentrated in vacuo and chased with methylene chloride to give a green solid. Trituration of the solid with ether afforded the title product as a green powder (88 mg, 87%). TLC: (methylene chloride:methanol:acetic acid, 20:1:1, silica gel): $R_f$=0.47; $^1$H NMR (CD$_3$OD): δ 7.63–7.08 (m, 6H), 4.95 (m, 1H), 4.05 (s, 2M), 4.01 (s, 3H), 3.77 (d, J=5.8, 2H).

EXAMPLE 21

(3S)-3-[(1-Methylindole-2-Carbonyl)Glycinyl]-Amino-4-Oxobutanoic Acid (3S)-3-[(1-Methylindole-2-carbonyl)glycinyl]amino-4-oxobutanoic acid, semicarbazone (76 mg, 0.20 mmol) was dissolved in a mixture of methanol (3 mL), formaldehyde (1 mL, 37% wt. aq) and acetic acid (1 mL) and the mixture was stirred for 6 hours under a nitrogen atmosphere at room temperature. The reaction mixture was concentrated in vacuo. diluted with water, extracted twice with ethyl acetate. The combined ethyl acetate solutions were washed with brine, dried over sodium sulfate, and concentrated to give a crude product which was triturated with ether to afford the title product as a light yellow powder (29 mg, 44%). TLC: (methylene chloride:methanol:acetic acid, 8:1:1, silica gel): $R_f$=0.61; MS(EI) for $C_{16}H_{17}N_3O_5$:M+H$^+$, 330. $^1$H NMR (CD$_3$OD): δ 7.73–7.08 (m, 5H), 4.90–3.8 (m, 7H), 2.72–2.47 (m, 2H).

EXAMPLE 22

(3S)-3-[(1-Benzylindole-2-Carbonyl)Alaninyl] Amino-4-Oxobutanoic Acid, t-Butyl Ester Semicarbazone 1-Benzylindole-2-carboxylic acid (477 mg, 1.9 mmol) and 3(S)-(alaninyl)amino-4-oxobutanoic acid, t-butyl ester semicarbazone (581 mg, 1.9 mmol) were dissolved in methylene chloride (8 mL) and both DMAP (232 mg, 1.9 mmol) and EDAC (498 mg, 2.6 mmol) were added to the solution under a nitrogen atmosphere at 0° C. The resultant solution was stirred for 1 hour at 0° C. and an additional 2 hours at room temperature. The reaction mixture was diluted with ethyl acetate, washed successively with saturated sodium bicarbonate solution and brine, dried over sodium sulfate, and concentrated to give a yellow foam. Flash column chromatographic purification of the foam (silica gel, methanol/methylene chloride 2–5%) afforded the title product as a white powder (570 mg, 56%). TLC: (methanol/methylene chloride: 1/9, silica gel): $R_f$=0.38; $^1$H NMR (CDCl$_3$): δ 8.60 (bs, 1H), 7.67 (dd, J=8.0, 1.1, 1H), 7.50 (d, J=8.0, 1H), 7.33–7.01 (m, 8H), 6.79)(d, J=7.4, 1H), 5.78 (s, 2H), 4.87–4.83 (m, 1H), 4.67–4.62 (m, 1H), 2.73–2.43 (m, 2H), 1.46 (d, J=7.1, 3H), 1.39 (s, 9H).

EXAMPLE 23

(3s)-3-[(1-Benzylindole-2-Carbonyl)Alaninyl] Amino-4-Oxobutanoic Acid, Semicarbazone (3S)-3-[(1-Benzylindole-2-carbonyl)alaninyl]amino-4-oxobutanoic acid, t-butyl ester semicarbazone (247 mg, 0.46 mmol) was dissolved in anisole (0.5 mL) and methylene chloride (2 mL) and the resultant mixture was treated with TFA (1 mL). The resulting solution was stirred for 3.5 hours under a nitrogen atmosphere at room temperature. The reaction mixture was concentrated and chased with methylene chloride to give a light green solid. Trituration of the solid with ether afforded the title product as a green powder (215 mg, 98%). TLC: (methylene chloride:methanol:acetic acid, 8:1:1, silica gel): $R_f$=0.50; $^1$H NMR (CD$_3$OD): δ 8.26 (d, J=8.0, 1H), 7.65 (d, J=8.0, 1H), 7.39 (dd, J=8.5, 0.8, 1H), 7.26–7.01 (m, 8H), 5.79 (d, J=7.4, 2H), 4.56–4.49 (m, 1H), 2.77–2.62 (m, 2H), 1.43 (d, J=7.4, 3H).

EXAMPLE 24

(3S)-3-[(1-Benzylindole-2-Carbonyl)Alaninyl] Amino-4-Oxobutanoic Acid (3S)-3-[(1-Benzylindole-2-carbonyl)alaninyl]amino-4-oxobutanoic acid, semicarbazone (176 mg, 0.37 mmol) was dissolved in methanol (4.5 mL), formaldehyde (1.5 mL, 37% wt. aq) and acetic acid (1.5 mL) and the resulting mixture was stirred for 4 hours under a nitrogen atmosphere at room temperature. The reaction mixture was concentrated in vacuo, diluted with water, and extracted twice with ethyl acetate. The ethyl acetate solution was washed with brine, dried over sodium sulfate, and concentrated to give a crude product which was triturated with ether to afford the title product as a light green powder (113 mg, 72%). TLC: (methylene chloride:methanol:acetic acid, 20:1:1, silica gel): $R_f$=0.38; MS for $C_{23}H_{23}N_3O_5$; M+H$^+$=422; M–H$^+$420. $^1$H NMR (CD$_3$OD): δ 7.65 (d, J=8.0, 1H), 7.37 (dd, J=8.2, 0.8, 1H), 7.24–7.04 (m, 8H), 5.87–5.73 (m, 2H), 4.60–4.49 (m, 2H), 4.32–4.23 (m, 1H), 2.69–2.44 (m, 2H), 1.41 (d, J=7.1, 2 sets 3H).

EXAMPLE 25

(3S)-3-[(1-(4'-Butenyl)Indole-2-Carbonyl)Valinyl] Amino-4-Oxobutanoic Acid, t-Butyl Ester Semicarbazone

[1-(4'-Butenyl)indole]-2-carboxylic acid (108 mg, 0.5 mmol) and 3(S)-(valinyl)amino-4-oxobutanoic acid, t-butyl ester semicarbazone (163 mg, 0.5 mmol) were dissolved in methylene chloride (3 mL). To this solution was added both DMAP (61 mg, 0.5 mmol) and EDAC (134 mg, 0.7 mmol) under a nitrogen atmosphere at 0° C. and the resultant reaction mixture was stirred for 1 hour at 0° C. and an additional 5 hours at room temperature. The reaction mixture was diluted with ethyl acetate, washed successively with saturated sodium bicarbonate solution and brine, dried under sodium sulfate, and concentrated to give a yellow foam. Trituration of the foam with ether afforded the title product as a slightly yellow powder (146 mg, 55%). TLC: (methanol/methylene chloride: 1/9, silica gel): $R_f$=0.23; $^1$H NMR (CDCl$_3$): δ 8.69 (bs, 1H), 7.64 (d, J=8.0, 1H) 7.41–7.13 (m, 3H), 6.99 (s, 1H), 6.91 (d, J=8.8, 1H), 5.85–5.71 (m, 1H), 5.04–4.94 (m, 3H), 4.65–4.45 (m, 3H), 3.52–2.50 (m, 4H), 2.33–2.26 (m, 1H), 1.41 (s, 9H), 1.05–1.02 (m, 6H).

EXAMPLE 26

(3S)-3-[(1-(4'-Butenyl)Indole-2-Carbonyl)Valinyl] Amino-4-Oxobutanoic Acid, Semnicarbazone (3S)-3-[(1-(4-Butenyl)indole-2-carbonyl) valinyl]amino-4-oxobutanoic acid, t-butyl ester semicarbazone (126 mg, 0.24 mmol) was dissolved in anisole (0.2 mL) and methylene chloride (2 mL) and the resulting solution was treated with TFA (1 mL). The acidified reaction mixture was stirred for 4 hours under a nitrogen atmosphere at room temperature. The reaction mixture was concentrated and chased with methylene chloride to give a crude solid. Trituration of the solid with ether afforded the title product as a purple powder (99 mg, 88%). TLC: (methylene chloride:methanol:acetic acid, 20:1:1, silica gel): $R_f$=0.36; $^1$H NMR (CD$_3$OD): δ 8,46 (d, J=8.0, 1H) 8.12 (d, J=8.5, 1H), 7.62 (d, J=8.0, 1H), 7.46 (dd, J=8.5, 0.8, 1H), 7.31–7.21 (m, 2H), 7.31–7.05 (m, 2H), 5.84–5.70 (m, 1H), 4.99–4.78 (m, 3H), 4.62–4.57 (m, 2H), 4.39–4.33 (m, 1H), 2.88–2.69 (m, 2H), 2.52–2.45 (m, 2H), 2.24–2.15 (m, 1H), 1.07–1.02 (m, 6H).

EXAMPLE 27

(3S)-3-[(1-(4'-Butenyl)indole-2-Carbonyl)Valinyl] Amino-4-Oxobutanoic Acid (3S)-3-[(1-(4'-Butenyl)indole-2-carbonyl)valinyl]amino-4-oxobutanoic acid, semicarbazone (79 mg, 0.17 mmol) was dissolved in methanol (3 mL), formaldehyde (1 mL, 37% wt. aq) and acetic acid (1 mL) and the resulting mixture was stirred for 7 hours under a nitrogen atmosphere at room temperature. The reaction mixture was concentrated in vacuo, diluted with water, and extracted twice with ethyl acetate. The ethyl combined acetate solutions were washed with brine, dried over sodium sulfate and concentrated to give a crude product which was triturated with ether to afford the title product as a light purple powder (24 mg, 34%). TLC: (methylene chloride:methanol:acetic acid, 20:1:1, silica gel): $R_f$=0.60; MS(EI) for $C_{22}H_{27}N_{3O5}$:M+H$^+$=414; M–H$^+$=412. $^1$H NMR (CD$_3$OD): δ 8.09–8.05 (m, 1H), 7.62 (d, J=8.0, 1H), 7.46 (dd, J=8.5, 0.8, 1H), 7.31–7.25 (m, 1H), 7.13–7.07 (m, 2H), 5.85–5.71 (m, 1H), 4.99–4.90 (m, 3H), 4.62–4.54 (m, 3H), 4.41–4.30 (m, 2H), 2.75–2.46 (m, 4H), 2.22–2.14 (m, 1H), 1.06–1.02 (m, 6H).

EXAMPLE 28

(3S)-3-[(1-(2'-(1'-t-Butoxy-1'-Oxo)Ethyl)Indole-2-Carbonyl)Alaninyl]Amino-4-Oxobutanoic Acid, t-Butyl Ester Semicarbazone 1-[2'-(1'-t-Butoxy-1'-oxo)ethyl]indole-2-carboxylic acid (220 mg, 0.8 mmol) and 3(S)-(alaninyl)amino-4-oxobutanoic acid, t-butyl ester semicarbazone (241 mg, 0.8 mmol) were dissolved in methylene chloride (3 mL) and DMF (1 mL) and the resulting solution was treated with both DMAP (98 mg, 0.8 mmol) and EDAC (211 mg. 1.1 mmol).

The resultant reaction mixture was stirred for 1 hour at 0° C. and then an additional 3 hours at room temperature to give a white precipitate. The reaction mixture was concentrated to remove methylene chloride and quenched with 5% $KHSO_4$ solution. The white solid was collected by filtration, washed with water and ether and dried in vacuo to afford the title product as a white powder (297 mg, 66%). TLC: (methanol/methylene chloride:1/9, silica gel): $R_f$=0.27. $^1H$ NMR: ($CD_3OD$) δ 7.65 (d, J=8.0, 1H), 7.41)d, J=8.0, 1H), 7.26 (s, 1H), 7.22 (d, J=3.0, 1H), 7.16–7.11 (m, 1H), 5.32 (d, J=2.2, 2H), 4.94–4.89 (m, 1H), 4.54 (q, J=7.1, 1H), 2.76 (d, 2H), 1.48 (d, J=7.4, 3H).

EXAMPLE 29

(3S)-3-[(1-(Carboxymethyl)-Indole-2-Carbonyl) Alaninyl]Amino-4-Oxobutanoic Acid, Semicarbazone (3S)-3-[(1-(2'-(1'-t-butoxy-1'-oxo)ethyl)indole-2-carbonyl)]amino-4-oxobutanoic acid, t-butyl ester, semicarbazone (274 mg, 0.51 mmol) in methylene chloride (2 mL) was treated with TFA (1 mL). The resulting solution was stirred for 2 hours under a nitrogen atmosphere at room temperature. The reaction mixture was concentrated and chased with methylene chloride to give a solid. Trituration of the solid with ether gave the title product as a light gray powder (262 mg). TLC: (methylene chloride:methanol:acetic acid, 8:1:1, silica gel): $R_f$=0.08. $^1H$ NMR ($CD_3OD$): δ 7.65 (d, J=8.0, 1H), 7.41 (d, J=8.0,1H), 7.26 (s, 1H), 7.22 (d, J=3.0, 1H), 7.16–7.11 (m, 1H), 5.32 (d, J=2.2, 2H), 4.94–4.89 (m, 1H), 4.54 (q, J=7.1, 1H), 2.76 (d, 2H), 1.48 (d, J=7.4, 3H).

EXAMPLE 30

(3S)-3-[(1-(Carboxymethyl)Indole-2-Carbonyl) Alaninyl]Amino-4-Oxobutanoic Acid (3S)-3-[(1-(Carboxymethyl)indole-2-carbonyl)alaninyl]amino-4-oxobutanoic acid, semicarbazone (241 mg, 0.47 mmol) was dissolved in methanol (3 mL), formaldehyde (1 mL, 37% wt. aq) and acetic acid (1 mL) and the resulting solution was stirred for 3 hours under a nitrogen atmosphere at room temperature. The reaction mixture was concentrated in vacuo, diluted with water and extracted twice with ethyl acetate. The combined ethyl acetate solutions were washed with brine, dried under sodium sulfate and concentrated to give a glassy material which was triturated with ether to afford the title product as a slightly yellow powder (114 mg, 63%). TLC: (methylene chloride:methanol:acetic acid, 8:1:1, silica gel): $R_f$=0.16. $^1H$ NMR ($CD_3OD$): δ 7.65 (d, J=8.0, 1H), 7.40 (d, J=8.2, 1H), 7.33–7.27 (m, 1H), 7.24 (s, 1H), 7.16–7.10 (m, 1), 5.36 and 5.26 (AB, J=17.9, 2H), 4.64–4.50 (m, 2H), 4.34–4.20 (m, 1H), 2.72–2.48 (m, 2H), 1.45 (d, J=7.14, 3H, 2 sets).

EXAMPLE 31

(3S)-3-[(1-(3'-(1'-t-Butoxy-1'-Oxo)Propyl)indole-2-Carbonyl)Alaninyl]Amino-4-Oxobutanoic Acid, t-Butyl Ester Semicarbazone 1-(3'-(1'-t-Butoxy-1'-oxo)propyl)indole-2-carboxylic acid (147 mg, 0.51 mmol) was dissolved in DME 3 mL) aid to the resulting solution was added both DMAP (68 mg, 0.56 mmol) and EDAC (140 mg, 0.73 mmol). Stirring was continued for 10 minutes under a nitrogen atmosphere at 0° C. (3S)-3-(Alaninyl)amino-4-oxobutanoic acid, t-butyl ester semicarbazone (154 mg, 0.51 mmol) was added to the reaction mixture, and the mixture was stirred for 1 hour at 0° C. and then an additional 4 hours at room temperature. The reaction mixture was partitioned between 5% $KHSO_4$ solution and ethyl acetate. The ethyl acetate solution was washed successively with 5% $KHSO_4$ solution, saturated sodium bicarbonate solution (2×) and brine, dried over sodium sulfate, and concentrated to give a foam as crude product. Trituration of the foam with ether afforded the title product as a white powder (161 mg, 55%). TLC: (methanol/methylene chloride: 1/9, silica gel): $R_f$=0.36; $^1H$ NMR ($CD_3OD$): 7.62 (d, J=8.0, 1H), 7.50 (d, J=8.2, 1H), 7.29 (t, J=8.2, 1H), 7.22 (d, J=3.0, 1H), 7.16 (s, 1H), 7.11 (t, J=7.4, 1H), 4.96–4.90 (m, 1H), 4.82–4.72 (m, 2H), 4.56 (q, J=7.1, 1H), 2.78–2.66 (m, 4H), 1.49 (d, J=7.4, 3H), 1.40 (s, 9H), 1.28 (s, 9H).

EXAMPLE 32

(3S)-3-[(1-(2'-Carboxyethyl)Indole-2-Carbonyl) Alaninyl]Amino-4-Oxobutanoic Acid, Semicarbazone (3S)-3-[(1-(3'-(1'-t-Butoxy-1'-oxo)propyl)indole-2-carbonyl)alaninyl]amino -4-oxobutanoic acid, t-butyl ester semicarbazone (140 mg, 0.24 mmol) was dissolved in anisole (0.2 mL) and methylene chloride (2 mL) and the suspension was treated with TFA (1 mL). The resulting solution was stirred for 2 hours under a nitrogen atmosphere at room temperature. The reaction mixture was concentrated and chased with methylene chloride to give a solid. Trituration of the solid with ether gave the title product as a colorless powder (107 mg, 95%). TLC: (methylene chloride:methanol:acetic acid, 8:1:1, silica gel): $R_f$=0.17; $^1H$ NMR ($CD_3OD$): δ 7.62 (d, J=8.0, 1H), 7.50 (d, J=8.2, 1H), 7.32–7.27 (m, 1H), 7.23 (d, J=3.0, 1H), 7.13–7.08 (m, 2H), 4.97–4.90 (m, 1H), 4.80–4.69 (m, 1H), 4.54 (q, J=7.1, 1H), 2.82–2.73 (m, 4H), 1.49 (d, J=7.1, 3H).

EXAMPLE 33

(3S)-3-[(1-(2'-Carboxyethyl)indole-2-Carbonyl) Alaninyl]Amino-4-Oxobutanoic Acid (3S)-3-[(1-(2'-Carboxyethyl)indole-2-carbonyl)alaninyl] amino-4-oxobutanoic acid, semicarbazone (95 mg, 0.21 mmol) was dissolved in methanol (3 mL), formaldehyde (1 mL, 37% wt. aq) and acetic acid (1 mL) and the resultant solution was stirred for 4 hours under a nitrogen atmosphere at room temperature. The reaction mixture was concentrated to remove methanol, diluted with water and extracted twice with ethyl acetate. The combined ethyl acetate solutions were washed with brine, dried over sodium sulfate and concentrated to give a glassy material which was triturated with ether to afford the title product as a slightly yellow powder (20 mg, 20%). TLC: (methylene chloride:methanol:acetic acid, 8:1:1, silica gel): $R_f$=0.26; $^1H$ NMR ($CD_3OD$): δ 7.62 (d, J=8.0, 1H), 7.51 (d, J=1H), 7.32–7.27 (m, 1H), 7.13–7.08 (m, 2H), 4.80–4.76 (m, 2H), 4.68–4.52 (m, 2H), 4.37–4.25 (m, 1H), 2.84–2.50 (m, 3H), 1.47 (d, J=7.1, 3H), 2 sets).

EXAMPLE 34

2,6-Dichlorobenzyloxyethanol

Sodium hydride (1.76 g, 0.044 mol, 60% wt. in mineral oil) was slowly added to a solution of ethylene glycol (11.2 mL) in dry THF (100 mL). The resultant mixture was stirred briefly under a nitrogen atmosphere at room temperature. α-Bromo-2,6-dichlorotoluene (9.894 g, 0.04 mol) was added to the mixture and the mixture was stirred for an additional 5.5 hours under a nitrogen atmosphere at room temperature. Additional sodium hydride (0.400 g) was added and the mixture was then stirred for 24 hours at room temperature. The reaction mixture was concentrated to remove THF, and the residue was partitioned between ether and water. The aqueous layer was back extracted with ether (2×). The combined organic solution was washed with water and brine, dried over sodium sulfate, filtered and concentrated to give a crude oil. The oil was flash chromatographed on silica gel with ethyl acetate/hexanes (10–50%) to give the title product as a yellow oil (4.56 g, 51%). TLC: (ethyl acetate/hexanes, 30/70): $R_f$=0.26. $^1$H NMR (CDCl$_3$): δ 7.35–7.18 (m, 3H), 4.84 (s, 2H), 3.76–3.66 (m, 4H).

EXAMPLE 35

5-(2',6'-Dichlorobenzyloxy)-4-Hydroxy-3-Nitropentanoic Acid, t-Butyl Ester

DMSO was added dropwise to a solution of (47.5 mL) oxalyl chloride (7.5 mL, 15.0 mmol, 2.0 M in methylene chloride) and the resultant reaction mixture was stirred for 10 min at −78° C. 2,6Dichlorobenzyloxy-ethanol (2211 mg, 10 mmol) in dry methylene chloride (5 mL) was added dropwise to the mixture and the mixture was then stirred for 15 minutes under a nitrogen atmosphere at −78° C. Triethylamine (8.4 mL, 60 mmol) was added dropwise to the reaction mixture, and the resultant mixture was stirred for 10 min at −78° C., then allowed to warm to 0° C. (over a period of approximately 20 min). A methylene chloride solution of tert-butyl 3-nitropropionate (1927 mg, 11.0 mmol in 5 mL of dry methylene chloride) was added dropwise to the reaction mixture and the mixture was stirred for 1 hour. The residue was extracted with ether and the resultant white solid was collected by filtration. The organic filtrate was washed with 5% KHSO$_4$ solution (2×) and brine, dried over sodium sulfate, and concentrated to give a crude oil (3.95 g). The oil was subjected to flash chromatography on silica gel with ethyl acetate/hexanes (1:2) to afford the title product as a yellow oil (2.917 g, 74%). TLC: (ethyl acetate, hexanes, 60/40): $R_f$=0.54.

EXAMPLE 36

3-Amino-5-(2',6'-Dichlorobenzyloxy)-4-Hydroxypentanoic Acid, t-Butyl Ester

A mixture of 5-(2',6'-dichlorobenzyloxy)-4-hydroxy-3-nitropentanoic acid t-butyl ester (2.213 g, 0.0056 mol) and wet Raney nickel (3.4 g) in methanol (150 mL) was stirred for 2 hours under a hydrogen balloon at room temperature. The reaction mixture was filtered through Celite and the filter cake was washed with methanol. The filtrate was concentrated and chased with methylene chloride to give the title product (2.078 g, 100%). TLC: (methanol/methylene chloride 1/9): $R_f$=0.21.

EXAMPLE 37

N-(1,3-Dimethylindole-2-Carbonyl)Valine

DMAP (367 mg, 3.0 mmol) and EDAC (748 mg, 3.9 mmol) were added as solids to a solution of 1,3-dimethylindole-2-carboxylic acid (568 mg, 3.3 mmol) in DMF (5 mL), and the resultant mixture was stirred for 10 minutes under a nitrogen atmosphere at 0° C. A methylene chloride solution of the methyl ester of valine (553 mg, 3.3 mmol, in 5 mL of methylene chloride) was added to the mixture, and the mixture was first stirred for one hour at 0° C. then for 5 hours at room temperature. The reaction mixture was partitioned between ethyl acetate and 5% KHSO$_4$ solution and the aqueous solution was back-extracted with ethyl acetate. The combined ethyl acetate washes were in turn washed with 5% KHSO$_4$ solution saturated sodium bicarbonate solution (2×) and brine, dried over sodium sulfate, and concentrated to give the title product as a yellow syrup (900 mg).

A 1,4-dioxane solution (5 mL) of the above yellow syrup was treated with an aqueous solution of lithium hydroxide (1.0 M LiOH, 3.0 mL) and the resultant mixture was stirred for 1 hour at room temperature (the mixture became homogeneous). The reaction mixture was acidified with 1 M hydrochloric acid and extracted with ethyl acetate (3×). The combined ethyl acetate solutions were washed with brine, dried over sodium sulfate, and concentrated to give the title product as a yellow foam (839 mg). $^1$H NMR (CD$_3$OD): δ 7.58 (dt, J=8.0, 0.8, 1H), 7.37 (dd, J=8.0, 0.8, 1H), 7.29–7.24 (m, 1H), 7.12–7.06 (m, 1H), 4.57 (d, J=5.8, 1H), 3.80 (s, 3H), 2.48 (s, 3H), 3.34–2.28 (m, 1H), 1.10 (d, J=6.9, 3H), 1.07 (d, J=6.9, 3H).

EXAMPLE 38

N-[(1,3-Dimethylindole-2-Carbonyl)Valinyl]-3-Amino-4-Hydroxy-5-(2',6'-Dichlorobenzyloxy) Pentanoic Acid, t-Butyl Ester 1-Hydroxybenzotriazole hydrate (153 mg, 1.0 mmol) and EDAC (268 mg, 1.4 mmol) were added to a methylene chloride solution of N-(1,3-dimethylindole-2-carbonyl) valine (288 mg, 1.0 mmol, in 3 mL of methylene chloride). The resultant mixture was stirred for 10 minutes under a nitrogen atmosphere at room temperature. A methylene chloride solution of 3-amino-5-(2',6'-dichlorobenzyloxy)-4-hydroxypentanoic acid, t-butyl ester (364 mg, 1.0 mmol, in 2 mL of methylene chloride) was added to the reaction mixture and the mixture was first stirred for one hour under a nitrogen atmosphere at 0° C., and then for 16 hours at room temperature. The reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2×) and brine, dried over sodium sulfate, and concentrated to give crude product (583 mg). The crude product was subjected to flash chromatography on silica gel with ethyl acetate/hexane (2/3) to give the title product as a white solid (260 mg). TLC: (ethyl acetate/hexanes 1:1): $R_f$=0.38.

EXAMPLE 39

N-[(1,3-Dimethylindole-2-Carbonyl)Valinyl]-3-Amino-4-Oxo-5-(2',6'-Dichlorobenzyloxy)Pentanoic Acid, t-Butyl Ester Dess-Martin periodinane (195 mg) was added as a solid to a solution of N-[(1,3-dimethylindole-2-carbonyl)valinyl]-3-amino-4-hydroxy-5-(2',6'-dichloro-benzyloxy)pentanoic acid, t-butyl ester (96 mg) in DMSO (1.5 ml). The resulting solution was stirred under a nitrogen atmosphere at room temperature for thirty minutes, then partitioned between EtOAc and water. The organic phase was washed with water (2×) and brine, dried (Na$_2$SO$_4$), and concentrated to give a white solid (83 mg). Flash chromatographic purification with EtOAc/hexanes (1:1) afforded the title product as a white solid (54 mg). TLC (EtOAc/hexanes; 1:1, silica gel): $R_f$=0.52.

EXAMPLE 40

N-[(1,3-Dimethylindole-2-Carbonyl)Valinyl]-3-Amino-4-Oxo-5-(2',6'-Dichlorobenzyloxy)Pentanoic Acid A solution of N-[(1,3-Dimethylindole-2-carbonyl)valinyl]-3-amino-4-oxo-5-(2',6'-dichloro-benzyloxy)pentanoic acid, t-butyl ester (49 mg) in anisole (0.2 mL) and methylene chloride (2 mL) was treated with TFA (1 mL) and stirred for 30 minutes under a nitrogen atmosphere at room temperature. The resultant solution was concentrated and chased with methylene chloride to give a white solid as the crude product. The crude product was triturated with ether to yield the title product as a white powder (34 mg). MS(EI) for $C_{28}H_{31}Cl_2N_3O_6$; MH$^+$=576/578; (MH)$^-$=574/576.

EXAMPLE 41

N-[(1,3-Dimethylindole-2-Carbonyl)Valinyl]-3-Amino-4-Hydroxy-5-Fluoropentanoic Acid, t-Butyl Ester 4-Dimethylaminopyridine (DMAP) (67 mg, 0.55 mmol) and 1-(3'-dimethylaminopropyl)-3-ethylcarbodiimide hydrochloride (EDAC) (125 mg, 0.65 mmol) were added as solids to a DMF solution of 1,3-dimethylindole-2-carboxylic acid (95 mg, 0.5 mmol in 1 mL of DMF), and the resultant reaction mixture was stirred for 10 minutes under a nitrogen atmosphere at 0° C. A methylene chloride solution of N-(valinyl)-3-amino-4-hydroxy-5-fluoropentanoic acid, t-butyl ester (153 mg, 0.5 mmol in 1 mL of methylene chloride) was added and the resultant reaction mixture was first stirred for 1 hour at 0° C. and then for 4 hours at room temperature. The reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2×), and brine, dried over sodium sulfate, and concentrated to give a solid. The solid was triturated with ether/hexane to yield the title product as a white solid (134 mg, 56%). TLC: (ethyl acetate/hexanes, 2:1): $R_f$=0.42. $^1$H NMR (CDCl$_3$): δ 7.59 (d, J=8.8, 1H), 7.37 (d, J=7.7, 1H), 7.29–7.24 (m, 1H), 7.12–7.07 (m, 1H), 4.49–4.26 (m, 5H), 3.81–3.79 (m, 3H), 2.66–2.47 (m, 5H), 2.22–2.10 (m, 1H), 1.45–1.41 (m, 9H), 1.09–1.03 (m, 6H).

EXAMPLE 42

N-[(1,3-Dimethylindole-2-Carbonyl)Valinyl]-3-Amino-4-Oxo-5-Fluoropentanoic Acid, t-Butyl Ester Dimethyl sulfoxide (0.09 mL, 1.25 mmol) was added to a solution of oxalyl chloride (0.19 mL, 2.0 M, 0.38 mmol) in methylene chloride (4 mL), and the resultant mixture was stirred for 10 minutes under a nitrogen atmosphere at −78° C. A dry methylene chloride solution of N-[1,3-dimethylindole-2-carbonyl)valinyl]-3-amino-4-hydroxy-5-fluoropentanoic acid, t-butyl ester (119 mg, 0.25 mmol in 1 mL of dry methylene chloride), was added dropwise to the mixture and the resultant reaction mixture was stirred for 15 min at −78° C. Triethylamine (0.21 mL, 1.5 mmol) was added dropwise, and the reaction mixture was then stirred for 10 minutes at −78° C. then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a crude product. The crude product was chromatographed with ethyl acetate/hexanes (2:1) on silica gel gave the title product as a white solid (48 mg, 41%). TLC: (ethyl acetate/hexanes, 2:1): $R_f$=0.58.

EXAMPLE 43

N-[(1,3-Dimethylindole-2-Carbonyl)Valinyl]-3-Amino-4-Oxo-5-Fluoropentanoic Acid

A solution of N-[(1,3-dimethylindole-2-carbonyl)valinyl]-3-amino-4-oxo-5-fluoropentanoic acid, t-butyl ester (40 mg) in anisole (0.2 mL) and methylene chloride (2 mL) was treated with trifluoroacetic acid (1 mL), and the resultant reaction mixture was stirred for 30 minutes under a nitrogen atmosphere at room temperature. The reaction mixture was concentrated and chased with methylene chloride to give a solid. The solid was triturated with ether to yield the title product as a brown powder (17 mg). TLC: (methylene chloride/methanol/acetic acid, 20:1:1): $R_f$=0.40. MS (EI) for $C_{21}H_{26}FN_3O_3$: MH$^+$=420; MH$^-$=418.

EXAMPLE 44

N-[(1-Methylindole-2-Carbonyl)Valinyl]-3-Amino-4-Hydroxy-5-Fluoronentanoic Acid, t-Butyl Ester DMAP (95 mg, 0.78 mmol) and EDAC (200 mg, 1.04 mmol) were added as solid to a solution of 1-methylindole-2-carboxylic acid (130 mg, 0.74 mmol) and N-(valinyl)-3-amino-4hydroxy-5-fluoropentanoic acid, t-butyl ester (227 mg, 0.74 mmol) in methylene chloride (5 mL), and the resultant solution was stirred for 1 hour under a nitrogen atmosphere at 0° C. and then 4 hours at room temperature. The reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2×) and brine, dried over sodium sulfate, and concentrated to give a foam. The foam was triturated with ether to yield the title product as a slightly brown solid (224 mg, 65%). TLC: (methanol/methylene chloride, 1:9): $R_f$=0.46.

EXAMPLE 45

N-[(3-Chloro-1-Methylindole-2-Carbonyl)Valinyl]-3-Amino-4-Oxo-5-Fluoropentanoic Acid, t-Butyl Ester DMSO (0.06 mL, 0.9 mmol) was added to a solution of oxalyl chloride (0.14 mL, 2.0 M, 0.28 mmol, in 4 mL of methylene chloride) and the solution was then stirred for 10 minutes under a nitrogen atmosphere at −78° C. A solution of N-[(1-methylindole-2-carbonyl)valinyl]-3-amino-4-hydroxy-5-fluoropentanoic acid, t-butyl ester (85 mg, 0.18 mmol) in dry methylene chloride (1 mL), was added dropwise to the reaction mixture and the mixture was stirred for 15 minutes at −78° C. Triethylamine (0.15 mL, 1.08 mmol) was added dropwise to the reaction mixture and the mixture was stirred for 10 minutes at −78° C. and then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% $KHSO_4$ solution and brine, dried over sodium sulfate, and concentrated to give a brown foam. The foam was triturated with ether to afford the title product as a light brown powder (64 mg). MS for $C_{24}H_{31}ClFN_3O_5$: $(MH)^-=494/496$.

EXAMPLE 46

N-[(3-Chloro-1-Methylindole-2-Carbonyl)Valinyl]-3-Amino-4-Oxo-5-Fluoropentanoic Acid A solution N-[(3-chloro-1-methylindole-2-carbonyl) valinyl]-3-amino-4-oxo-5-fluoropentanoic acid, t-butyl ester (47 mg) in anisole (0.2 mL) and methylene chloride (2 mL) was treated with TFA (1 mL) and the resultant reaction mixture was stirred for 1 hour under a nitrogen atmosphere at room temperature. The reaction mixture was concentrated and chased with methylene chloride, then triturated with ether to afford a brown powder (28 mg). The powder was subjected to flash chromatography on silica gel with methanol/methylene chloride containing a drop of acetic acid to give the title product (25 mg). TLC: (methylene chloride/methanol, 9:1): $R_f=0.29$. MS(EI) for $C_{20}H_{23}ClFN_3O_5$: $MH^+=440.442$; $M-H)^-=438/440$.

EXAMPLE 47

N-[(5-Fluoro-1-Methylindole-2-Carbonyl)Valinyl]-3-Amino-4-Hydroxy-5-Fluoropentanoic Acid, t-Butyl Ester DMAP (257 mg, 2.08 mmol) and EDAC (427 mg, 2.23 mmol) were added as solids to a solution of 5-fluoro-1-methylindole-2-carboxylic acid (359 mg, 86 mmol in 3 mL of DMF), and the resultant reaction mixture was stirred for 10 minutes under a nitrogen atmosphere at 0° C. N-(Valinyl)-3-amino-4-hydroxy-5-fluoropentanoic acid, t-butyl ester (579 mg, 1.86 mmol) in DMF (3 mL) was added and the resulting solution was stirred for 1 hour under a nitrogen atmosphere at 0° C. and 4 hours at room temperature. The reaction mixture was partitioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2x) and brine, dried over sodium sulfate, and concentrated to give the title product as a slightly yellow solid (0.827 mg). TLC: (methanol/methylene chloride, 1:9): $R_f=0.52$.

EXAMPLE 48

N-[(3-Chloro-5-Fluoro-1-Methylindole-2-Carbonyl) Valinyl]-3-Amino-4-Oxo-5-Fluoropentanoic Acid, t-Butyl Ester DMSO (0.60 mL, 8.5 mmol) was added to a methylene chloride solution of oxalyl chloride (2.1 mL, 2.0 M, 4.2 mmol, in 15 mL of methylene chloride), and the resultant reaction mixture was stirred for 10 minutes under a nitrogen atmosphere at −78° C. A methylene chloride solution of N-[(5-fluoro-1-methylindole-2-carbonyl)valinyl]-3-amino-4-hydroxy-5-fluoropentanoic acid, t-butyl ester (820 mg, 1.7 mmol, in 8 mL of dry methylene chloride), and DMSO (0.4 mL) were added dropwise to the reaction mixture and stirred for 15 minutes at −78° C. TEA (1.4 mL, 10.2 mmol) was added to the mixture dropwise and the mixture was stirred for 10 minutes at −78° C., then was allowed to warm to room temperature. The reaction mixture was partitioned between ethyl acetate and 5% $KHSO_4$ solution and the aqueous layer was back-extracted with ethyl acetate. The combined ethyl acetate solutions were washed with 5% $KHSO_4$ solution and brine, dried over sodium sulfate, and concentrated to give the title product as a slightly yellow solid. Trituration with ether afforded the title product as a white powder (705 mg, 85%). TLC: (methanol/methylene chloride, 1:9): $R_f=0.63$. MS for $C_{24}H_{30}ClF_2N_3O_5$: $MH^+=514/516$; $(M-H)^-=512/514$.

EXAMPLE 49

N-[(3-Chloro-5-Fluoro-1-Methylindole-2-Carbonyl) Valinyl]-3-Amino-4-Oxo-5-Fluoropentanoic Acid A solution of N-[(3-chloro-5-fluoro-1-methylindole-2-carbonyl)valinyl]-3-amino-4-oxo-5-fluoropentanoic acid, t-butyl ester (682 mg) in anisole (1 mL) and methylene chloride (10 mL) was treated with TFA (5 mL), and the resultant reaction mixture was stirred for 45 minutes under a nitrogen atmosphere at room temperature. The reaction mixture was concentrated and chased with methylene chloride, then triturated with ether to afford the title product as a white powder (500 mg). MS (EI) for $C_{20}H_{22}ClF_2N_3O_5$: $MH^+=458/460$; $(M-H)^-=456/458$.

EXAMPLE 50

N-[(1-(3'-Phenylpronyl)Indole-2-Carbonyl)Valinyl]-3-Amino-4Hydroxy-5-Fluoronentanoic Acid, t-Butyl Ester DMAP (122 mg, 1.0 mmol) and EDAC (249 mg 1.3 mmol) were added as solids to a DMF solution of 1-(3'-phenylpropyl)indole-2-carboxylic acid (279 mg, 1.0 mmol, 2 mL in DMF), and the resultant mixture was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to the reaction mixture and the mixture was stirred for 1 hour under a nitrogen atmosphere at 0° C. and then 4 hours at room temperature. The yellow reaction mixture was partitioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2x) and brine, dried over sodium sulfate, and concentrated to give a crude solid (0.827 g). The crude solid was subjected to flash chromatography on silica gel eluting with ethyl acetate/hexanes (1:2) afforded the title product as a slightly yellow solid (171 mg). TLC: (ethyl acetate/hexanes 2:1): $R_f=0.57$.

EXAMPLE 51

N-[(1-(3'-Phenylpropyl)Indole-2-Carbonyl)Valinyl]-3-Amino-4-Oxo-5-Fluoropentanoic Acid, t-Butyl Ester DMSO (0.11 mL, 1.5 mmol) was added to a methylene chloride solution of oxalyl chloride (0.22 mL, 2.0 M, 0.44 mmol in 3.5 mL in methylene chloride), and the resultant solution was stirred for 10 minutes under a nitrogen atmosphere at −78° C. A methylene chloride solution of N-[(1-(3'-phenylpropyl)indole-2-carbonyl)valinyl]-3-amino-4hydroxy-5-fluoropentanoic acid, t-butyl ester (169 mg, 0.3 mmol in 1.5 mL of dry methylene chloride) was added dropwise and the resulting solution stirred for 15 minutes at −78° C. Triethylamine (0.25 mL, 1.8 mmol) was added dropwise to the reaction mixture and the mixture was stirred for 10 minutes at −78° C., then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a crude product. The crude product was triturated with hexanes to yield the title product as a slightly yellow powder (129 mg, 77%). TLC: (ethyl acetate/hexanes 2:1): R$_f$=0.69.

EXAMPLE 52

N-[(1-(3'-Phenylpropyl)Indole-2-Carbonyl)Valinyl]-3-Amino-4-Oxo-5-Fluoropentanoic Acid A solution of N-[(1-(3'-phenylpropyl)indole-2-carbonyl)valinyl]-3-amino-4-oxo-5-fluoropentanoic acid, t-butyl ester (97 mg) in anisole (0.2 mL) and methylene chloride (2 mL) was treated with TFA (1 mL), and the resultant reaction mixture was stirred for 1 hour under a nitrogen atmosphere at room temperature. The reaction mixture was concentrated and chased with methylene chloride, then triturated with ether to yield the title product as a slightly yellow powder (44 mg). TLC: (methylene chloride/methanol/acetic acid, 20:1:1): R$_f$=0.4; MS (EI) for C$_{32}$H$_{40}$FN$_3$O$_5$: MH$^+$=510; (M−H)$^-$=508.

EXAMPLE 53

N-[(1-Phenylindole-2-Carbonyl)Valinyl]-3-Amino-4-Hydroxy-5-Fluoropentanoic Acid, t-Butyl Ester DMAP (122 mg, 1.0 mmol) and EDAC (249 mg, 1.3 mmol) were added as solids to a DMF solution of 1-phenylindole-2-carboxylic acid (237 mg, 1.0 mmol in 2 mL DMF), and the resultant reaction mixture was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to the reaction mixture and the mixture was stirred for 1 hour under a nitrogen atmosphere at 0° C. and 4 hours at room temperature. The yellow reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2×) and brine, dried over sodium sulfate, and concentrated to give a colorless film (0.827 g). The film was subjected to flash chromatography on silica gel with ethyl acetate/hexanes (1:2) to yield the title product as a white foam (400 mg, 78%). TLC: (ethyl acetate/hexanes 1:1): R$_f$=0.27.

EXAMPLE 54

N-[(1-Phenylindole-2-Carbonyl)Valinyl]-3-Amino-4-Oxo-5-Fluoropentanoic Acid, t-Butyl Ester DMSO (0.13 mL, 1.9 mmol) was added to a methylene chloride solution of oxalyl chloride (0.29 mL, 2.0 M, 0.58 mmol in 4 mL of methylene chloride), and the resultant solution was stirred for 10 minutes under a nitrogen atmosphere at 78° C. A methylene chloride solution of N-[(1-phenylindole-2-carbonyl)valinyl]-3-amino-4-hydroxy-5-fluoropentanoic acid, t-butyl ester (200 mg, 0.38 mmol in 2 mL of dry methylene chloride) was added dropwise and resulting mixture stirred for 15 minutes at −78° C. Triethylamine (0.30 mL, 2.1 mmol) was added dropwise to the mixture, and the resultant mixture was stirred for 10 minutes at −78° C., then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a crude product. The crude product was triturated to yield the title product as a slightly yellow powder (181 mg). TLC: (ethyl acetate/hexanes 1:1): R$_f$=0.43.

EXAMPLE 55

N-[(1-Phenylindole-2-Carbonyl)Valinyl]-3-Amino-4-Oxo-5-Fluoropentanoic Acid

A solution of N-[(1-phenylindole-2-carbonyl)valinyl]-3-amino-4-oxo-5-fluoropentanoic acid, t-butyl ester (154 mg) in anisole (0.2 mL) and methylene chloride (2 mL) was treated with TFA (1 mL), and the resultant reaction mixture was stirred for one hour under a nitrogen atmosphere at room temperature. The reaction mixture was concentrated and chased with methylene chloride, then triturated with ether to yield the title product as a white powder (100 mg). TLC: (methylene chloride/methanol/acetic acid, 20:1:1): R$_f$=0.38, MS (EI) for C$_{25}$H$_{26}$FN$_3$O$_5$: MH$^+$=468; (M−H)$^-$=466.

EXAMPLE 56

N-[1-(2'-((1'-t-Butoxy-1'-Oxo)Ethyl)Indole-2-Carbonyl)Valinyl]-3-Amino-4-Hydroxy-5-Fluoropentanoic Acid, t-Butyl Ester DMAP (122 mg, 1.0 mmol) and EDAC (249 mg, 1.3 mmol) were added as solids to a DMF solution of (1-(2'-((1'-t-butoxy-1'-oxo)ethyl)indole-2-carboxylic acid (275 mg, 1.0 mmol in 2 mL of DMF), and the resultant solution was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to it, stirred for 1 hour under a nitrogen atmosphere at 0° C. and 4 hours at room temperature. The yellow reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated with sodium bicarbonate solution (2×) and brine, dried over sodium sulfate, and concentrated to give a colorless film (0.827 g). The film was flash chromatographed on silica gel with ethyl acetate/hexane (1:1) to yield the title product as a white foam (461 mg). TLC: (ethyl acetate/hexanes 30:70): R$_f$=0.11.

EXAMPLE 57

N-[(1-(2'-((1'-t-Butoxy-1'-Oxo)Ethyl)Indole-2-Carbonyl)Valinyl]-3-Amino-4-Oxo-5-Fluoropentanoic Acid, t-Butyl Ester A mixture of N-[(1-(2'-((1'-t-butoxy-1'-5-oxo)ethyl)indole-2-carbonyl)valinyl]-3-amino-4-hydroxy-5-fluoropentanic acid, t-butyl ester (230 mg, 0.41 mmol), N-methylmorpholine N-oxide (71 mg, 0.61 mmol) and powdered molecular sieves (205 mg) in dry methylene chloride (2 mL) was stirred for 1.5 hours under a nitrogen atmosphere at room temperature. Tetra(propyl)ammonium perruthenate (7 mg) was added and the resulting mixture was stirred for 2 hours under a nitrogen atmosphere at room temperature. The reaction mixture was filtered through silica gel with ethyl acetate as the eluent. The filtrate was concentrated and chromatographed on silica gel with ethyl acetate/hexanes (approximately 1:2 to approximately 1:1) to yield the title product as a yellow oil (100 mg). TLC: (ethyl acetate/hexanes 30/70): $R_f$=0.27.

EXAMPLE 58

N-[(1-(Carboxymethyl)Indole-2-Carbonyl)Valinyl]-3-Amino-4-Oxo-5-Fluoropentanoic Acid A solution of N[(1-(2'-((1'-t-butoxy-1'-oxo)ethyl)indole-2-carbonyl)valinyl]-3-amino-4-oxo-5-fluoropentanoic acid, t-butyl ester (100 mg) in anisole (0.2 mL) and methylene chloride (2 mL) was treated with TFA (1 mL). The resultant reaction mixture was stirred for 30 minutes under a nitrogen atmosphere at room temperature. The reaction mixture was concentrated and chased with methylene chloride, then triturated with ether to yield the title product as a light yellow powder (26 mg). TLC: (methylene chloride/methanol, 8:1:1): $R_f$=0.32. MS (EI) for $C_{21}H_{24}FN_3O_7$: MH$^+$=450; (M–H$^-$=448.

EXAMPLE 59

N-[(1-Methylindole-2-carbonyl)valinyl]-3-amino-4-hydroxy-5-fluoropentanoic Acid, t-Butyl Ester To a solution of 1-methylindole-2-carboxylic acid (130 mg, 0.74 mmol) and N-(valinyl)-3-amino-4-hydroxy-5-fluoropentanoic acid, tert-butyl ester in methylene chloride (5 mL) and cooled to 0° C. Solid 4-dimethylaminopyridine (DMAP) (95 mg, 0.78 mmol) and 1-(3'-dimethylaminopropyl)-3-ethylcarbodiimide hydrochloride (EDAC) (200 mg, 1.04 mmol) were added to the solution at 0° C. The reaction mixture was stirred at 0° C. for 1 h and allowed to warm slowly to room temperature. After 4 h the reaction was partitioned between ethyl acetate (EtOAc) and 5% KHSO$_4$ aqueous solution. The organic layer was washed with 5% KHSO$_4$ solution, saturated sodium bicarbonate solution, brine, dried (Na$_2$SO$_4$) and concentrated to a foam. The crude residue was triturated with diethyl ether and the solid filtered to afford the title compound as a light brown solid (224 mg, 65% yield). TLC(MeOH:CH$_2$Cl$_2$, 1:9): $R_f$=0.46.

EXAMPLE 60

N-[(1-Methylindole-2-carbonyl)valinyl]-3-amino-4-oxo-5-fluoropentanoic Acid, t-Butyl Ester To a solution of N-[(1-methylindole-2-carbonyl)valinyl]-3-amino-4-hydroxy-5-fluoropentanoic acid, t-butyl ester (51 mg, 0.11 mmol) in DMSO(1 mL) was added Dess-Martin periodinane (110 mg). After 30 min at room temperature the reaction mixture was partitioned between ethyl acetate and water. The organic layer was washed with water and brine, dried and concentrated to a white solid. Trituration with diethyl ether and collection of the solid afforded the title compound as a white powder (25 mg, 49% yield). TLC (MeOH:CH$_2$Cl$_2$, 5:95): $R_f$=0.48.

EXAMPLE 61

N-[(1-Methylindole-2-carbonyl)valinyl]-3-amino-4-oxo-5-fluoropentanoic Acid

A solution of N-[(1-methylindole-2-carbonyl)valinyl]-3-amino-4-oxo-5-fluoropentanoic acid, t-butyl ester (19 mg, 0.041 mmol) and anisole (0.1 mL) in CH$_2$Cl$_2$ (1 mL) was treated with trifluoroacetic acid (0.5 mL) at room temperature. After 30 min the reaction mixture was concentrated and chased with methylene chloride. The crude residue was triturated with diethyl ether and the solid filtered to afford the title compound as a light brown solid (12 mg, 72% yield). TLC(AcOH:MeOH:CH$_2$Cl$_2$, 1:1:20): $R_f$=0.59. Mass Spectrum for $C_{20}H_{24}FN_3O_5$: [MH]$^+$ 406, [MH]$^-$ 404.

Following the methods set down in Examples 59–61, the following compounds were prepared:

EXAMPLE 62

N-[(1,3-Dimethyl-5-fluoroindole-2-carbonyl) valinyl]-3-amino-4-oxo-5-fluoropentanoic Acid 57% yield; TLC(MeOH:CH$_2$Cl$_2$, 5:95): $R_f$=0.56. Mass Spectrum for $C_{21}H_{25}F_2N_3O_5$: [MH]$^+$ 438, [MH]$^-$ 436.

EXAMPLE 63

N-[(1-Homoallylindole-2-carbonyl)valinyl]-3-amino-4-oxo-5-fluoropentanoic Acid

29% yield; TLC(MeOH:CH$_2$Cl$_2$, 1:9): $R_f$=0.33. Mass Spectrum for $C_{23}H_{28}FN_3O_5$: [MH]$^+$ 446, [MNa]$^+$ 468, [MH]$^-$ 444.

EXAMPLE 64

N-[(1-Methyl-5-fluoroindole-2-carbonyl)valinyl]-3-amino-4-oxo-5-fluoropentanoic Acid 89% yield; TLC(MeOH:CH$_2$Cl$_2$, 9:1): $R_f$=0.14. Mass Spectrum for $C_{20}H_{23}F_2N_3O_5$: [MH]$^+$ 424, [MH]– 422.

EXAMPLE 65

N-[(1-Methyl-3-isobutylindole-2-carbonyl)valinyl]-3-amino-4-oxo-5-fluoropentanoic Acid 50% yield; TLC(MeOH:CH$_2$Cl$_2$, 9:1): $R_f$=0.20. Mass Spectrum for $C_{24}H_{32}FN_3O_5$: [MH]$^+$ 462, [MH]$^-$ 460.

EXAMPLE 66

N-[(1-Methyl-3-phenethylindole-2-carbonyl)valinyl-3-amino-4-oxo-5-fluoropentanoic Acid 38% yield; TLC(ethyl acetate: hexanes, 1:1): $R_f$=0.19. Mass Spectrum for $C_{28}H_{32}FN_3O_5$: [MH]$^+$ 510, [MH]$^-$ 508.

EXAMPLE 67

N-[(1-Methyl-5-Obenzylindole-2-carbonyl)valinyl]-3-amino-4-oxo-5-fluoronentanoic Acid 78% yield; TLC(ethyl acetate: hexanes, 1:1): $R_f$=0.17. Mass Spectrum for $C_{27}H_{30}FN_3O_6$: [MH]$^+$ 512, [MH]$^-$ 510.

EXAMPLE 68

N-(1,3-Dimethyl-indole-2-carbonyl)-valinyl-3-amino-5-bromo-4-oxo-pentanoic Acid, t-Butyl Ester 1-Hydroxybenzotriazole hydrate (3.19 g, 20.8 mmol) and 1-(3'-dimethylaminopropyl)-3-ethylcarbodiimide hydrochloride (EDAC) (5.60 g, 29.2 mmol) were added to a stirred solution of N-carbobenzyloxycarbonyl valine (5.24 g, 20.8 mmol) in methylene chloride/dimethyl formamide (DMF) (60 ml/30 ml) at 0° C. under nitrogen. After 15 min, aspartic acid α-methyl, β-tert-butyl diester (5.00 g, 20.8 mmol) was added as a solid followed by neat 4-methylmorpholine (2.40 ml, 21.8 mmol). After stirring at 0° C. for 1 hour and at room temperature for 5 hours, the mixture was partitioned between ethyl acetate and 5% $KHSO_4$ solution. The aqueous solution was back-extracted with ethyl acetate and the combined extracts were washed with saturated $NaHCO_3$ and brine, dried over sodium sulfate, and concentrated to give a solid. Trituration with ether afforded of N-[carbobenzyloxycarbonyl valinyl] aspartic acid, α-methyl, β-tert-butyl diester as a white solid (8.36 g, 92%). TLC($CH_2Cl_2$/MeOH, 95/5): $R_f$=0.48.

A solution of the above product (4.00 g, 9.17 mmol) in 200 ml of methanol was stirred with palladium on activated carbon (0.45 g) under an atomosphere of hydrogen (1 atm) for 50 min. The reaction mixture was then filtered through a pad of Celite and the filter cake was washed with methanol and methylene chloride. The filtrates were combined and concentrated, and the residue was chased with methylene chloride to give N-[valinyl]aspartic acid, α-methyl, β-tert-butyl diester a white solid (2.75 g, 99%). TLC ($CH_2Cl_2$/MeOH, 95/5): $R_f$=0.10.

To a turbid mixture of the above product (2.75 g, 9.11 mmol) and 1,3-dimethylindole-2-carboxylic acid (1.95 g, 10.3 mmol) in DMF (30 ml) was added 4-dimethylaminopyridine (DMAP) (1.26 g, 10.3 mmol) and 1-(3'-dimethylaminopropyl)-3-ethylcarbodiimide hydrochloride (EDAC) (2.37 g, 12.4 mmol). The reaction mixture was stirred under a nitrogen atmosphere at 0° C. for 1 hour and at room temperature for 3 hours. The reaction mixture was then partitioned between ethyl acetate and 5% $KHSO_4$ solution and the aqueous solution was back-extracted with ethyl acetate. The combined extracts were washed with saturated $NaHCO_3$ solution, water, and brine, dried over sodium sulfate, and concentrated to give a solid. The solid was triturated with ether to give N-[(1,3-dimethyl-indole-2-carbonyl)valinyl]aspartic acid, α-methyl, β-tert-butyl diester as a white powder (2.87 g, 67%). TLC ($CH_2Cl_2$/MeOH, 95/5): $R_f$=0.59.

An aqueous solution of lithium hydroxide (1.0 M, 2.98 ml) was added dropwise to a suspension the above product (1.41 g, 2.98 mmol) in 1,4-dioxane (10 ml). After stirring at room temperature for 30 min, the resulting clear was acidified with 1 N hydrochloric acid solution and diluted with water. The resulting white precipitate was collected by suction filtration and washed successively with water and with a small amount of ether, affording N-[(1,3-dimethyl-indole-2-carbonyl)-valinyl]aspartic acid, β-tert-butyl ester as a white powder (1.18 g, 86%). TLC($CH_2Cl_2$/MeOH, 90/10): $R_f$=0.21.

To a solution of the above product (1.03 g, 2.24 mmol) and 4-methylmorphorline (0.35 ml, 3.14 mmol) in THF (20 mL) at −10° C. under nitrogen was added dropwise isobutyl chloroformate (0.380 ml, 2.92 mmol). The reaction mixture was stirred under nitrogen at −10° C. for 15 min and filtered. The filter cake was washed with dry THF and the filtrates were combined and cooled to 0° C. The filtrates were then treated with a freshly prepared ether solution of diazomethane (excess). After the mixture was stirred at 0° C. for 1 hour, a mixture of hydrobromic acid (48% wt. aq. solution) and acetic acid (6 ml, 1/1) was added dropwise till the gas evolution ceased. After another 5 min, the reaction mixture was concentrated and partitioned between ethyl acetate and water. The aqueous layer was back-extracted with ethyl acetate. The organic layers were combined, washed with water, saturated $NaHCO_3$ solution, and brine, dried over sodium sulfate, and concentrated. The residue was triturated with ether to give the title compound as a white powder (1.00 g, 83%). TLC($CH_2Cl_2$/MeOH, 95/5): $R_f$=0.88.

EXAMPLE 69

N-[(1,3-Dimethyl-indole-2-carbonyl)-Valinyl]-3-amino-5-(2,6-dichlorobenzoyl)oxy-4-oxo-pentanoic Acid, t-Butyl Ester To a mixture of 2,6-dichlorobenzoic acid (0.023 g, 0.12 mmol) and potassium fluoride (0.015 g, 0.25 mmol) at room temperature under nitrogen was added N-[(1,3-dimethyl-indole-2-carbonyl)valinyl]-3-amino-5-bromo-4-oxo-pentanoic acid, tert-butyl ester (0.054 g, 0.10 mmol) in one portion. After stirring at room temperature for further 16 hrs, the mixture was partitioned between ethyl acetate and water. The organic layer was washed with water, saturated $NaHCO_3$ solution, and brine, dried over sodium sulfate, and concentrated. Trituration with ether gave the title compound as a white powder (0.051 g, 79%). TLC($CH_2Cl_2$/MeOH, 95/5): $R_f$=0.88.

EXAMPLE 70

N-[N-(1,3-Dimethyl-indole-2-carbonyl)-Valinyl]-3-amino-5-(2,6-dichlorobenzoyl)oxy-4-oxo-pentanoic Acid Trifluoroacetic acid (2 mL) was added to a stirred solution of N-(1,3-dimethyl-indole-2-carbonyl)-valinyl-3-amino-5-(2,6-dichlorobenzoyl)oxy-4-oxo-pentanoic acid, t-butyl ester (0.0340 g, 0.0526 mmol) in methylene chloride containing anisole (0.2 mL). The reaction mixture was stirred at room temperature under nitrogen for half an hour and concentrated. The residue was azeotroped with methylene chloride and triturated with ether to give the title compound as a white powder (0.0270 g, 87%). TLC($CH_2Cl_2$/MeOH/AcOH, 20/1/1): $R_f$=0.43. MS for $C_{28}H_{29}Cl_2N_3O_7$, $[MH]^+$ 590/592, $[MH]^-$ 588/590.

Following the methods set down in Examples 69–70, the following compounds were prepared:

EXAMPLE 71

N-(1,3-Dimethyl-indole-2-carbonyl)-Valinyl-3-amino-5-(diphenylphosphinyl)oxy-4oxo-pentanoic Acid 24% yield; TLC($CH_2Cl_2$/MeOH/AcOH, 20/1/1): $R_f$=0.31. MS for $C_{33}H_{36}PN_3O_7$, $[MH]^+$ 618, $[MN]^-$ 616.

EXAMPLE 72

N-(1,3-Dimethyl-indole-2-carbonyl-Valinyl-3-amino-5-(1-phenyl-3-(trifluoromethyl)pyrazol-5-yl)oxy-4-oxo-pentanoic Acid 49% yield; TLC($CH_2Cl_2$/MeOH, 90/10): $R_f$=0.29. MS for $C_{31}H_{32}F_3N_5O_6$, $[MH]^+$ 628, $[MH]^-$ 626.

EXAMPLE 73

N-(1,3-Dimethyl-indole-2-carbonyl)-Valinyl-3-amino-5-(3-(N-phenyl)aminocarbonyl-2-naphthyl)oxy-4-oxo-pentanoic Acid 68% yield; TLC($CH_2Cl_2$/MeOH, 80/20): $R_f$=0.46. MS for $C_{38}H_{38}N_4O_7$, $[MH]^+$ 663, $[MH]^-$ 661.

EXAMPLE 74

N-(1,3-Dimethyl-indole-2-carbonyl)-Valinyl-3-amino-5-(2-aminocarbonyl-1-phenyl)oxy-4-oxo-pentanoic Acid 61% yield; TLC($CH_2Cl_2$/MeOH/HOAc, 8/1/1): $R_f$=0.32. MS for $C_{28}H_{32}N_4O_7$, $[MH]^+$ 537, $[MH]^-$ 535.

EXAMPLE 75

N-(1,3-Dimethyl-indole-2-carbonyl)-Valinyl-3-amino-5-(dimethylphosphinyl)oxy-4-oxo-pentanoic Acid 76% yield; TLC(CH$_2$Cl$_2$/MeOH, 90/10): R$_f$=0.12. MS for C$_{23}$H$_{32}$PN$_3$O$_7$, [MH]$^+$ 494, [MH]$^-$ 492.

EXAMPLE 76

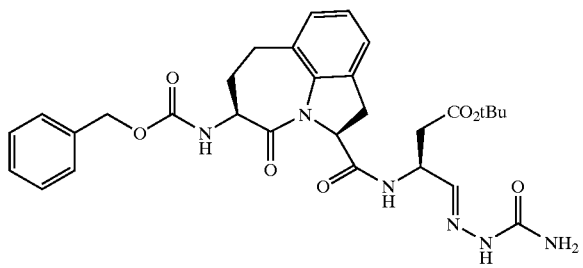

(2S-cis)-[5-Benzyloxycarbonylamino-1,2,4,5,6,7-Hexahydro-4-Oxoazepino[3,2,1-hi]indole-2-Carbonyl)amino]-4-Oxo-butanoic Acid tert-Butyl Ester Semicarbazone 1. Preparation of (2S-cis)-5-Benzyloxycarbonylamino-1,2,4,5,6,7-Hexahydro-4-Oxoazepino[3,2,1-hi]indole-2-Carboxylic Acid, Ethyl Ester To a solution of (2S-cis)-5-amino-1,2,4,5,6,7-hexahydro-4-oxoazepino[3,2,1-hi]indole-2-carboxylic acid, ethyl ester (0.437 g, 1.73 mmol, prepared as described in Tetrahedron Letters 36, pp. 1593–1596 (1995) and U.S. Pat. No. 5,504,080 (Apr. 2, 1996)) in methylene chloride (4 mL) stirring at 0° C. was added benzyl chloroformate (0.370 mL, 2.6 mmol) and triethylamine (0.724 mL, 5.2 mmol) and the resulting mixture was stirred under nitrogen for 45 minutes. The reaction was quenched with water then partitioned between ethyl acetate and 5% aqueous potassium bisulfate solution. The aqueous layer was back-extracted two times with ethyl acetate, then the combined organic layers were washed with saturated sodium chloride solution, dried over sodium sulfate and evaporated to dryness. Purification of the crude product by flash chromatography on silica gel (S/P brand silica gel 60 Å, 230–400 mesh ASTM) eluting with ethyl acetate-hexane (2:1) gave 0.558 g (68%) of crude product. Trituration with ethyl acetate-hexane (1:4) gave 0.480 g of the title compound as white solid; m.p.: 139–140° C. TLC (ethyl acetate-hexane, 2:1): Rf=0.6; $^1$H-NMR (300 MHz, CDCl$_3$): δ 7.35–7.30 (m, 5H), 7.02–6.94 (m, 3H), 6.17 (d, J=5.4 Hz, 1H), 4.15 (q, J=7.1 Hz, 2H), 3.46 (dd, J=11.0, 16.7 Hz, 1H), 3.29 (m, 1H), 3.10 (d, J=116.5, 2H), 2.35 (m, 1H), 2.16 (m, 1H), 1.23 (t, J=7.2 Hz, 3H).

2. Preparation of (2S-cis)-5-Benzyloxycarbonylamino-1,2,4,5,6,7-Hexahydro-4-Oxoazepino[3,2,1-hi]indole-2-Carboxylic Acid To a solution of (2S-cis)-5-benzyloxycarbonylamino-1,2,4,5,6,7-hexahydro-4-oxoazepino[3,2,1-hi]indole-2-carboxylic acid, ethyl ester, (0.428 g, 1.05 mmol) in 1,4-dioxane (7.5 mL) and water (2.5 mL) was added 1M aqueous lithium hydroxide (1.6 mL, 1.6 mmol) and the resulting mixture was stirred at room temperature under nitrogen for 30 minutes. The reaction mixture was acidified to pH 3 with a 5% aqueous potassium bisulfate sodium chloride solution. The aqueous layer was back-extracted two times with ethyl acetate, and the combined organic layers were dried over sodium sulfate and evaporated to dryness to yield 0.395 g (99%) of title compound as a fine white solid; m.p.: 188–189° C. TLC (methylene chloride-methanol-acetic acid, 9:1:1): Rf=0.55; $^1$H-NMR (300 MHz, CDCl$_3$) δ 7.34–7.26 (m, 5H), 7.07–6.97 (m, 3H), 6.08 (d, J=5.7 Hz, 1H), 5.25 (dd, J=9.8 Hz, 1H), 5.10 (s, 2H), 4.30 (m, 1H), 3.36 (m, 1H), 3.26 (m, 2H), 3.06 (d, J=12.0 Hz, 1H), 2.36 (m, 1H), 2.09 (m, 1H).

3. Preparation of N-(Benzyloxycarbonyl)-L-(N'-Methyl-N'-Methoxy)aspartamide β-(tert-Butyl Ester)

To a solution of N-(benzyloxycarbonyl)-L-aspartic acid-β-(tert-butyl)ester (14.65 g, 45.3 mmol, Bachem) in CH$_2$Cl$_2$ (150 mL) at 0° C. (ice bath) under a nitrogen atmosphere was added 1-hydroxybenzotriazole hydrate (7.29 g, 47.6 mmol, Aldrich) followed by 1-ethyl-3-(3',3'-dimethyl-1'-aminopropyl)carbodiimide hydrochloride (9.55 g, 49.8 mmol, Sigma). After stirring at 0° C. for 15 min., N,O-dimethylhydroxylamine hydrochloride (5.10 g, 52.3 mmol, Aldrich) and N-methylmorpholine (5.8 mL, 53 mmol, Aldrich) were added. The mixture was allowed to warm to room temperature over 3 hours then stirred at room temperature for 16 hours. The solution was concentrated under vacuum and the residue partitioned between ethyl acetate-5% KHSO$_4$ (200 mL each). The organic phase was washed in turn with 5% KHSO$_4$, saturated sodium bicarbonate and saturated sodium chloride solutions; dried over anhydrous sodium sulfate and evaporated to an oil. The oil was crystallized from hexane to give the title product (16.10 g, 97% yield) as a fluffy white crystalline solid. TLC (ethyl acetate), single spot (UV and PMA): Rf=0.37.

A similar procedure to the one above, starting with 29.3 g of N-(benzyloxycarbonyl)-L-aspartic acid-β-(tert-butyl) ester (2-fold scale up) gave 31.18 g (94% yield) of the title product.

4. Prearation of N-(Benzyloxycarbonyl)-L-Aspartic Acid Semicarbazone β-(tert-Butyl)Ester To a solution of N-(benzyloxycarbonyl)-L-(N'-methyl-N'-methoxy)aspartamide β-(tert-butyl ester) (15.50 g, 42.3 mmol) in anhydrous ether (400 mL) at 0° C. (ice bath) under a nitrogen atmosphere was added dropwise to a 1.0 M solution of LiAlH$_4$ in ether (22.0 mL, 22.0 mmol, Aldrich) at such a rate as to keep the reaction solution temperature between 0–5° C. (addition time 15–20 min). After the addition of the lithium aluminum hydride reagent was complete, the mixture was stirred at 0–5° C. for 1 hr, then quenched by the dropwise addition of 0.3 N KHSO$_4$ solution (100 mL). The resultant mixture was transferred to a separatory funnel adding sufficient 5% KHSO$_4$ solution (75 mL) to dissolve the solids. The organic phase was separated and the combined aqueous washes back-extracted with ether (100 mL). The combined ether extracts were washed with saturated NaCl solution, dried over anhydrous sodium sulfate and concentrated in vacuo with minimal heating. TLC (ethyl acetate): streaky spot (UV and PMA) Rf=0.48. TLC (methanol/methylene chloride, 1:9) major spot (UV and PMA): Rf=0.75.

The crude aldehyde was immediately taken up in aqueous ethanol (45 mL water/105 mL alcohol), placed in an ice bath and treated with sodium acetate (3.82 g, 46.6 mmol) and semicarbazide hydrochloride (5.20 g, 46.6 mmol, Aldrich). The mixture was stirred at 0° C. (ice bath) under a nitrogen atmosphere for 3 hrs, allowed to warm to room temperature, and stirred overnight (16 hrs). Most of the ethanol was removed under vacuum and the residue partitioned between ethyl acetate and water (100 mL each). The organic phase was washed sequentially with 5% KHSO$_4$, saturated sodium bicarbonate and saturated sodium chloride solutions; dried over anhydrous sodium sulfate and evaporated to dryness.

The crude product of this reaction was combined with that of two similar procedures starting with 15.40 g and 4.625 g of N-(benzyloxycarbonyl)-L-(N'-methyl-N'-methoxy) aspartamide b-(tert-butyl ester) (total 35.525 g, 97 mmol) and these combined products were purified by flash chromotagraphy on silica gel eluting with acetone/methylene chloride (3:7) then methanol-acetone-methylene chloride (0.5:3:7) to give pure title product (27.73 g, 78.5%) as a colorless foam. TLC (MeOH-CH$_2$Cl$_2$, 1:9): single spot (UV and PMA), Rf=0.51.

5. Preparation of L-Aspartic Acid Semicarbazone β-(tert-Butyl) Ester, p-Toluenesulfonate Salt To a solution of N-(benzyloxycarbonyl)-L-aspartic acid semicarbazone β-(tert-butyl)ester (13.84 g, 38.0 mmol) in absolute ethanol (250 mL) was added 10% Pd/C (1.50 g, Aldrich) and the resulting mixture stirred under an atmosphere of hydrogen (balloon) until TLC (methanol/methylene chloride, 1:9) indicated complete consumption of the starting material (60 min). Note: It is important to follow this reaction closely since the product can be over-reduced. The mixture was filtered though Celite and evaporated to an oil. The oil was chased with methylene chloride (2×75 mL) then with methylene chloride/toluene (1:1, 75 mL) to give the crude amine as a white crystalline solid. TLC (EtOAc-pyridine-AcOH-H$_2$O; 60:20:5:10) single spot (UV and PMA) Rf=0.24. Note: In this TLC system, any over-reduced product will show up immediately below the desired product, Rf=0.18 (PMA only).

The crude amine was taken up in CH$_3$CN (60 mL) and treated with a solution of p-toluenesulfonic acid monohydrate (7.22 g, 38.0 mmol) in acetonitrile (60 mL). The crystalline precipitate was collected, washed with acetonitrile and ether, and air-dried to give the title compound (13.95 g, 92% yield) as a white, crystalline solid.

The optical purity of this material was checked by conversion to the corresponding Mosher amide [1.05 equiv (R)-(-)-α-methoxy-α-(trifluoromethyl)phenylacetyl chloride, 2.1 equivalents of i-Pr$_2$NEt in CH$_2$Cl$_2$, room temperature, 30 min]. The desired product has a doublet at 7.13 ppm (1H, d, J=2.4 Hz, CH=N) while the corresponding signal for its diastereomer is at 7.07 ppm. The optical purity of the title compound obtained from the above procedure is typically >95:5.

6. (2S-cis)-[5-Benzyloxycarbonylamino-1,2,4,5,6,7-Hexahydro-4-Oxoazepino[3,2,1-hi]indole-2-Carbonyl) amino]-4-Oxo-butanoic Acid tert-Butyl Ester Semicarbazone To a solution of (2S-cis)-5-benzyloxycarbonylamnino-1,2,4,5,6,7-hexahydro-4-oxoazepino[3,2,1-hi]indole-2-carboxylic acid (0.375 g, 0.989 mmol) in methylene chloride (7 mL) stirring at 0° C. under nitrogen was added 1-hydroxybenzotriazole hydrate (0.182 g, 1.19 mmol) and 1-ethyl-3-(3',3'-dimethyl-1'-aminopropyl)carbodiimide hydrochloride (0.284 g, 1.48 mmol). After 15 minutes L-aspartic acid semicarbazone b-(tert-butyl) ester, p-toluenesulfonate salt (0.386 g, 0.989 mmol) and N-methylmorpholine (0.163 mL, 1.48 mmol) were added and the resultant reaction mixture allowed to come to room temperature within 1 hour. After stirring overnight, the reaction mixture was diluted with ethyl acetate and washed successively with 5% potassium bisulfate and saturated sodium chloride solutions; dried over sodium sulfate and evaporated to dryness. Purification of the crude product by flash chromatography on silica gel (S/P brand silica gel 60 Å, 230–400 mesh ASTM) eluting with 2% methanol-methylene chloride gave 0.463 g (79%) of the title compound as a white foam. TLC (methylene chloride-methanol, 9:1): Rf-0.5. $^1$H-NMR (300 MHz, CDCl$_3$): δ 8.42 (s,1H), 7.82 (d, J=8.1 Hz, 1H), 7.32 (m, 5H), 7.07 (m, 3H), 5.94 (d, J=6.3 Hz, 1H), 5.26 (d, J=9 Hz, 1H), 5.10 (s, 2H), 4.82 (m, 1H), 4.35 (m, 1H), 3.56 (d, J=18 Hz, 1H), 3.27 (m, 2H), 3.07 (m, 1H), 2.64 (dd, J=4.7, 15.8 Hz, 1H), 2.44 (dd, J=6.6, 15.9 Hz, 2H), 2.22 (m, 1H), 1.30 (s, 9H). Mass spectrum: m/z 593 (M+H).

EXAMPLE 77

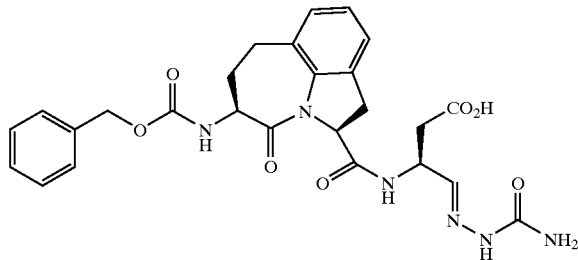

(2-cis)-[5-Benzyloxycarbonylamino-1,2,4,5,6,7-hexadydro-4-oxoazepino[3,2,1-hi]indole-2-carbonyl)-amino]-4-oxo-butanoic Acid Semicarbazone To a solution of (2S-cis)-[5-benzyloxycarbonylaio-1,2,4,5,6,7-bexahydro-4-oxoazepino[3,2,1-hi]indole-2-carbonyl) amino]-4-oxo-butanoic acid tert-butyl ester semicarbazone (0.214 g, 0.362 mmol) in methylene chloride (1.5 mL) was added anisole (0.5 mL, 4.34 mmol) followed by tirfluoroacetic acid (0.75 mL). After stirring at room temperature under nitrogen for 2 hours the reaction mixture was diluted with methylene chloride and evaporated, then chased twice with methylene chloride to give the title compound (0.195 g). TLC (methylene chloride-methanol, 95:5), Rf=0.2. $^1$H-NMR (300 MHz, CDCl$_3$) δ 9.77 (bs, 1H), 8.32 (d, J=12 Hz, 1H), 8.12 (d, J-7.8 Hz, 1 Hz), 7.31–7.27 (m, 5H) 7.13–7.04 (m, 3H), 6.64 (m, 1H) 5.32 (d, J=9.9 Hz, 1H), 5.12 (s, 2H), 4.86 (m, 1H), 4.41 (m, 1H), 3.56 (d, J=15 Hz, 1H), 3.25 (m, 2H), 3.10 (m, 2H), 2.64 (m, 2H), 2.28 (m, 2H).

EXAMPLE 78

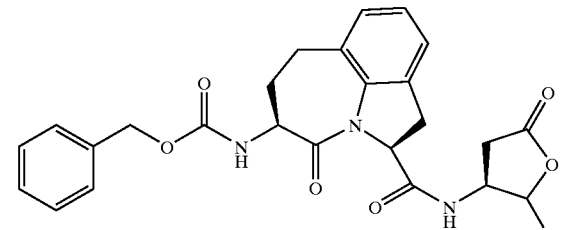

(2S-cis)-5-[Benzyloxycarbonylamino-1,2,4,5,6,7-hexahydro-4-oxoazepino[3,2,1 -hi]indole-2-carbonyl)-amino]-4-oxo-butanoic Acid (2-cis)-[5-Benzyloxycarbonylamino-1,2,4,5,6,7-hexadydro-4-oxoazepino[3,2,1-hi]indole-2-carbonyl)-amino]-4-oxo-butanoic acid semicarbazone (0.195 g, 0.36 mmol) was treated with a 3:1:1 solution of methanol-acetic acid-37% formaldehyde (2 mL) and the resulting mixture stirred under nitrogen for 1.5 hours. The reaction mixture was diluted with water, methanol removed by evaporation, then the remaining mixture lyophilized. Purification of the crude product by flash chromatography on reverse phase gel (MCI gel, CHP-20P, 75–150 micron)eluting with a 10%–80% methanol-water gradient gave 0.073 g, (42%) of the title compound as a white solid after lyophilization; m.p. 101–104° C. TLC (methylene chloride-methanol-acetic acid, 97:2.5:0.5) Rf=0.45. $^1$H-NMR (300 MHz, CDCl$_3$) δ 7.45 (m, 1H), 7.30 (s, 5H), 7.07 (d, J=3.3 Hz, 1H), 7.00 (d, J=4.8 Hz, 2H), 6.12 (m, 1H), 5.17 (d, J=9.6 Hz, 1H), 5.07 (s, 2H), 4.49 (m, 1H), 4.28 (m, 1H), 3.46 (d, J=9.9 Hz, 1H), 3.30–3.12 (m, 2H), 3.04–2.99 (m, 1H), 2.83–2.76 (m, 1H), 2.46–2.33 (m, 2H), 2.03 (bs, 1H). Mass spectrum: m/z 480 (M+H).

EXAMPLE 79

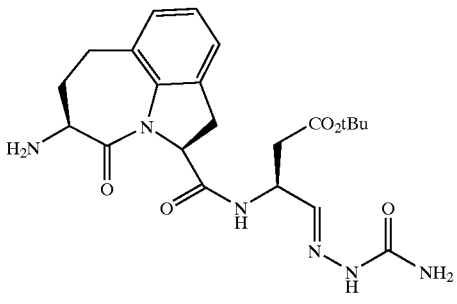

(2S-cis)-[5-Amino-1,2,3,4,5,6,7-hexahydro-4-oxoazepino[3,2,1-hi]indole-2-carbonyl)-amino]-4-oxo-butanoic Acid tert-Butyl Ester Semicarbazone 10% Palladium on carbon (0.180 g) was added to a solution of (2S-cis)-[5-benzyloxycarbonylamino-1,2,3,4,5,6,7-hexahydro-4-oxoazepino[3,2,1-hi]indole-2-carbonyl)-amino]-4-oxo-butanoic acid tert-butyl ester semicarbazone (0.308 g, 0.520 mmol) in methanol (27 mL) and the resulting mixture was hydrogenated using a balloon of hydrogen (1 atm, R.T.) for 18 hours. The mixture was filtered through Celite, evaporated to dryness, then chased two times with toluene to give the title compound as an off-white solid (0.215 g). TLC (methylene chloride-methanol, 9:1) Rf=0.15. $^1$H-NMR (300 MHz, CDCl$_3$) δ 8.53 (s, 1H), 7.89 (d, J=7.6 Hz, 1H), 7.13 (m, 3H), 5.21 (dd, J=2.3, 10.14 Hz, 1H), 4.82 (m, 1H), 3.52 (m, 1H), 3.24 (dd, J=10.3, 16.3 Hz, 1H), 3.03 (m, 2H), 2.62 & 2.42 (AB, dd, J=4.2, 7.1, 15.7 Hz, 2H), 2.19 (m, 1H), 1.32 (s, 9H).

EXAMPLE 80

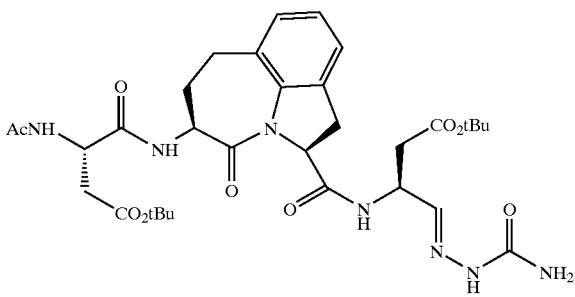

(2S-cis)-[5-(N-Acetyl-(S)-aspartyl-b-tert-butyl ester) amino-1,2,3,4,5,6,7-hexahydro-4-oxoazepino[3,2,1-hi]indole-2-carbonyl)-amino]-4-oxo-butanoic Acid tert-Butyl Ester semicarbazone To a solution of N-acetyl aspartic acid, β-tert-butyl ester (0.120 g, 0.517 mmol) in methylene chloride (1.5 mL) stirring at 0° C. under nitrogen was added 1-hydroxybenzotriazole hydrate (0.086 g, 0.564 mmol) and 1-(3-dimethylaminopropyl)-3-ethylcarbodiimnide hydrochloride (0.135 g, 0.705 mmol). After 15 minutes, a solution of (2S-cis)-[5-amino-1,2,3,4,5,6,7-hexahydro-4-oxoazepino [3,2,1-hi]indole-2-carbonyl)-amino]-4-oxo-butanoic acid tert-butyl ester semicarbazone (0.213 g, 0.47 mmol) in methylene chloride (2 mL) was added and the reaction was allowed to come to room temperature over 1 hour. After stiring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM) eluting with 5% then 10% methanol-methylene chloride gave 0.126 g (41%) of the title compound as a white solid. TLC (methylene chloride-methanol, 9:1) Rf=0.4. $^1$H-NMR (300 MHz, CDCl$_3$) δ 9.63 (s, 1H), 8.32 (d, J=7.8 Hz, 1H), 7.82 (d, J=6.6 Hz, 1H), 7.53 (d, J=4.8 Hz, 1H), 7.09 (m, 1H), 7.00 (m, 2H), 5.18 (d, J=8.1 Hz, 1H), 4.86 (m, 1H), 4.39 (m, 1H), 3.01 (m, 1H), 2.92 (dd, J=4.2, 14.7 Hz, 1H) 2.68 (d, J=12.3 Hz, 1H), 2.52 (m, 2H), 2.51 (m, 2H), 2.03 (s, 3H), 1.39 (s, 9H), 1.24 (s, 9H).

EXAMPLE 81

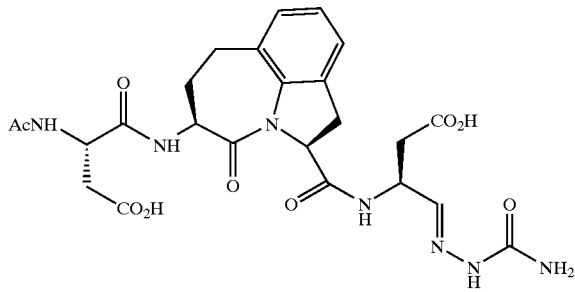

(2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic Acid Semicarbazone To a solution of (2S-cis)-[5-(N-acetyl-(S)-aspartyl-b-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone (0.117 g, 0.178 mmol) in methylene chloride (1 mL) was. added anisole (0.5 mL) followed by trifluoroacetic acid (1 mL). After stirring at room temperature under nitrogen for 2 hours, the reaction mixture was diluted with methylene chloride and evaporated, then chased twice with methylene chloride to give the title compound (0.099 g). TLC (methylene chloride-methanol-acetic acid, 13:6:1) Rf=0.2. Mass spectrum: m/z 560 (M+H).

EXAMPLE 82

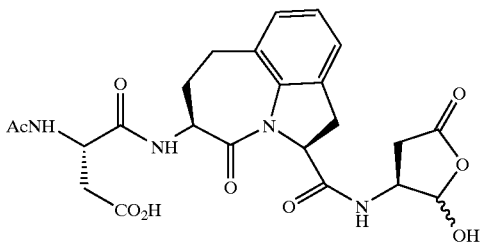

(2S-cis)-[5-(N-Acetyl-(S)-aspartyl)amino-1,2,3,4,5,
6,7-hexahydro-4-oxoazepino[3,2,1-hi]indole-2-
carbonyl)-amino]-4-oxo-butanoic Acid (2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid semicarbazone (0.097 g, 0.177 mmol), was treated with a 3:1:1 solution of methanol-acetic acid-37% formaldehyde (2 mL) and the resulting mixture stirred under nitrogen for 1.5 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.050 g (56%) of the title compound as a white solid after lyophilization; m.p. 160–175° C. (dec). TLC (methylene chloride-methanol-acetic acid, 13:6:1) Rf=0.3. Mass spectrum: m/z 503 (M+H).

EXAMPLE 83

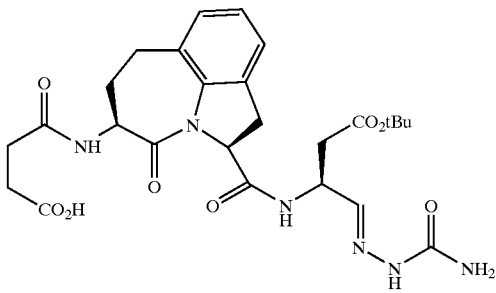

(2S-cis)-[-Succinylamino-1,2,3,4,5,6,7-hexahydro-4-
oxoazelpino[3,2,1-hi]indole-2-carbonyl)-amino]-4-
oxo-butanoic Acid tert-butyl Ester Semicarbazone To a solution of (2S-cis)-[5-amino-1,2,3,4,5,6,7-hexahydro-4-oxoazepino[3,2,1-hi]indole-2-carbonyl)-amino-4-oxo-butanoic acid tert-butyl ester semicarbazone (0.197 g, 0.435 mmol) in methylene chloride (6 mL) stirring at 0° C. under nitrogen was added succinic anhydride (0.057 g, 0.566 mmol), followed by pyridine (0.052 mL, 0.653 mmol). After stirring at room temperature under nitrogen for 3 hours, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM) eluting with 10% methanol-methylene chloride then 80:19:1 methylene chloride-methanol-acetic acid gave 0.216 g (88%) of the title compound as a white solid. TLC (methylene chloride-methanol-acetic acid, 8:1:1) Rf=0.5. Mass spectrum: m/z 557 (M−H).

EXAMPLE 84

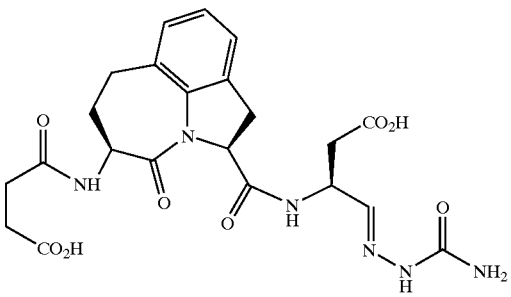

(2S-cis)-[5-Succinylamino-1,2,3,4,5,6,7-hexahydro-
4-oxoazepino[3,2,1-hi]indole-2-carbonyl)-amino]-4-
oxo-butanoic Acid Semicarbazone To a solution of (2S-cis)-[5-succinylamino-1,2,3,4,5,6,7-hexahydro-4-oxoazepino[3,2,1-hi]indole-2-carbonyl)-amino]-4-oxo-butanoic acid tert-butyl ester semicarbazone (0.191 g, 0.342 mmol) in methylene chloride (1 mL) was added adsole (0.5 mL) followed by trifluoroacetic acid (1 mL). After stirring at room temperature under nitrogen for 2 hours, the reaction mixture was diluted with methylene chloride and evaporated, then chased twice with methylene chloride to give the title compound. (0.210 g). TLC (methylene chloride-methanol-acetic acid, 8:1:1) Rf=0.4. Mass spectrum: m/z 503 (M+H).

EXAMPLE 85

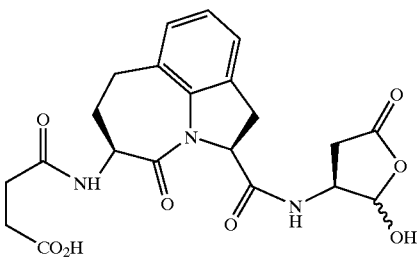

(2S-cis)-[5-Succinylamino-1,2,3,4,5,6,7-hexahydro-
4-oxoazepino[3,2,1-hi]indole-2-carbonyl)-amino]-4-
oxo-butanoic Acid (2S-cis)-[5-Succinylamino-1,2,3,4,5,6,7-hexahydro-4-oxoazepino[3,2,1-hi]indole-2-carbonyl)-amino]-4-oxo-butanoic acid semicarbazone (0.208 g, ca. 0.342 mmol), was treated with a 3:1:1 solution of methanol-acetic acid-37% formaldehyde (3 mL), and the resulting mixture stirred under nitrogen for 1.5 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.064 g (42%) of the title compound as a white solid after lyophilization; m.p. 145–160° C. (dec). TLC (methylene chloride-methanol-acetic acid, 8:1:1) Rf=0.45. Mass spectrum: m/z 446 (M+H).

EXAMPLE 86

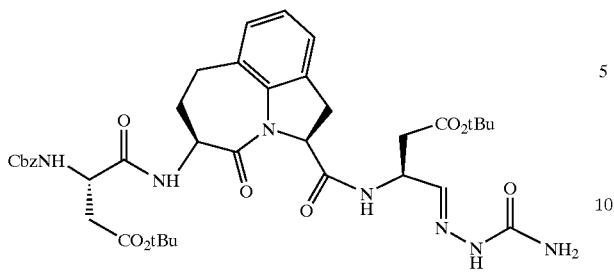

(2S-cis)-[5-(N-Benzyloxycarbonyl-(S)-aspartyl-b-tert-butyl Ester)amino-1,2,3,4,5,6,7-hexahydro-4-oxoazepino[3,2,1-hi]indole-2-carbonyl)-amino]-4-oxo-butanoic Acid tert-Butyl Ester Semicarbazone To a solution of N-benzyloxycarbonyl-(S)-aspartyl-β-tert-butyl ester (0.169 g, 0.521 mmol) in methylene chloride (1.5 mL) stirring at 0° C. under nitrogen was added 1-hydroxybenzotriazole hydrate (0.087 g, 0.569 mmol) and 1-(3-dimethylaminopropyl)-3-ethylcarbodiimide hydrochloride (0.136 g, 0.711 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.217 g, 0.474 mmol) in methylene chloride (2 mL) was added and the reaction was allowed to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM eluting with 2% then 5% methanol-methylene chloride gave 0.244 g (67%) of the title compound as an off-white solid. TLC (methylene chloride-methanol, 9:1) Rf=0.55. $^1$H-NMR (300 MHz, CDCl$_3$) δ 9.13 (s, 1H), 7.85 (d, J=6 Hz, 1H), 7.56 (d, J=5.7 Hz, 1H) 7.23 (m, 5H), 7.08 (m, 1H), 7.00 (m, 2H), 5.13 (m, 3H) 4.77 (m, 1H), 4.62 (m, 1H), 4.43 (m, 1H), 3.60 (d, J=16 Hz, 1H), 3,22 (m, 2H), 2.98 (m, 1H), 2.83 (d, J=15.3 Hz, 1H), 2.65 & 2.36 (AB, dd, J=4.2, 7.7, 16.9 Hz, 2H), 2.42 (m, 1H), 2.10 (m, 1H), 1.35 (s, 9H), 1.24 (s, 9H).

EXAMPLE 87

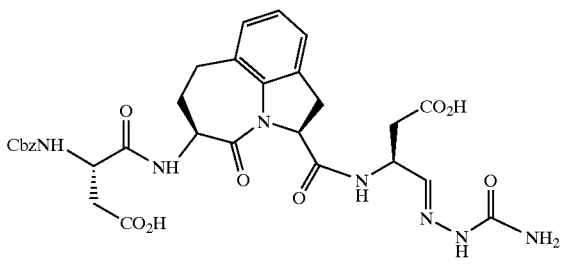

(2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]4-oxo-butanoic Acid Semicarbazone To a solution of (2S-cis)-[5-(N-Benzyloxycarbonyl-(S)-aspartyl-b-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone (0.217 g, 0.289 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride an d evaporated, then chased twice with methylene chloride to give the title compound (0.193 g). TLC (methylene chloride-methanol, 9:1) Rf=0.35. Mass spectrum: m/z 652 (M+H).

EXAMPLE 88

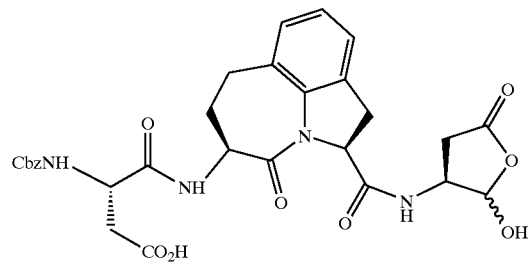

(2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic Acid (2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid semicarbazone (0.191 g, 0.29 mmol), was treated with a 3:1:1 solution of methanol-acetic acid-37% formaldehyde (2 mL) and the resulting mixture stirred under nitrogen for 2 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.111 g. (64%) of the title compound as a white solid after lyophilization; m.p. 140–144° C. (dec.). TLC (methylene chloride-methanol, 9:1) Rf=0.4. Mass spectrum: m/z 593 (M–H).

EXAMPLE 89

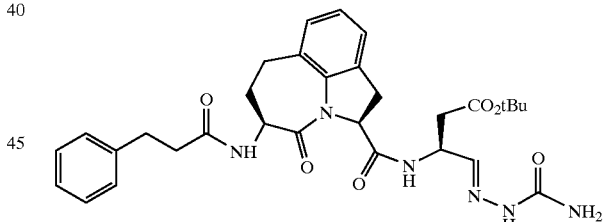

(2S-cis)-[5-Dihydrocinnamylamino-1,2,3,4,5,6,7-hexahydro-4-oxoazepino[3,2,1-hi]indole-2-carbonyl)-amino]-4-oxo-butanoic Acid tert-Butyl Ester Semicarbazone To a solution of dihydrocinnamic acid (0.169 g, 0.521 mmol) in methylene chloride (1.5 mL) stirring at 0° C. under nitrogen was added 1-hydroxybenzotriazole hydrate (0.088 g, 0.576 mmol) and 1-(3-dimethylaminopropyl)-3-ethylcarbodiimide hydrochloride (0.127 g, 0.665 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.203 g, 0.443 mmol) in methylene chloride (2 mL), was added and the reaction was allowed to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM) eluting with 2 then 5% methanol-methylene chloride gave 0.208 g (79%) of the title compound as an off-white solid. TLC (methylene chloride-methanol, 9:1) Rf=7. $^1$H-NMR (300 MHz, CDCl$_3$) δ 8.82 (s, 1H), 7.72 (d, J=8.1 Hz, 1H), 7.19 (m, 5H), 7.06 (m, 1H), 7.01 (m, 2H), 6.76 (d, J=6.3, 1H), 523 (d, J=8.4 Hz, 1H, 4.84 (m, 1H), 4.50 (m, 1H), 3.48 (m, 1H), 3,26 (m, 2H), 3.05 (m, 1H), 2.94 (m, 2H), 2.53 (m, 4H), 2.28 (m, 1H), 2.06 (m, 1H), 1.29 (s, 9H). Mass spectrum: m/z 591 (M+H).

EXAMPLE 90

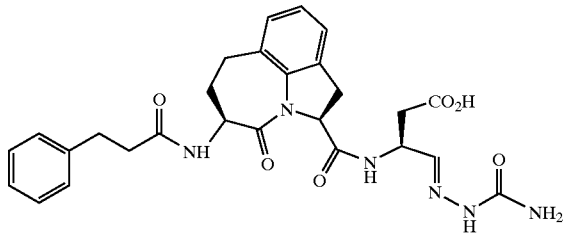

(2S-cis)-[5-Dihydrocinnamylamino-1,2,3,4,5,6,7-hexahydro-4-oxoazepino[3,2,1-hi]indole-2-carbonyl)-amino]-4-oxo-butanoic Acid Semicarbazone To a solution of (2S-cis)-[5-dihydrocinnamylamino-1,2,3,4,5,6,7-hexahydro-4-oxoazepino[3,2,1-hi]indole-2-carbonyl)-amino]-4-oxo-butanoic acid tert-butyl ester semicarbazone (0.189 g, 0.320 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride and evaporated, then chased twice with methylene chloride to give the title compound (0.183 g). TLC(methylene chloride-methanol, 9:1) Rf=0.25. Mass spectrum: m/z 535 (M+H).

EXAMPLE 91

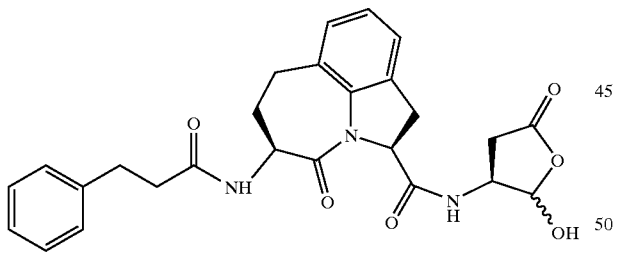

(2S-cis)-[5-Dihydrocinnamylamino-1,2,3,4,5,6,7-hexahydro-4-oxoazepino[3,2,1-hi]indole-2-carbonyl)-amino]-4-oxo-butanoic Acid (2S-cis)-[5-Dihydrocinnamylamino-1,2,3,4,5,6,7-hexahydro-4-oxoazepino[3,2-hi]indole-2-carbonyl)-amino]-4-oxo-butanoic acid semicarbazone (0.181 g, ca. 0.320 mmol), was treated with a 3:1:1 solution of methanol-acetic acid-37% formaldehyde (2 mL) and the resulting mixture stirred under nitrogen for 4 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.075 g (47%) of the title compound as a white solid after lyophilization; m.p. 78–81° C. TLC (methylene chloride-methanol, 9:1) Rf=0.45. $^1$H-NMR (300 MD, DMSO d6): δ 8.58 (m, 1H), 8.30 (d, J=7.5 Hz, 1H), 7.24 (m, 5H), 7.08 (m, 2H), 6.99 (m, 1H), 5.04 (d, J=9.3 Hz, 1H), 4.39 (m, 1H), 4.19 (m, 1H), 3.46 (m, 1H), 3.05 (m, 2H), 2.93 (d, J=16.8 Hz, 2H), 2.83 (m, 2H), 2.00 (d, J=5.1 Hz, 2H). Mass spectrum: m/z 478 (M+H).

EXAMPLE 92

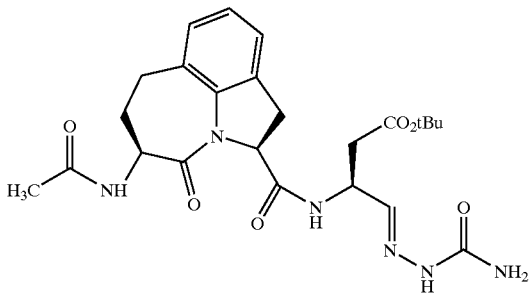

(2S-cis)-[5-Acetylamino-1,2,3,4,5,6,7-hexahydro-4-oxoazepino[3,2,1-hi]indole-2-carbonyl)-amino]-4-oxo-butanoic Acid tert-Butyl Ester Semicarbazone To a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.222 g, 0.490 mmol) in pyridine (3 mL) at room temperature under nitrogen was added acetic anhydride (0.07 mL, 0.735 mmol). After stirring overnight, the reaction mixture was diluted with methylene chloride and evaporated to give a foam. This was taken up in ethyl acetate and washed successively with 5% potassium bisulfate and saturated sodium chloride solutions; dried (sodium sulfate) and evaporated to dryness to give 0.130 g (53%) of the title compound as an off-white solid. TLC (methylene chloride-methanol, 9:1) Rf=0.55. $^1$H-NMR (300 MHz, CDCl$_3$): δ 8.75 (s, 1H), 7.75 (d, J=8.4 Hz, 1H), 7.08 (m, 1H), 7.01 (m, 2H), 6.87 (d, J=6.3 Hz, 1H), 5.25 (d, J=8.1 Hz, 1H), 4.84 (m, 1H), 4.52 (m, 1H), 3.50 (m, 1H), 3,28 (m, 2H), 3.02 (m, 1H), 2.55 & 2.46 (AB, dd, J=4.2, 7.1, 15.7 Hz, 2H), 2.36 (m, 1H), 2.18 (m, 1H), 2.02 (s, 3H), 1.31 (s, 9H).

EXAMPLE 93

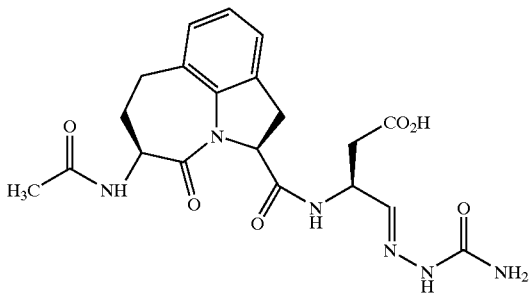

(2S-cis)-[5-Acetylamino-1,2,3,4,5,6,7-hexahydro-4-oxoazepino[3,2,1-hi]indole-2-carbonyl)-amino]-4-oxo-butanoic Acid Semicarbazone To a solution of (2S-cis)-[5-acetylamino-1,2,3,4,5,6,7-hexahydro4-oxoazepino[3,2,1-hi]indole-2-carbonyl)-amino]-4-oxo-butanoic acid tert-butyl ester semicarbazone (0.112 g, 0.224 mmol) in methylene chloride (1 mL) was added anisole (0.5 mL) followed by trifluoroacetic acid (1 mL). After stirring at room temperature under nitrogen for 2.5 hours, the reaction mixture was diluted with methylene chloride and evaporated, then chased twice with methylene chloride to give the title compound (0.117 g). TLC (methylene chloride-methanol, 9:1) Rf=0.15. Mass spectrum: m/z 445 (M+H).

EXAMPLE 94

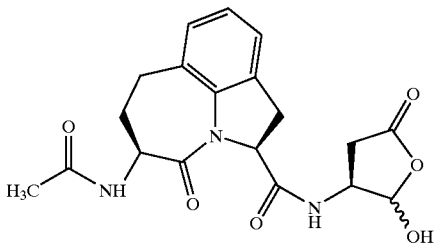

(2S-cis)-[5-Acetylamino-1,2,3,4,5,6,7-hexahydro-4-oxoazepino[3,2,1-hi]indole-2-carbonyl)-amino]-4-oxo-butanoic Acid (2S-cis)-[5-Acetylamino-1,2,3,4,5,6,7-hexahydro-4-oxoazepino[3,2,1-hi]indole-2-carbonyl)-amino]-4-oxo-butanoic acid semicarbazone (0.115 g, ca. 0.224 mmol) was treated with a 3:1:1 solution of methanol-acetic acid-37% formaldehyde (2 mL) and the resulting mixture stirred under nitrogen for 5 hours. The reaction mixture was diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.044 g (51%) of the title compound as a white solid after lyophilization; m.p. 210–215° C. (dec). TLC (methylene chloride-methanol-acetic acid, 44:5:1) Rf=0.45. Mass spectrum: n/z 388 (M+H).

EXAMPLE 95

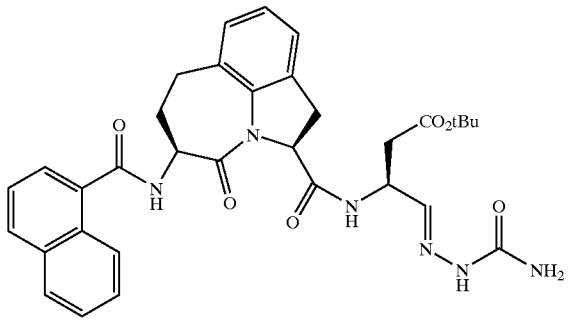

(2S-cis)-[5-(1-Naphthoyl)amino-1,2,3,4,5,6,7-hexahydro-4-oxoazepino[3,2,1-hi]indole-2-carbonyl)-amino]-4-oxo-butanoic Acid tert-Butyl Ester Semicarbazone To a solution of 1-naphthoic acid (0.072 g, 0.417 mmol) in methylene chloride (1.5 mL) stirring at 0° C. under nitrogen was added 1-hydroxybenzotriazole hydrate (0.077 g, 0.501 mmol.) and 1-(3-dimethylaminopropyl)-3-ethylcarbodiimide hydrochloride (0.120 g, 0.626 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.189 g, 0.147 mmol) in methylene chloride (2 mL), was added and the reaction was allowed to come to room temperature within 1 hour. After stirring a total of 5 hours, the reaction mixture was diluted with ethyl acetate and washed successively with 5% potassium bisulfate and saturated sodium chloride solutions, dried (sodium sulfate) and evaporated to dryness. Purification of the crude product by flash chromatography on silica gel (S/P brand silica gel 60 Å, 230–400 mesh ASTM eluting with 5% methanol-methylene chloride gave 0.168 g (66%) of the title compound as an off-white solid; m.p. 103–105° C.; (dec.). TLC (methylene chloride-methanol, 9:1) Rf=0.6. Mass spectrum: m/z 613 (M+H). $^1$H-NMR (300 MHz, CDCl$_3$) δ 9.09 (bs, 1H), 8.38 (d, J=8.4 Hz, 1H), 7.82–7.93 (m, 3H), 7.70 (d, J=6.3 Hz, 1H), 7.45–7.58 (m, 3H), 7.37 (d, J=6.6 Hz, 1H), 7.06–7.15 (m, 4H), 5.30 (d, J=8.4 Hz, 1H), 4.80–4.85 (m, 2H), 3.57 (d, J=3.6 Hz, 1H), 3.30–3.45 (m, 2H), 3.16 (m, 1H), 2.59–2.65 (m, 2H), 2.27–2.49 (m, 2H), 1.29 (s, 9H).

EXAMPLE 96

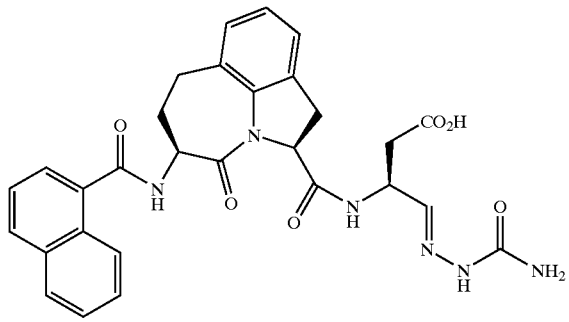

(2S-cis)-[5-(1-Natphthoyl)amino-1,2,3,4,5,6,7-hexahydro-4oxoazepino[3,2,1-hi]indole-2-carbonyl)-amino]4-oxo-butanoic Acid Semicarbazone To a solution of (2S-cis)-[5-(1-naphthoyl)amino-1,2,3,4,5,6,7-hexahydro-4-oxoazepino[3,2,1-hi]indole-2-carbonyl)-amino]-4-oxo-butanoic acid tert-butyl ester semicarbazone (0.106 g, 0.173 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride and evaporated, then chased twice with methylene chloride to give the title compound (0.110 g). TLC (methylene chloride-methanol, 9:1) Rf=0.3.

EXAMPLE 97

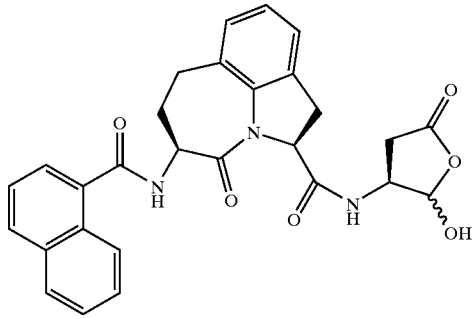

(2S-cis)-[5-(1-Naphthoyl)amino-1,2,3,4,5,6,7-hexahydro-4-oxoazepino[3,2,1-hi]indole-2-carbonyl)-amino]-4-oxo-butanoic Acid (2S-cis)-[5-(1-Naphthoyl)amino-1,2,3,4,5,6,7-hexahydro-4-oxoazepino[3,2,1 -hi]indole-2-carbonyl)- amino]-4-oxo-butanoic acid semicarbazone (0.110 g, ca. 0.173 mmol) was treated with a 3:1:1 solution of methanol-acetic acid-37% formaldehyde (3 mL) and the resulting mixture stirred under nitrogen for 5 hours. The reaction mixture was then diluted with water, methanol removed by evaporation, then the remaining mixture lyophilized. Purification of the crude product by flash chromatography on silica gel (S/P brand silica gel 60 Å, 230–400 mesh ASTM) eluting with a 5%–20% methanol-methylene chloride gradient gave 0.076 g (86%) of the title compound as a white solid; m.p. 202–203° C. (dec). TLC(methylene chloride-methanol-acetic acid, 20:1:1) Rf==03. Mass spectrum: m/z 498 (M−H). $^1$H-NMR (300 MHz, CDCl$_3$) δ 9.38 (bs, 1H), 8.94 (m, 1H), 8.56 (m, 1H), 8.36 (m, 1H), 7.94–8.02 (m, 2H), 7.68 (d, J=6.9 Hz, 1H), 7.51–7.59 (m, 3H), 7.07–7.13 (m, 2H), 6.97 (m, 1H), 5.20 (d, J=10.5, 1Hz), 4.67 (m, 1H), 4.15 (m, 1H), 3.49 (m, 1H), 2.95–3.23 (m, 2H), 2.53 (m, 1H), 2.22–2.34 (m, 2H).

EXAMPLE 98

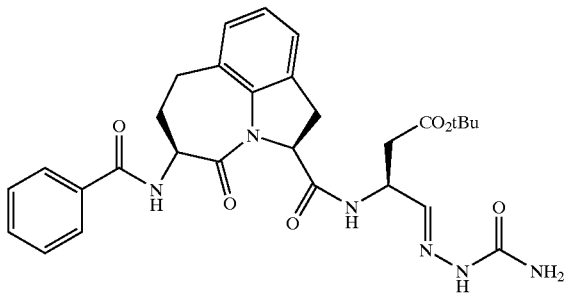

(2S-cis)-[5-Benzoylamino-1,2,3,4,5,6,7-hexahydro-4-oxoazepino[3,2,1-hi]indole-2-carbonyl)-amino]-4-oxo-butanoic Acid tert-Butyl Ester Semicarbazone To a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.121 g, 0.264 mmol) in methylene chloride (2.5 mL) stirring at 0° C. under nitrogen was added triethylamine (0.055 mL, 0.396 mmol), followed by benzoyl chloride (0.037 mL, 0.317 mmol). After stirring at room temperature under nitrogen for 1 hour, the reaction mixture was diluted with ethyl acetate and washed successively with 5% potassium bisulfate, saturated sodium bicarbonate and saturated sodium chloride solutions; dried (sodium sulfate) and evaporated to dryness. Purification of the crude product by flash chromatography on silica gel (S/P brand silica gel 60 Å, 230–400 mesh ASTM) eluting with 10% hexane-ethyl acetate, 100% ethyl acetate, then 10% methanol-ethyl acetate gave 0.073 g (49%) of the title compound as a off-white solid. TLC (methylene chloride-methanol, 9:1) Rf=0.7. Mass spectrum: m/z 563 (M+H). $^1$H-NMR (300 MHz, CDCl$_3$): δ 8.61 (bs, 1H), 7.83–7.86 (m, 2H), 7.47–7.53 (m, 3H), 7.06–7.12 (m, 3H), 5.30 (dd, J=2.2, 7.8 Hz, 1H), 4.89 (m, 1H), 4.72 (m, 1H), 3.60 (d, J=16.5 Hz, 1H), 3.36 (m, 1H), 3.19 (m, 1H), 2.69 (dd, J=4.4, 11.7 Hz, 1H), 2.52 (m, 1H), 2.29 (m, 1H), 1.34 (s, 9H).

EXAMPLE 99

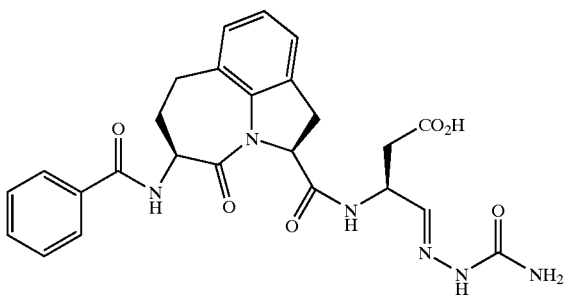

(2S-cis)-[5-Benzoylamino-1,2,3,4,5,6,7-hexahydro-4-oxoazepino[3,2,1-hi]indole-2-carbonyl)-amino]-4-oxo-butanoic Acid Semicarbazone To a solution of (2S-cis)-[5-benzoylamino-1,2,3,4,5,6,7-hexahydro-4-oxoazepino[3,2,1-hi]indole-2-carbonyl)-amino]-4oxo-butanoic acid tert-butyl ester semicarbazone (0.064 g, 0.114 mmol) in methylene chloride (1 mL) was added anisole (0.5 mL) followed by trifluoroacetic acid (1 mL). After stirring at room temperature under nitrogen for 2.5 hours, the reaction mixture was diluted with ethyl acetate and evaporated to give the title compound (0.070 g). TLC (methylene chloride-methanol, 4:1) Rf=0.4. Mass spectrum: m/z 507 (M+H).

EXAMPLE 100

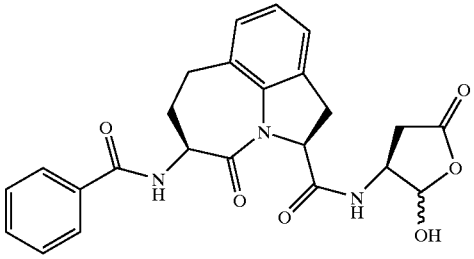

(2S-cis)-[5-Benzoylamino-1,2,3,4,5,6,7-hexahydro-4-oxoazepino[3,2,1-hi]indole-2-carbonyl)-amino]-4-oxo-butanoic Acid (2S-cis)-[5-Benzoylamino-1,2,3,4,5,6,7-hexahydro-4-oxoazepino[3,2,1-hi]indole-2-carbonyl)-amino]4-oxo-butanoic acid semicarbazone (0.070 g, ca. 0.114 mmol) was treated with a 3:1:1 solution of methanol-acetic acid-37% formaldehyde (3 mL), and the resulting mixture stirred under nitrogen for 3.5 hours. The reaction mixture was then diluted with water, methanol removed by evaporation, then the remaining mixture lyophilized. Purification of the crude product by flash chromatography on silica gel (S/P brand silica gel 60 Å, 230–400 mesh ASTM) eluting with 10 and 20% methanol-methylene chloride gave 0.042 g (82%) of the title compound as a white solid; m.p. 204–205° C. (dec). TLC (methylene chloride-methanol, 4:1) Rf=0.4. Mass spectrum: m/z 448 (M−H). $^1$H-NMR (300 MHz, DMSO-d$_6$) δ 8.84 (m, 1H), 8.53 (m, 1H), 7.91–7.95 (m, 2H), 7.46–7.58 (m, 3H), 7.11 (m, 2H), 6.99 (t, J=7.3 Hz, 1H), 5.14 (d, 10.2 Hz, 1H), 4.62 (m, 1H), 4.23 (m, 1H), 3.48 (m, 1H), 3.12–3.18 (m, 2H), 2.99 (m, 1H), 2.58 (m, 1H), 2.12–2.46 (m, 3H).

EXAMPLE 101

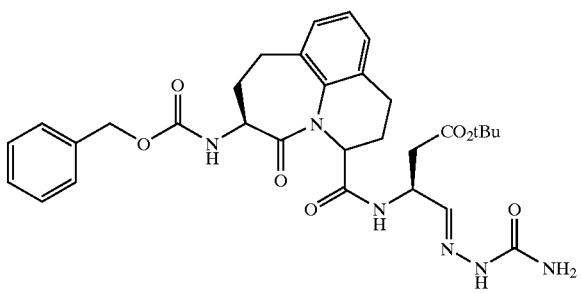

(3R,S-cis)-6-Benzyloxycarbonylamino-5-oxo-2,3,4,
5,6,7,8-hexahydro-1H-azerpino[3,2,1-hi]quinoline-
3-carbonyl)-amino]-4-oxo-butanoic Acid tert-Butyl
Ester Semicarbazone 1. Preparation of (3R,S-cis)-6-Benzyloxycarbonylamino-5-oxo-2,3,4,5,6,7,8-hexahydro-1H-azepino[3,2,1-hi] quinoline-3-carboxylic Acid, Methyl Ester To a solution of (3R,S-cis)-6-Amino-5-oxo-2,3,4,5,6,7,8-hexahydro-1H-azepino[3,2,1-hi]quinoline-3-carboxylic acid, methyl ester (0.570 g, 2.1 mmol, prepared as described in Tetrahedron Letters 36, pp. 1593–1596 (1995) and U.S. Pat. No. 5,504,080 (Apr. 2, 1996)) in methylene chloride (6 mL) stirring at 0° C. was added benzyl chloroformate (0.6 mL, 4.2 mmol) and triethylamine (1.2 mL, 8.4 mmol) and the resulting mixture was stirred under nitrogen for 30 minutes. The reaction was quenched with water then partitioned between ethyl acetate and 5% aqueous potassium bisulfate solution. The aqueous layer was back extracted two times with ethyl acetate, then the combined organic layers were washed with saturated sodium chloride solution, dried (sodium sulfate) and evaporated to dryness. Purification of the crude product by flash chromatography on silica gel (S/P brand silica gel 60 Å, 230–400 mesh ASTM) eluting with ethyl acetate-hexane (2:1) gave 0.643 g (76%) of the title compound as a white foam. TLC (methylene chloride-methanol, 95:5) Rf=0.8. $^1$H-NMR (300 MHz, CDCl$_3$) δ 7.36–7.25 (m, 5H), 7.13–7.02 (m, 3H), 5.67 (d, J=7.8 Hz, 1H), 5.02 (t, J=9.15, 18.3 Hz, 2H), 4.34 (m, 1H), 3.70 (s, 3H), 3.16 (m, 1H), 2.69–2.56 (m, 5H), 2.06 (m, 1H). Mass spectrum: m/z 408 (M+H).

2. Preparation of (3R,S-cis)-6-Benzyloxycarbonylamino-5-oxo-2,3,4,5,6,7,8-hexahydro-1H-azepino[3,2,1-hi] quinoline-3-carboxylic Acid To a solution of (3R,S-cis)-6-Benzyloxycarbonylamino-5-oxo-2,3,4,5,6,7,8-hexahydro-1H-azepino[3,2,1-hi] quinoline-3-carboxylic acid, methyl ester (0.622g, 1.53 mmol) in 1,4-dioxane (10.5 mL) and water (3.5 mL) was added 1M aqueous lithium hydroxide (2.3 mL, 2.3 mmol) and the resulting mixture was stirred at room temperature under nitrogen for 1 hour. The reaction mixture was acidified to ca. pH 2 with a 5% aqueous potassium bisulfate solution, then partitioned between ethyl acetate and saturated sodium chloride solution. The aqueous layer was back extracted two times with ethyl acetate, and the combined organic layers were dried (sodium sulfate) and evaporated to yield 0.670 g of the title compound. TLC (methylene chloride-methanol-acetic acid, 32:1:1) Rf=0.35. $^1$H-NMR (300 MHz, CDCl$_3$): δ 7.38–7.28 (m, 5H), 7.13–7.04 (m, 3H), 5.72 (d, J=8.1 Hz, 1H), 5.03 (s, 2H), 4.35 (m, 1H), 3.77–3.67 (m, 5H), 3.10 (m, 1H), 2.72–2.52 (m, 5H), 2.07 (m, 1H), 1.70 (m, 1H).

3. (3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic Acid tert-Butyl Ester Semicarbazone To a solution of (3R,S-cis)-6-benzyloxycarbonylamino-5-oxo-2,3,4,5,6,7,8-hexahydro-1H-azepino[3,2,1-hi] quinoline-3-carboxylic acid (0.604 g, 1.5 mmol) in methylene chloride (12 mL) stiring at 0° C. under nitrogen was added 1-hydroxybenzotriazole hydrate (0.282 g, 1.8 mmol) and 1-(3-dimethylaminopropyl)-3-ethylcarbodiimide hydrochloride (0.442 g, 3 mmol). After 15 minutes, L-aspartic acid semicarbazone β-tert-butyl ester, p-toluenesulfonate salt (0.60 g, 1.5 mmol) and N-methylmorpholine (0.25 mL, 3 mmol) were added and the mixture allowed to come to room temperature within 1 hour. After stirring an additional hour, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM) eluting with 10% methanol-methylene chloride gave 0.523 g (56%) of the title compound as a white foam. TLC (methylene chloride-methanol, 9:1) Rf=0.65. $^1$H-NMR (300 MHz, CDCl$_3$): δ 9.89 (m, 1H), 7.72 (m, 1H), 7.92 (d, J=9 Hz, 1H), 7.65 (d, J=8.1 Hz, 1H), 7.32–7.28 (m, 5H), 7.12 (s, 1H), 7.07 (d, J=5.7 Hz, 2H), 6.03 (d, J=7.5 Hz, 1H), 5.84 (d, J=8.1 Hz, 1H), 5.03 (s, 2H), 5.01 (m, 1H) 4.80 (m, 1H), 4.31 (m, 1H), 2.98 (m, 1H), 2.75–2.41 (m, 7H), 2.12 (m, 1H), 1.77 (m, 1H), 1.39 (s, 9H).

EXAMPLE 102

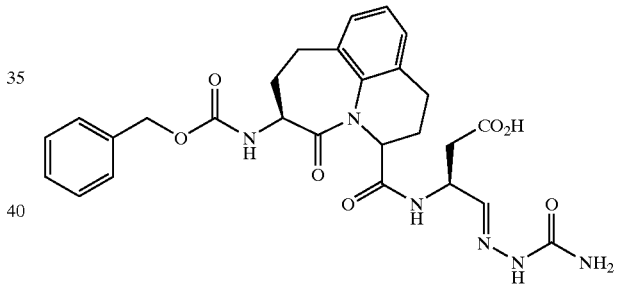

(3R,S-cis)-6-Benzyloxycarbonylamino-5-oxo-2,3,4,
5,6,7,8-hexahydro-1H-azepino[3,2,1-hi]quinoline-3-
carbonyl)-amino]-4-oxo-butanoic Acid
Semicarbazone To a solution of (3R,S-cis)-6-Benzyloxycarbonylamino-5-oxo-2,3,4,5,6,7,8-hexahydro-1H-azepino[3,2,1-hi] quinoline-3-carbonyl)-amino]-4-oxo-butanoic acid tert-butyl ester semicarbazone (0.200 g, 0.33 mmol) in methylene chloride (1 mL) was added anisole (0.5 mL, 4.62 mmol) followed by trifluoroacetic acid (1 mL). After stirring at room temperature under nitrogen for 1.5 hours the reaction mixture was diluted with methylene chloride and evaporated, then azeotroped twice with methylene chloride to give the title compound (0.248 g). TLC (methylene chloride-methanol-acetic acid, 8:1:1) Rf=0.2. Mass spectrum: m/z 549 [M−H]$^-$.

EXAMPLE 103

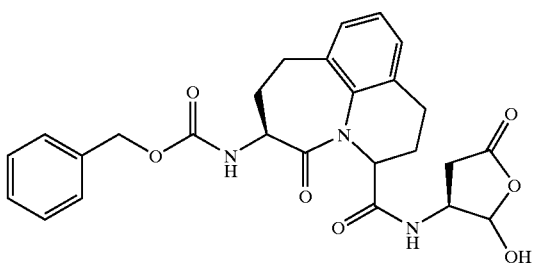

(3R,S-cis)-6-Benzyloxycarbonylamino-5-oxo-2,3,4,
5,6,7,8-hexahydro-1H-azepino[3,2,1-hi]quinoline-3-
carbonyl)-amino]-4-oxo-butanoic Acid (3R,S-cis)-6-Benzyloxycarbonylamino-5-oxo-2,3,4,5,6,
7,8-hexahydro-1H-azepino[3,2,1-hi]quinoline-3-carbonyl)-
amino]-4-oxo-butanoic acid semicarbazone (0.245 g, ca
0.33 mmol), was treated with a 3:1:1 solution of methanol-
acetic acid-37% formaldehyde (3 mL) and the resulting
mixture stirred under nitrogen for 1.5 hours. The reaction
mixture was diluted with water, methanol removed by
evaporation, then the remaining mixture lyophilized. Purification of the crude product by flash chromatography on
reverse phase gel (MCI gel, CHP-20P, 75–150 micron)
eluting with a 10%–80% methanol-water gradient gave
0.090 g (60%) of the title compound as a white solid after
lyophilization; m.p. 120–123° C. (dec). TLC (methylene
chloride-methanol-acetic acid, 32:1:1) Rf=0.45. $^1$H-NMR
(300 MHz, DMSO d6): δ 8.67 (m, 1H), 7.79 (m, 1H), 7.57
(m, 1H), 7.37–7.27 (m, 5H), 7.17–7.08 (m, 3H), 5.44 (m,
1H), 4.95 (s, 2H), 4.70 (m, 1H), 4.07 (m, 1H), 3.92 (m, 1H),
3.16 (m, 1H), 2.98 (m, 1H), 2.75–2.41 (m, 7H), 2.25 (m,
1H), 2.11 (m, 1H), 1.29 (m, 1H). Mass spectrum: m/z 492
[M−H]$^-$.

EXAMPLE 104

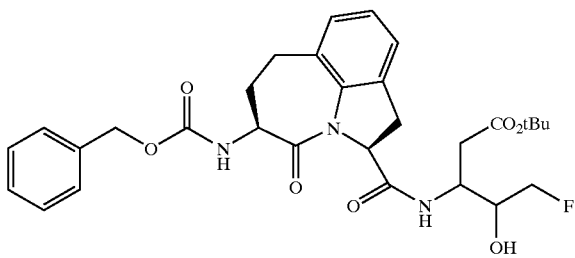

3{(2S-cis)-[5-Benzyloxycarbonylamino-1,2,3,4,5,6,
7-hexahydro-4-oxoazepino[3,2,1-hi]indole-2-
carbonyl-amino]}-5-fluoro-4-hydroxy-pentanoic
Acid tert-Butyl Ester To a solution of (2S-cis)-5-benzyloxycarbonylamino-1,2,
3,4,5,6,7-hexahydro-4-oxoazepino[3,2,1-hi]indole-2-
carboxylic acid (0.373 g, 0.98 mmol) in methylene chloride
(3 mL) stirring at 0° C. under nitrogen was added
1-hydroxybenzotriazole hydrate (0.151 g, 0.98 mmol) and
1-(3-dimethylaminopropyl)-3-ethylcarbodiimide hydrochloride (0.283 g, 1.47 mmol). After 15 minutes, 3-amino-
4-hydroxy-5-fluoropentanoic acid, tert-butyl ester (0.204 g,
0.98 mmol, prepared as described in Tetrahedron Letters 35,
pp. 9693–9696 (1994)) was added and the mixture allowed
to come to room temperature within 1 hour. After stirring
overnight, the reaction mixture was diluted with ethyl
acetate and washed successively with 5% potassium bisulfate and saturated sodium chloride solutions; dried (sodium
sulfate) and evaporated to dryness. Purification of the crude
product by flash chromatography on silica gel (S/P brand
silica gel 60 Å, 230–400 mesh ASTM eluting with 2%
methanol-methylene chloride gave 0.383 g (68%) of the title
compound as a white foam. TLC (methylene chloride-
methanol, 9:1) Rf=0.6. $^1$H-NMR (300 MHz, CDCl$_3$): δ
7.45–7.31(m, 5H), 7.08–7.01 (m, 3H), 6.10 (m, 1H), 5.26
(m, 1H), 5.12 (s, 2H), 4.52 (m, 1H), 4.38–4.30 (m, 2H),
4.21–4.19 (m, 2H), 4.03–3.95 (m, 2H), 3.43–3,20 (m, 4H),
3.13 (m, 2H), 2.62–2.50 (m, 2H), 2.42 (m, 1H), 1.42 (s, 4H),
1.32 (s, 5H). Mass spectrum: m/z 570 (M+H).

EXAMPLE 105

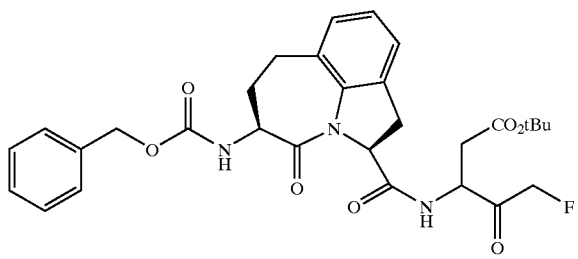

3{(2S-cis)-[5-Benzyloxycarbonylamino-1,2,3,4,5,6,
7-hexahydro-4-oxoazepino[3,2,1-hi]indole-2-
carbonyl)-amino]}-5-fluoro-4-oxo-pentanoic Acid
tert-Butyl Ester To a solution of 3{(2S-cis)-[5-benzyloxycarbonylamino-
1,2,3,4,5,6,7-hexahydro4-oxoazepino[3,2,1-hi]indole-2-
carbonyl)-amino]}-5-fluoro-4-hydroxy-pentanoic acid tert-
butyl ester (0.114 g, 0.20 mmol) in methyl sulfoxide (1.3
mL) was added Dess-Martin periodinane (0.228 g). After
stiring at room temperature under nitrogen for 2 hours an
additional portion of Dess-Martin periodinane (0.135 g) was
added followed 2.5 hours later by a third portion (0.10 g).
The reaction mixture was diluted with ethyl acetate and
washed twice with water and saturated sodium chloride
solution; dried (sodium sulfate) and evaporated to dryness.
Purification of the crude product by flash chromatography
on silica gel (S/P brand silica gel 60 Å, 230–400 mesh
ASTM eluting 1/1 ethyl acetate-hexanes gave 0.076 g (67%)
of the title compound as a white foam. TLC (ethyl acetate-
hexanes, 1:1) Rf=0.6. $^1$H-NMR (300 MHz, CDCl$_3$): δ 7.58
(d, J=8.4 Hz, 1H), 7.34–7.30 (m, 5H), 7.07–6.99 (m, 3H),
6.06 (m, 1H), 5.23 (d, J=12.3 Hz, 1H), 5.12 (s, 2H), 4.53 (d,
J=13,2 Hz, 1H), 4.77 (d, J=9.9 Hz, 2H), 4.32 (m, 1H), 3.44
(dd, J=5, 8.4 Hz, 1H), 3.32–3.21 (m, 2H), 3.06 (m, 1H), 2.9
(m, 1H), 2.62 (m, 1H), 2.41 (m, 1H), 2.17 (m, 1H), 1.39 (s,
4H), 1.29 (s, 5H).

EXAMPLE 106

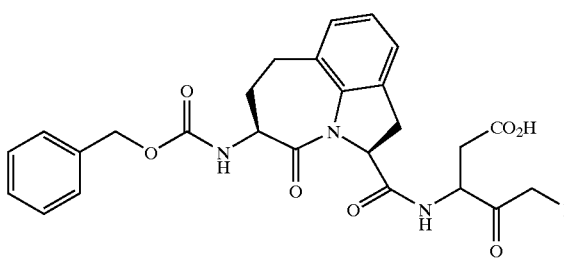

3{(2S-cis)-[5-Benzyloxycarbonylamnino-1,2,3,4,5,6,
7-hexahydro-4-oxoazepino[3,2,1-hi]indole-2-
carbonyl)-amino]}-5-fluoro-4-oxo-pentanoic Acid To a solution of 3{(2S-cis)-[5-benzyloxycarbonylamino-1,2,3,4,5,6,7-hexahydro-4oxoazepino[3,2,1-hi]indole-2-carbonyl)-amino]}-5-fluoro4-oxo-pentanoic acid tert-butyl ester (0.063 g, 0.111 mmol) in methylene chloride (1.0 mL) Was added anisole (0.5 mL), followed by trifluoroacetic acid (1.0 mL). After siring at room temperature under nitrogen for 2 hours the reaction mixture was diluted with methylene chloride and evaporated, then chased twice with methylene chloride. The crude residue was triturated with ethyl ether to give 0.030 g of the titled product as a white solid; m.p. 106–107° C. (dec). TLC (methylene chloride-methanol-acetic acid, 32:1:1) Rf=0.3. $^1$H-NMR (300 MHz, CDCl$_3$): δ 7.61 (m, 1H), 7.32 (s, 5H), 7.1(d, J=4 Hz, 1H), 7.03 (d, J=4 Hz, 2H), 6.17 (m, 1H), 5.22 (m, 1H), 5.10 (s, 2H), 4.75–4.70 (m, 2H), 4.32 (m, 1H), 3.5 (m, 1H), 3.31–3.15 (m, 2H), 3.03 (m, 1H), 2.93 (m, 1H), 2.69 (m, 1H), 2.36 (m, 1H), 2.12 (m, 1H). Mass spectrum: m/z 512 (M+H).

EXAMPLE 107

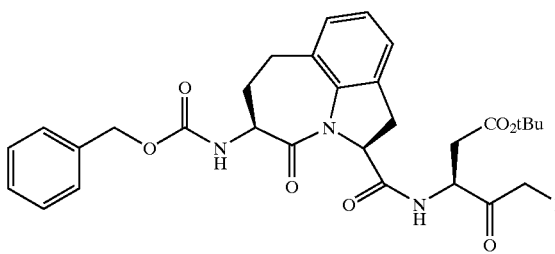

3-[(2S-cis)-[5-Benzyloxycarbonylamino-1,2,3,4,5,6,
7-hexahydro-4-oxoazepino[3,2,1-hi]indole-2-
carbonyl]amino]-5-bromo-4-oxo-pentanoic Acid,
tert-Butyl Ester To a solution of (2S-cis)-5-benzyloxycarbonylamino-1,2,3,4,5,6,7-hexahydro4-oxoazepino[3,2,1-hi]indole-2-carboxylic acid (0.302 g, 0.797 mmol) in methylene chloride (5.5 mL) stirring at 0° C. under nitrogen was added 1-hydroxybenzotriazole hydrate (0.146 g, 0.96 mmol) and 1-(3-dimethylaminopropyl)-3-ethylcarbodiimide hydrochloride (0.230 g, 1.2 mmol). After 15 minutes, aspartic acid, α-methyl, β-tert-butyl diester hydrochloride (0.191 g, 0.797 mmol) was added followed by N-methylmorpholine (0.13 mL, 1.2 mmol) and the mixture allowed to come to room temperature within 1 hour. After siring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230–400 mesh ASTM eluting with ethyl acetate-hexane (1:1) gave 0.350 g (78%) of N-[(2S-cis)-[5-benzyloxycarbonylamino-1,2,3,4,5,6,7-hexahydro-4-oxoazepino[3,2,1-hi]indole-2-carbonyl]]aspartic acid, α-methyl, β-tert-butyl diester as a white solid. TLC (methylene chloride-methanol, 9:1) R$_f$=0.8. m.p. 147–148° C. (dec.). $^1$H-NMR (300 MHz, CDCl$_3$): δ 7.48 (d, J=7.5 Hz, 1H), 7.34–7.29 (m, 5H), 7.07 (m, 1H), 7.03–6.96 (m, 2H), 6.15 (d, J=5.7 Hz, 1H), 5.28 (d, J=7.8 Hz 1H), 5.11 (s, 2H), 4.72 (m, 1H), 4.32 (m, 1H), 3.74 (s, 3H), 3.49 (d, J=16.5 Hz, 1H), 3.31–3.20 (m, 2H), 3.05 (m, 1H), 2.72 (ABX, dd, J=4.65, 15, 64.5 Hz, 2H), 2.43 (m, 1H), 2.15 (m, 1H), 1.30 (s, 9H).

To a solution of the above product (0.330 g, 0.585 mmol) in 1,4-dioxane (4.5 mL) and water (1.5 mL) was added 1M aqueous lithium hydroxide (0.7 mL, 0.702 mmol) and the resulting mixture was stirred at room temperature under nitrogen for 30 minutes. The reaction mixture was acidified to pH 3 with a 0.1N HCl solution, then partitioned between ethyl acetate and saturated sodium chloride solution. The aqueous layer was back extracted two times with ethyl acetate, and the combined organic layers were dried (sodium sulfate) and evaporated to yield 0.275 g (85%) of N-[(2S-cis)-[5-benzyloxycarbonylamino-1,2,3,4,5,6,7-hexahydro-4-oxoazepino[3,2,1-hi]indole-2-carbonyl]]aspartic acid, β-tert-butyl ester as a white foam. TLC(methylene chloride-methanol, 9:1): R$_f$=0.25. $^1$H-NMR (300 MHz, CDCl$_3$): δ 7.57 (d, J=7.8 Hz, 1H), d7.35–7.29 (m, 5H), 7.08 (m, 1H), 7.03–6.98 (m, 2H), 6.24 (d, J=6 Hz, 1H), 5.28 (d, J=5.1 Hz 1H), 5.11 (s, 2H), 4.73 (m, 1H), 4.35 (m, 1H), 3.48 (d, J=16.8 Hz, 1H), 3.36–3.20 (m, 2H), 3.07 (m, 1H), 2.76 (ABX, dd, J=4.8, 18, 66 Hz, 2H), 2.40 (m, 1H), 2.19 (m, 1H), 1.33 (s, 9H).

To a solution of the above product (0.262 g, 0.475 mmol) in tetrahydrofuran (3.0 mL) stirring at −10° C. under nitrogen was added N-methylmorpholine (0.114 mL, 1.05 mmol) followed by dropwise addition of isobutyl chloroformate (0.107 mL, 0.81 mmol). After 40 minutes the reaction mixture was filtered, the salts washed with dry THF, and the filtrate cooled to 0° C. This was treated with a freshly prepared ethereal solution of diazomethane (excess). After stirring the mixture at 0° C. for 30 minutes, a mixture of hydrobromic acid (48% wt. aq. solution)/acetic acid (1.3 mL, 1/1) was added dropwise. After stirring for another 10 minutes, the reaction mixture was diluted with ethyl acetate, then washed successively with saturated sodium bicarbonate and saturated sodium chloride solutions; dried (sodium sulfate) and evaporated to dryness. Purification of the crude product by flash chromatography on silica gel (S/P brand silica gel 60 Å, 230–400 mesh ASTM) eluting with ethyl acetate-hexane (1:1) gave 0.200 g (67%) of the title compound as a white foam. TLC(ethyl acetate-hexane, 1:1 ): R$_f$=0.7. $^1$H-NMR (300 MHz, CDCl): δ 7.71 (d, J=9 Hz, 1H), d7.35–7.30 (m, 5H), 7.09 (m, 1H), 7.04–7.02 (m, 2H), 6.1 (d, J=5.4 Hz, 1H), 5.28 (d, J=7.2 Hz 1H), 5.12 (s, 2H), 4.89 (dd, J=4.5, 15 Hz 1H), 4.35 (m, 1H), 4.16 (s, 2H), 3.50–3, 21(m, 3H), 3.06 (m, 1H), 2.76 (ABX, dd, J=4.65, 18, 103 Hz, 2H), 2.37 (m, 1H), 2.15 (m, 1H), 1.27 (s, 9H). Mass spectrum: m/z 626/628 (M–H).

EXAMPLE 108

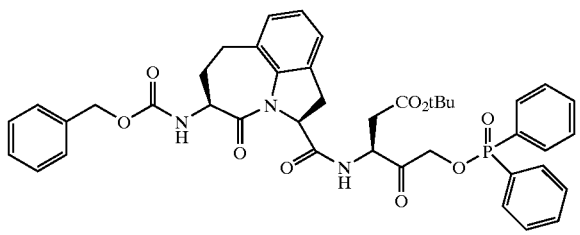

3-[(2S-cis)-[5-Benzyloxycarbonylamino-1,2,3,4,5,6,
7-hexahydro-4-oxoazepino[3,2,1-hi]indole-2-
carbonyl]amino]-5-(diphenylphosphinyl)oxy-4-oxo-
pentanoic Acid, tert-Butyl Ester To a solution of 3-[(2S-cis)-[5-benzyloxycarbonylamino,-1,2,3,4,5,6,7-hexahydro-4-oxoazepino[3,2,1-hi]indole-2-carbonyl]amino]-5-bromo-4oxo-pentanoic acid, tert-butyl ester (0.069 g, 0.110 mmol) in N,N-dimethylformamide (1.0 mL) was added potassium fluoride (0.029 g, 0.495 mmol), followed diphenylphosphinic acid (0.029 g, 0.139 mmol). After stirring at room temperature under nitrogen for 48 hours, the reaction mixture was diluted with ethyl acetate, then washed successively with a dilute sodium bicarbonate solution then water; dried (sodium sulfate) and evaporated to dryness. Purification of the crude product by flash chromatography on silica gel (S/P brand silica gel 60 Å, 230–400 mesh ASTM) eluting with ethyl acetate-hexane (1:1) gave 0.048 g (59%) of the title compound as a clear oil. TLC(ethyl acetate-hexane, 2:1 ): $R_f$=0.3. $^1$H-NMR (300 MHz, CDCl$_3$): δ 7.89–7.80 (m, 4H), 7.52–7.30 (m, 1H), 7.06 (m, 1H), 7.01–6.96 (m, 2H), 6.45 (m, 1H), 5.21 (m, 1H), 5.13 (s, 2H), 4.96 (dd, J=8.3, 18 Hz, 1H), 4.78–4.70 (m, 2H), 4.35 (m, 1H), 3.35–3.23 (m, 3H), 3.05 (m, 1H), 2.76 (ABX, dd, J=4.65, 18, 103 Hz, 2H), 2.43 (m, 1H), 2.18 (m, 1H), 1.33 (s, 9H).

EXAMPLE 109

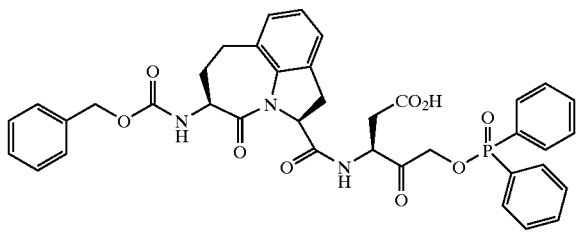

3-[(2S-cis)-[5-Benzyloxycarbonylamino-1,2,3,4,5,6,
7-hexahydro-4-oxoazepino[3,2,1-hi]indole-2-
carbonyl]amino]-5-(diphenylphosphinyl)oxy-4-oxo-
pentanoic Acid To a solution of 3-[(2S-cis)-[5-benzyloxycarbonylamino-1,2,3,4,5,6,7-hexahydro-4-oxoazepino[3,2,1-hi]indole-2-carbonyl]amino]-5-(diphenylphosphinyl)oxy-4-oxo-pentanoic acid, tert-butyl ester (0.040 g, 0.054 mmol) in methylene chloride (1.0 mL) was added anisole (0.5 mL), followed by trifluoroacetic acid (1.0 mL). After stirring at room temperature under nitrogen for 30 minutes the reaction mixture was diluted with methylene chloride and evaporated, then azeotroped twice with methylene chloride. The crude residue was triturated with ethyl ether to give 0.030 g of the titled product as a white solid; m.p. 109–111° C.(dec). TLC (methylene chloride-methanol, 9:1): $R_f$=0.4.

$^1$H-NMR(300 MHz, CDCl$_3$): δ 7.87–7.66 (m, 4H), 7.60–7.28 (m, 1H), 7.05–6.95 (m, 3H), 6.84 (m, 1H), 5.12 (s, 2H), 5.05 (m, 1H), 4.58 (m, 1H), 4.42–4.15 (m, 4H), 3.35–3.10 (m, 4H), 3.0 (m, 1H), 2.76 (m, 1H), 2.56 (m, 1H), 2.37 (m, 1H), 2.13 (m, 1H), 1.93 (bs, 1H). Mass spectrum: m/z 710 (M+H).

EXAMPLE 110

Materials and Methods for Evaluating Effects of ICE/CED-3 Inhibitors on Granulocyte Neutrophils Neutrophil Isolation:

Whole blood anticoagulated with Acid Citrate Dextrose (ACD) with a ratio of 1:5 ACD to blood was collected (~100 ml).

Using polypropylene plastic ware, neutrophils are isolated as follows:

30 ml of the whole blood is added to 50 ml polypropylene centrifuge tubes containing 15 ml of 6% Dextran (in Saline). The blood is allowed to sediment for approximately 1 hour at room temperature.

The turbid straw colored layer harvested from the top of the cylinders into 50 ml conical polypropylene tubes. The blood cells were pelleted by centrifugation at 240×g (Sorvall centrifuge at 1200 rpm) for 12 min. at 4° C. with the brake on low.

The supernatant was aspirated and the pooled pellet resuspended in 40–50 ml cold PBS (w/o Ca, Mg), and centrifuged at 240×g (Sorvall centrifuge at 1200 rpm) for 6 min. at 4° C. with the brake on high.

The supernatant was aspirated and the pellet resuspended in 12 ml of cold cell culture grade water. The suspension was titriated gently with a pipet for 30 seconds then add 4 ml of cold 0.6 M KCl. (Brought up to 50 ml with cold PBS (w/o Ca, Mg)) and then centrifuged at 300×g (Sorvall centrifuge at 1400 rpm) for 6 min. at 4° C. with the brake on high.

The above was repeated one time.

The supernatant was aspirated and the cells resuspended in 2.5 ml cold PBS (w/o Ca, Mg). The cell suspension was layered over 3 ml Ficoll-Hypaque in a 15 ml polypropylene conical tube and centrifuged at 400×g (Sorvall centrifuge at 1900 rpm) for 30 min. at 4° C. with the brake on low.

The suspension aspirated was down to the neutrophil pellet. The pellet was resuspended in cold PBS (w/o Ca, Mg) and transfered to a 50 ml conical tube and brought to 50 ml with cold PBS (w/o Ca, Mg) and centrifuged at 300×g (Sorvall centrifuge at 1400 rpm) for 6 min. at 4° C. with the brake on high.

The supernatant was aspirated and the pellet resuspended in 50 ml cold PBS (w/o Ca, Mg) and centrifuged at 300×g (Sorvall centrifuge at 1400 rpm) for 6 min. at 4° C. with the brake on high.

The supernatant was aspirated and the neutrophil pellet resuspended in 4.0 ml cold PBS (w/o Ca, Mg) on ice. 10 μl of the neutrophil cell suspension was diluted with 990 μl of Trypan blue (1:100) and cells counted using a hemacytometer. The cell number and viability were determined.

Neutrophil Culture Conditions:

The culture media was as follows:

(RPMI 1640; 10% FBS; 10 mM Hepes; 0.2 mM L-glutamine; 25 U/ml penicillin; and 25 mg/ml streptomycin)

Purified neutrophil maintenance was performed under the following conditions:

(5×10$^6$ cells/ml in above culture media; Polystyrene round-bottom 96-well plates; 250 μl/well; and 37° C., 5% CO$_2$/95% air humidified incubator) (Liles et al., Blood 119 (1995) 3181–3188).

Analysis of Hypodiploid Nuclei by Flow Cytometry:
Hypotonic fluorochrome solution
(50 µg/ml propidium iodide (Sigma catalog #P4170); 0.1% Triton X-100; and 0.1% sodium citrate).

Neutrophils were pelleted at 4° C. and the supernate aspirated.

Neutrophils were resuspended in hypotonic fluorochrome solution at a density of $5 \times 10^6$ cells/ml. Propidium iodide fluorescence of individual nuclei was evaluated in FL2 and measured on a logarithmic scale while gating on physical parameters in forward and side scatter to exlude cell debris.

At least 10,000 events per sample were collected and the results were evaluated relative to a non-apoptotic neutrophil population. (Liles et al., Blood 119 (1995) 3181–3188).
Respiratory Burst in Isolated Neutrophils Measured by Chemiluminescence Whole blood anticoagulated with Acid Citrate Dextrose (ACD) with a ratio of 1:5 ACD to blood was collected (150 ml).

Neutrophils were isolated as described above.

Opsonized zymosan was prepared by suspending 125 mg zymosan particles in 25 ml pooled human serum (5 mg/ml) and incubating them for 20 minutes at 37° C. Centrifuige the suspension and resuspend the particles in 7 ml of PBS (18 mg/ml) and stored on ice until use (vortex prior to pipetting).

50 ml of a 250 µM solution of Lucigenin (MW 510.5) was prepared by dissolving 6.4 mg of the solid in 50 ml of PBS-G (+Ca, Mg). 10 µl of PBS-G (+Ca, Mg) to the wells in a white 96 well plate.

50 µl of the 250 µM Lucigenin solution was added to the wells in a white 96 well plate.

Cell preparations were obatined from cell culture (concentration at time zero=$5.0 \times 10^6$ cells/ml) with PBS-G (+Ca, Mg).

20 µl of the neutrophil suspension was suspended to the appropriate wells and the plate was incubated the plate at 37° C. for three minutes. 10 µl of the opsonized zymosan was added to the wells.

The plate was read on the luminometer (Labsystems Luminoskan, Needham Heights, Mass.) for 14 min. at 37° C. in the kinetic mode and record results using the software DeltaSoft.
Whole Blood Assay:
The following reagents were used:
anti-CD32-FITC monoclonal antibody obtained from Pharmingen.

Lysing Solution (10× Stock: 89.9 g NH4Cl; 10.0 g KHCO; 0.37 g tetrasodium EDTA; dissolve in 1 liter dH20. Adjust to pH 7.3. Store at 4° C. in a tightly closed bottle. Dilute 1:10 with dH20 prior to use.)

(DPBS without calcium or magnesium obtained from Irivine Scientific. 2% fetal bovine serum in DPBS stored at 4° C. 50 µg/ml propidium iodide in DPBS sterile filtered and stored at 4° C.)
The following protocol was followed:
200 µl blood sample/2.8 ml 1× lysis solution in a 15 ml polypropylene conical tube. Cap and invert to mix. Leave at room temperature for 3–5 minutes. Centrifuge in a table-top Sorvall at 1200 rpm for 5 minutes at 4° C. Aspirate supemate. Resuspend pellet in 200 µl/sample 2% FBS/DPBS. Add 20 µl/sample anti-CD32-FITC. Incubate 30 minutes on ice in the dark. Add 5 ml/sample DPBS. Centrifuge at 1000 rpm for 5 minutes at 4° C. Aspirate supemate. Resuspend pellet in 1 ml/sample 2% FBS/DPBS. Add 3 ml/sample ice-cold 95% EtOH dropwise while vortexing gently. Incubate samples on ice in the dark for 30 minutes. Centrifuge at 1000 rpm for 5 minutes at 4° C. Resuspend each sample in 50 µl 5 mg/ml RN'ase. Tranfer sample to 900 µl/sample 50 µg/ml Propidium Iodide in 12×75 mm Falcon polystyrene tubes. Incubate on ice for 30 minutes. Analyze samples by flow cytometry (argon laser) for forward and side scatter and fluorescence.

EXAMPLE 111

Figure 6:
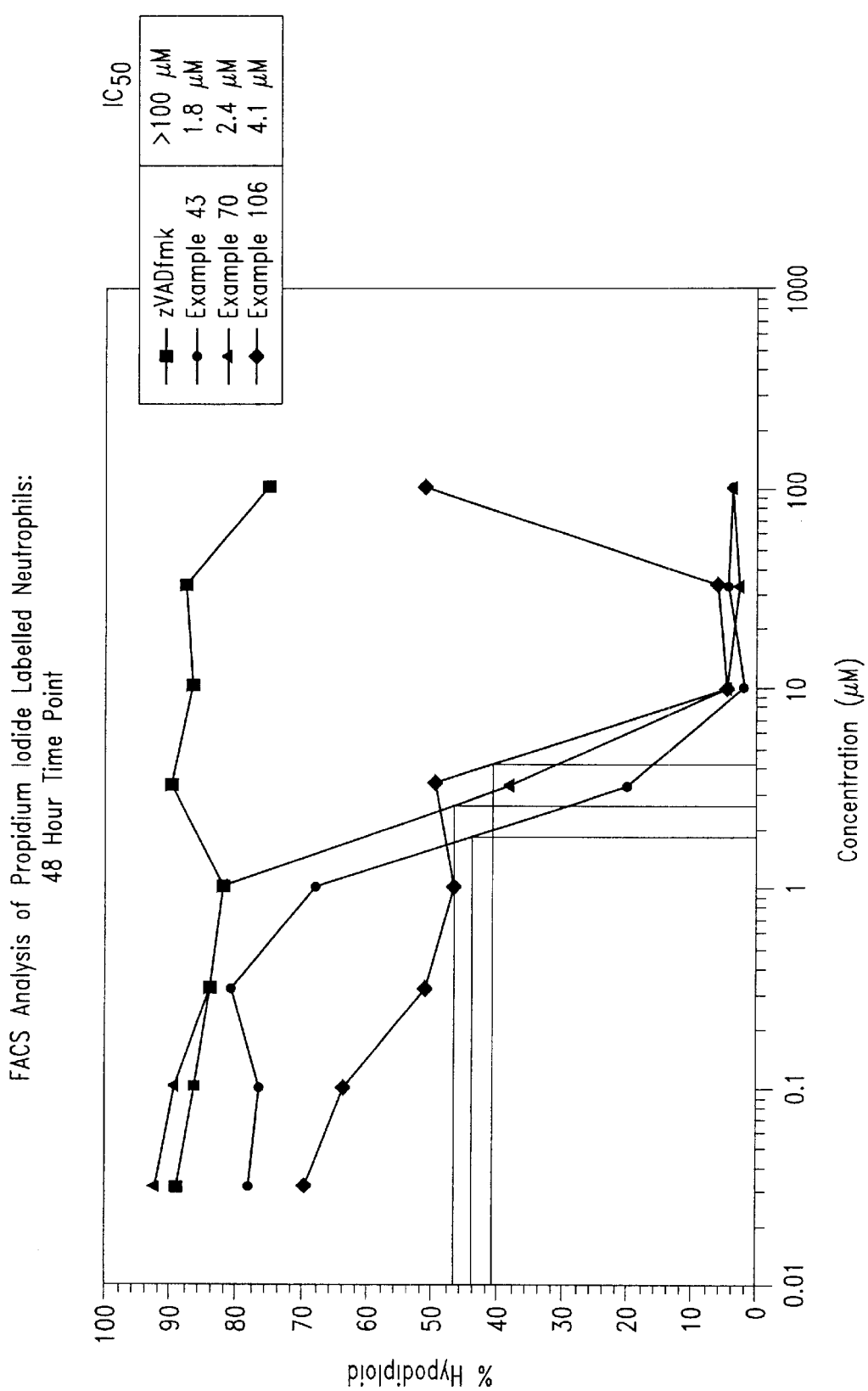
FIG. 6 shows results dervied from FACS analysis demonstrating the effect of ICE/CED-3 inhibitors on neutrophil survival as measured by DNA content (% hypodiploid).

Enhancement of Neutrophil/granulocyte Survival by Ex-vivo Application of ICE/ced-3 Inhibitors The present invention provides methods to enhance the ex vivo survival of neutrophils/granulocytes. To establish the ability of compounds to preserve granulocytes in culture, compounds were tested in a number of in vitro assays. One common model to test for effects on granulocyte survival involves separating granulocytes from fresh whole blood, culturing the cells at 37° C. and testing cells for nuclear hypodiploidy at 24 hour intervals (as described in Example 110). The presence of hypodiploid DNA is a measure of apoptosis, and is assessed using a propidium iodide stain via flow cytometry. Compounds of the present invention were incubated with the granulocytes in culture, their effects on granulocyte survival measured, and an IC50 calculated. In FIG. 6, the caspase inhibitor zVADfmk prepared as described in Tetrahedron Letter, 35 9693–9696 (1994) had a weak effect on improving granulocyte survival at 48 hours, whereas examples 43, 70, and 106 from the present invention had IC50s of <5 µM and thus are potent inhibitors of granulocyte death.

Figure 7:
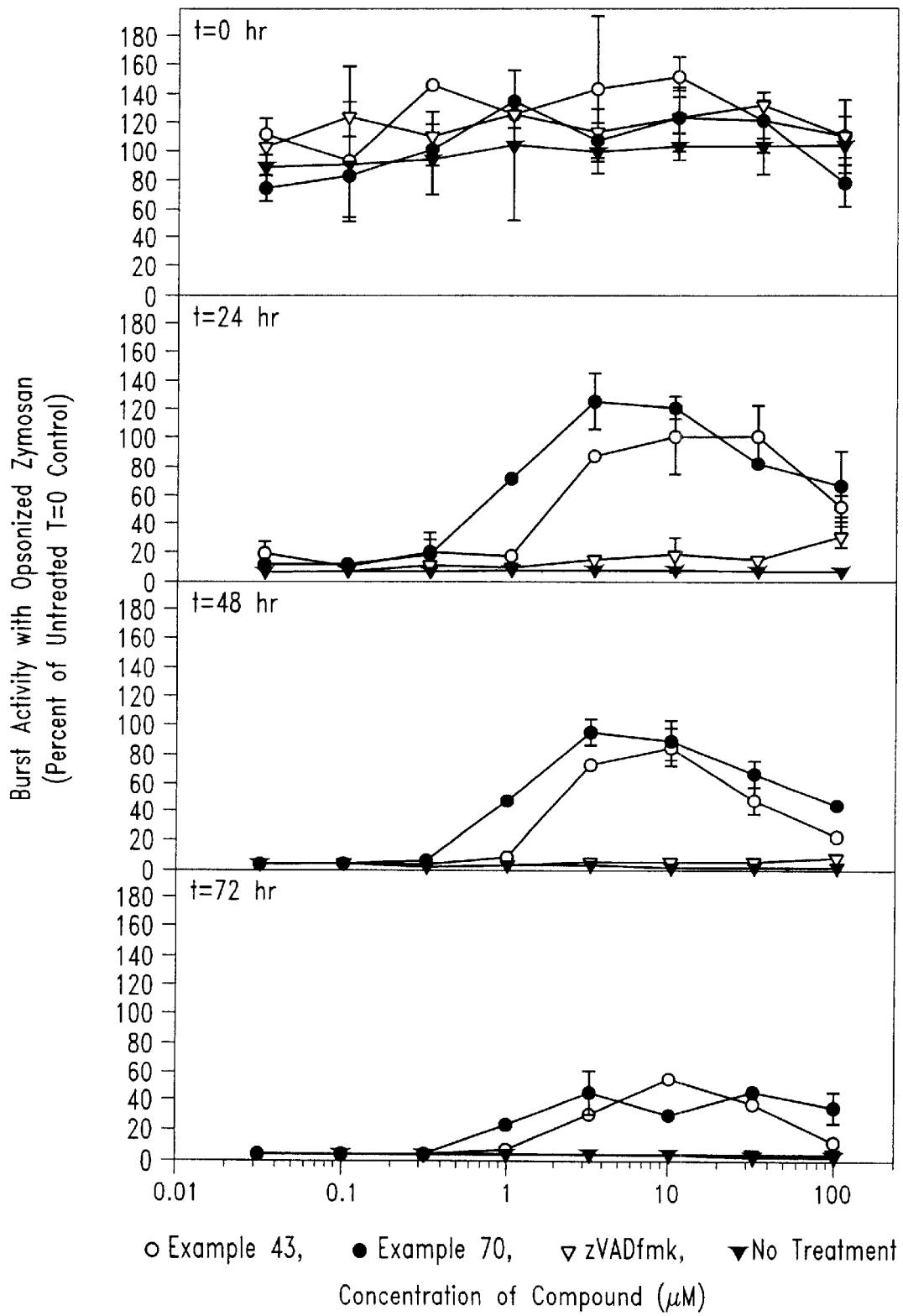
FIG. 7 shows the effect of ICE/CED-3 inhibitors or neutrophil survival as measured by the ability of live neutrophils to undergo oxidative burst.

The ability to undergo the respiratory burst is another measure of granulocyte viability. The respiratory burst is a physiological response of granulocytes to foreign stimuli such as bacteria. In this example, the method for inducing the respiratory burst utilized opsonized bacterial zymosan. The respiratory burst was measured via chemiluininescence. FIG. 7 shows that the caspase inhibitor zVADfmk, which had only weak effects on the viability of the granulocytes in the hypodiploidy experiments, did not maintain the respiratory burst. In contrast, two exemplary compounds of the present invention, example 43 and 70, substantially maintained the respiratory burst for 48 hours, and partially maintained the respiratory burst after granulocyte culture for 72 hours.

Survival of granulocytes in whole blood was measured by hypodiploid analysis in a similar fashion to isolated granulocytes via flow cytometry. ICE/ced-3 inhibitors of the present invention maintained survival of granulocytes in whole blood for 96 hours at room temperature as indicated in the table below:

Percentage of Diploid Granulocytes in Whole Blood

|  | time zero | 96 hours |
| --- | --- | --- |
| no compound | 96% | 48% |
| EXAMPLE 43 | 96% | 91% |
| EXAMPLE 70 | 96% | 89% |

Thus, the present invention provides methods for maintaining the ex vivo survival of mature granulocytes, both isolated and in whole blood. The methods of this example also provide a means to distinguish those ICE/ced-3 inhibitors that are effective in maintaining granulocyte survival from those that are not effective.

EXAMPLE 112

Enhancement of Apheresis Product Survival by Application of ICE/ced-3 Inhibitors Apheresis (leukapheresis) of blood donors can be performed to obtain a population of cells which is enriched in granulocytes. These cells are then transfused into a recipient in need of additional granulocytes. This apheresis product has a short shelf life, and current standards (American Association of Blood Banks, Standard for Blood Banks and Transfusion Services, Ed. 17, 1996) require storage at 20–24° C. for no longer than 24 hours. Transfusion is recommended within 6 hours if possible.

Exemplary compounds as described in the present invention can be used to prolong the storage life of apheresis products. ICE/ced-3 inhibitors are effective in prolonging granulocyte survival as shown in Example 64 for isolated granulocytes and whole blood. For use in the setting of apheresis, the compound can be formulated in a compatible solvent, such as dimethyl sulfoxide (DMSO). The compound can be stored in a vial, and be pre-added to the apheresis bag, or injected into the donor aphegresis line during the collection process. The effective final concentration compound could range from 1–25 $\mu$M. The leukapheresis product, containing the ICE/ced-3 inhibitor, is then infused into the recipient after storage. Many storage conditions may be possible, for example, storage may be at room temperature for up to one week post-collection.

EXAMPLE 113

Bone Marrow Reconstitution/hematopoietic Cell Recovery

In order to demonstrate utility in accelerating reconstitution of hematopoietic cells, compounds are tested in several animal models. One common model to destroy hematopoietic cells involves lethal or sub-lethal irradiation of mice, in which the animals are exposed to X-rays, usually generated from a $^{137}$Cesium source. In the case of sub-lethal irradiation, various endpoints measuring hematopoiesis can be determined at different times following the irradiation, in order to monitor recovery. Compounds of the present invention are administered to animals following sublethal irradiation and their effects on recovery are measured. The endpoints can include: hematocrit, white blood cell count, incorporation of tritiated thymidine into bone marrow DNA, spleen weight, number of burst-forming units-erythroid or number of colony-forming units (erythroid, granulocyte/macrophage and megakaryocyte forming lineages) from spleen or bone marrow from humerus or femur. In some cases animals can be further myelosuppressed by injection of chemotherapeutic agents, such as carboplatinum. Compounds which have been efficacious in these models, although acting via different mechanisms, include thrombopoeitin, Photofrin, heme, interleukin-1 and tetrachlorodecaoxide, among others.

Models of lethal irradiation can also be used to test efficacy, although these models generally include bone marrow transplant to rescue the animals. These experiments are t often performed on mice, although not exclusively. For syngeneic transplants, time to engraftment can then be measured, using the same endpoints as mentioned above. Engraftment of human progenitor cells can also be measured using SCID-hu mice as the recipients with methods similar to the above, after first establishing the human origin of the hematopoietic cells. In these cases, compounds of the present invention are administered to recipient animals at the time of bone marrow transplant. The bone marrow cells may also be treated with the ICE/CED-3 family inhibitor compounds prior to transplantation.

EXAMPLE 114

Transplantation

Transplantation studies have been performed in a variety of species with a number of organ systems, including heart, liver and kidney. The goals of these studies have included methods to optimize tissue storage prior to transplantation, and methods to minimize graft rejection. This application will focus on optimizing tissue storage, although applications to prolong graft function and minimize rejection are also possible.

Cardioplegic solutions designed to paralyze the heart are used for cardiopulmonary bypass and for transplantation. The most common of these solutions are the University of Wisconsin solution and St. Thomas' Hospital solution. The duration of time the heart can be stored prior to transplant is limited to several hours. Various experimental approaches have been taken to test additives to these solutions to prolong cardiac viability. The heart can be removed from the donor animal and function studied in an isolated preparation (commonly known as a Langendorff preparation) (Galinanes, et al., *J. Thoracic & Cardiovascular Surgery*, 104:151, 1992). Decline in cardiac function can be measured as a function of time in storage, and the parameters measured can include cardiac output, left ventricular pressure, contractile force, heart rate and coronary flow.

The effects of preservation solutions have also been studied for liver and kidney transplants. In this example, the organs are generally stored for a certain time in the solution, and then grafted into the recipient. Common endpoints for these studies are length of survival and histological examination of the graft. For liver transplants, the function of the graft can also be evaluated by measuring concentrations of alanine and aspartate aminotransferase in blood; For kidney transplants, graft function can be assessed by measuring blood concentrations of urea, blood urea nitrogen (BUN), and creatinine kinase.

As mentioned above, proper storage of organs for transplant is critical to maintain organ viability. Given the shortage of available organs, any increase in the amount of time organs can be maintained, particularly from cadavers, would be of major importance to transplantation medicine. The heart seems to be particularly susceptible to damage during isolation and storage. Improvement in these conditions could lead to an increase in the number of viable hearts available for transplant. An improved organ storage solution can also be used to perfuse the organ prior to removal, possibly additionally enhancing its protective effect. Methods of the present invention provide such an improved method, consisting of adding ICE/CED-3 inhibitors to the storage solutions.

Although the invention has been described with reference to the examples provided above, it should be understood that various modifications can be made without departing from the spirit of the invention. Accordingly, the invention is limited only by the claims.

We claim:

1. A method for preventing or treating inflammation, comprising contacting a cell population with an inhibiting effective amount of a reagent that suppresses the protease activity of at least one member of the interleukin-1beta-converting enzyme (ICE)/CED-3 family, thereby preventing or treating inflammation, wherein said inflammation is due to an inflammatory disease, and wherein said inflammatory disease is selected from the group consisting of arthritis, cholangitis, colitis, encephalitis, endocerolitis, hepatitis, pancreatitis, and reperfusion injury.

2. The method of claim 1, wherein said inflammation is chronic inflammation.

3. The method of claim 1, wherein said inflammation is acute inflammation.

4. The method of claim 1, wherein the reagent suppresses the protease activity in an irreversible manner.

5. The method of claim 1, wherein the reagent suppresses the protease activity in a reversible manner.

6. The method of claim 1, wherein the reagent is a compound of formula 1:

FORMULA 1

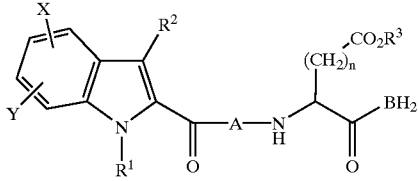

wherein:

n is 1 or 2;

$R^1$ is alkyl, cycloalkyl, (cycloalkyl)alkyl, phenyl, (substituted)phenyl, phenylalkyl, (substituted)phenylalkyl, heteroaryl, (heteroaryl)alkyl or $(CH_2)_m CO_2R^4$, wherein m=1–4, and $R^4$ is as defined below;

$R^2$ is a hydrogen atom, chloro, alkyl, cycloalkyl, (cycloalkyl)alkyl, phenyl,(substituted)phenyl, phenylalkyl, (substituted)phenylalkyl, heteroaryl, (heteroaryl)alkyl or $(CH_2)_p CO_2R^5$, wherein p=0–4, and $R^5$ is as defined below;

$R^3$ is a hydrogen atom, alkyl, cycloalkyl, (cycloalkyl)alkyl, phenylalkyl, or (substituted)phenylalkyl;

$R^4$ is a hydrogen atom, alkyl, cycloalkyl, (cycloalkyl)alkyl, phenylalkyl, or (substituted)phenylalkyl;

$R^5$ is a hydrogen atom, alkyl, cycloalkyl, (cycloalkyl)alkyl, phenylalkyl, or (substituted)phenylalkyl;

A is a natural and unnatural amino acid;

B is a hydrogen atom, a deuterium atom, alkyl, cycloalkyl, (cycloalkyl)alkyl, phenyl,(substituted)phenyl, phenylalkyl, (substituted)phenylalkyl, beteroaryl, (heteroaryl)alkyl, halomethyl, $CH_2ZR^6$, $CH_2OCO(aryl)$, $CH_2OCO(heteroaryl)$; or $CH_2OPO(R^7)R^8$ where Z is an oxygen or a sulfur atom;

$R^6$ is phenyl, substituted phenyl, phenylalkyl, substituted phenylalkyl, heteroaryl, or (heteroaryl)alkyl; and $R^7$ and $R^8$ are independently selected from a group consisting of alkyl, cycloalkyl, phenyl, substituted phenyl, phenylalkyl, (substituted phenyl) alkyl, and (cycloalkyl) alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl;

or a pharmaceutically acceptable salt thereof.

7. The method of claim 1, wherein the reagent is a compound of formula 3:

FORMULA 3

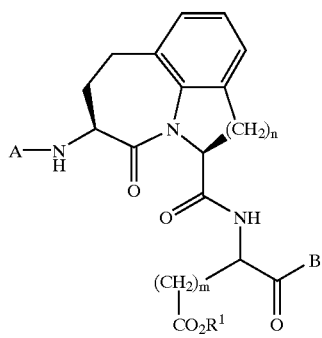

wherein:

n is 1 or 2;

m is 1 or 2;

A is $R^2CO—$, $R^3—O—CO—$, or $R^4SO_2—$;

a group of the formula:

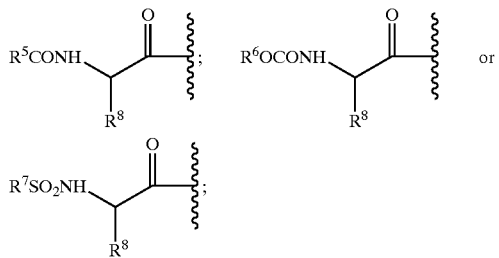

further wherein:

$R^1$ is a hydrogen atom, alkyl or phenylalkyl;

$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^3$ is alkyl, cycloalkyl, (cycloalkyl)alk yl, phenyl alkyl, or (substituted phenyl)alkyl;

$R^4$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^5$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^6$ is alkyl, cycloalkyl, (cycloalkyl)alkyl, phenylalkyl, or (substituted phenyl)alkyl;

$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^8$ is an amino acid side chain chosen from the group consisting of natural and unnatural amino acids;

B is a hydrogen atom, a deuterium atom, alkyl, cycloalkyl, (cycloalkyl)alkyl, phenyl, phenylalkyl, substituted phenyl, (substituted phenyl)alkyl, heteroaryl, (heteroaryl)alkyl, or halomethyl;

a group of the formula:

—CH$_2$XR$^9$;

wherein R$^9$ is phenyl, substituted phenyl, phenylalkyl, (substituted phenyl)alkyl, heteroaryl, or (heteroaryl)alkyl; and X is an oxygen or a sulfur atom;

a group of the formula:

—CH$_2$—O—CO—(ARYL);

a group of the formula:

—CH$_2$—O—CO—(HETEROARYL);

a group of the formula:

—CH$_2$—O—PO(R$^{10}$)R$^{11}$ wherein R$^{10}$ and R$^{11}$ are independently selected from a group consisting of alkyl, cycloalkyl, phenyl, substituted phenyl, phenylalkyl and (substituted phenyl)alkyl; and the pharmaceutically-acceptable salts thereof.

* * * * *

UNITED STATES PATENT AND TRADEMARK OFFICE
CERTIFICATE OF CORRECTION

PATENT NO. : 6,528,506 B2
DATED : March 4, 2003
INVENTOR(S) : Lawrence C. Fritz et al.

It is certified that error appears in the above-identified patent and that said Letters Patent is hereby corrected as shown below:

Column 79,
Line 23, the symbol at the end of Formula 1 should be -- B --, and the formula should appear as:

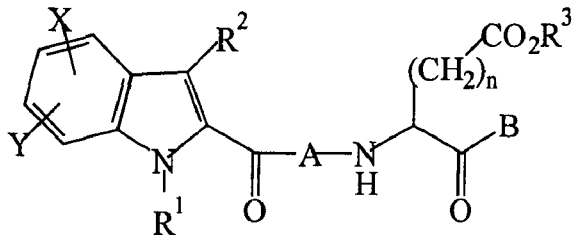

FORMULA 1

Line 55, "beteroaryl" should read as -- heteroaryl --.

Column 80,
Line 52, "alk yl, phenyl alkyl" should read as -- alkyl, phenylalkyl --.

Signed and Sealed this

Twelfth Day of August, 2003

JAMES E. ROGAN
*Director of the United States Patent and Trademark Office*